US012667126B2

(12) United States Patent
Xiang et al.

(10) Patent No.: US 12,667,126 B2
(45) Date of Patent: Jun. 30, 2026

(54) MALONYL STEVIOL GLYCOSIDES AND THEIR COMESTIBLE USE

(71) Applicant: Firmenich SA, Satigny (CH)

(72) Inventors: Wen-Juan Xiang, Shanghai (CN); Dan-Ting Yin, Shanghai (CN); Yi-Chun Ding, Shanghai (CN)

(73) Assignee: FIRMENICH SA, Satigny (CH)

( * ) Notice: Subject to any disclaimer, the term of this patent is extended or adjusted under 35 U.S.C. 154(b) by 587 days.

(21) Appl. No.: 18/015,141

(22) PCT Filed: Oct. 12, 2021

(86) PCT No.: PCT/EP2021/078086
§ 371 (c)(1),
(2) Date: Jan. 9, 2023

(87) PCT Pub. No.: WO2022/078974
PCT Pub. Date: Apr. 21, 2022

(65) Prior Publication Data

US 2023/0329299 A1 Oct. 19, 2023

(30) Foreign Application Priority Data

Nov. 11, 2020 (EP) .................................... 20206827

(51) Int. Cl.
*A23L 27/30* (2016.01)
*A23L 27/00* (2016.01)
*C07H 15/256* (2006.01)

(52) U.S. Cl.
CPC ............... *A23L 27/36* (2016.08); *A23L 27/88* (2016.08); *C07H 15/256* (2013.01)

(58) Field of Classification Search
CPC ............................ A23L 27/36; C07H 15/256
See application file for complete search history.

(56) References Cited

U.S. PATENT DOCUMENTS 2,809,895 A 10/1957 Swisher
3,041,180 A 6/1962 Swisher
(Continued)

FOREIGN PATENT DOCUMENTS

WO WO 2012/146584 A2 11/2012
WO 2017/156432 9/2017
(Continued)

OTHER PUBLICATIONS

International Search Report and Written Opinion for corresponding International Application No. PCT/EP2021/078086 dated Jan. 27, 2022.
(Continued)

*Primary Examiner* — Changqing Li
(74) *Attorney, Agent, or Firm* — Knobbe, Martens, Olson & Bear, LLP

(57) ABSTRACT

The present disclosure relates generally to malonyl steviol glycosides and the use of such compounds for various comestible uses, such as sweetening a flavored product or enhancing the sweetness of another sweetener. In some aspects, the disclosure provides certain compositions that include such malonyl steviol glycosides, such as compositions that include such malonyl steviol glycosides and one or more other sweeteners. In some other aspects, the disclosure provides methods of reducing the caloric content of a flavored article, such as a flavored food or beverage product, or an oral care product.

5 Claims, 23 Drawing Sheets

(56) References Cited

U.S. PATENT DOCUMENTS

| | | | |
|---|---|---|---|
| 3,704,137 | A | 11/1972 | Beck |
| 4,404,367 | A | 9/1983 | Stephenson |
| 4,610,890 | A | 9/1986 | Miller |
| 4,689,235 | A | 8/1987 | Barnes |
| 5,603,971 | A | 2/1997 | Porzio |
| 5,786,017 | A | 7/1998 | Blake |
| 5,897,897 | A | 4/1999 | Porzio |
| 6,416,799 | B1 | 7/2002 | Porzio |
| 6,468,576 | B1 | 10/2002 | Sher |
| 6,607,771 | B2 | 8/2003 | Benczedi |
| 6,932,982 | B2 | 8/2005 | McIver |
| 7,488,503 | B1 | 2/2009 | Porzio |
| 8,076,491 | B2 | 12/2011 | Karanewsky |
| 8,124,121 | B2 | 2/2012 | Tachdjian |
| 8,445,692 | B2 | 5/2013 | Karanewsky |
| 8,541,421 | B2 | 9/2013 | Tachdjian |
| 8,592,592 | B2 | 11/2013 | Tachdjian |
| 8,735,081 | B2 | 5/2014 | Li |
| 8,815,956 | B2 | 8/2014 | Tachdjian |
| 8,877,922 | B2 | 11/2014 | Tachdjian |
| 8,968,708 | B2 | 3/2015 | Tachdjian |
| 8,993,027 | B2 | 3/2015 | Prakash |
| 9,000,051 | B2 | 4/2015 | Feltin |
| 9,000,054 | B2 | 4/2015 | Tachdjian |
| 9,247,759 | B2 | 2/2016 | Karanewsky |
| 9,394,287 | B2 | 7/2016 | Priest |
| 9,834,544 | B2 | 12/2017 | Tachdjian |
| 10,421,727 | B2 | 9/2019 | Chumakova |
| 2007/0128234 | A1 | 6/2007 | Subramaniam |
| 2010/0172945 | A1 | 7/2010 | Gregson |
| 2012/0027866 | A1 | 2/2012 | Gregson |
| 2014/0056836 | A1 | 2/2014 | Subramaniam |
| 2015/0164117 | A1 | 6/2015 | Kaplan |
| 2015/0257424 | A1 | 9/2015 | Catani et al. |
| 2016/0039856 | A1 | 2/2016 | Prakash et al. |
| 2016/0235102 | A1 | 8/2016 | Oglesby |
| 2016/0346752 | A1 | 12/2016 | Struillou |
| 2017/0119032 | A1 | 5/2017 | Patron |
| 2018/0103667 | A1 | 4/2018 | Womack |
| 2018/0116266 | A1 | 5/2018 | Jackson |
| 2018/0263269 | A1 | 9/2018 | Prakash et al. |
| 2018/0363074 | A1 | 12/2018 | Gregson |
| 2018/0369777 | A1 | 12/2018 | Shi |
| 2019/0082727 | A1 | 3/2019 | Van Sleeuwen |
| 2019/0343159 | A1 | 11/2019 | Carlson et al. |

FOREIGN PATENT DOCUMENTS

| | | | |
|---|---|---|---|
| WO | 2021/216546 | 10/2021 | |
| WO | 2021/216549 | 10/2021 | |
| WO | WO-2021216553 A1 * | 10/2021 | ............. A23L 27/36 |

OTHER PUBLICATIONS

Supplemental International Search Report and Written Opinion for corresponding International Application No. PCT/EP2021/078086 dated Mar. 18, 2022.

Du Bois et al., J. Med. Chem., vol. 28, pp. 93-98 (1985).

"Herbal Product Stevia Leaves", XP002805730, dated Jan. 1, 2015.

Mitchell, 2006, Sweeteners and Sugar Alternatives in Food Technology Blackwell Publishing Ltd. (TOC).

National Academy of Sciences, 1965, Chemicals Used in Food Processing, publication 1274, pp. 63-258.

* cited by examiner

MALONYL STEVIOL GLYCOSIDES AND THEIR COMESTIBLE USE

CROSS-REFERENCE TO RELATED APPLICATIONS

The present application is the United States national-stage patent application of international PCT Application No. PCT/EP2021/078086, filed Oct. 12, 2021, which claims priority to PCT Application No. PCT/CN2020/120590, filed Oct. 13, 2020, and European Patent Application No. 20206827.6, filed Nov. 11, 2020, both of which are incorporated by reference as though set forth herein in their entireties.

TECHNICAL FIELD

The present disclosure relates generally to malonyl steviol glycosides and the use of such compounds for various comestible uses, such as sweetening a flavored product or enhancing the sweetness of another sweetener. In some aspects, the disclosure provides certain compositions that include such malonyl steviol glycosides, such as compositions that include such malonyl steviol glycosides and one or more other sweeteners. In some other aspects, the disclosure provides methods of reducing the caloric content of a flavored article, such as a flavored food or beverage product, or an oral care product.

DESCRIPTION OF RELATED ART

The taste system provides sensory information about the chemical composition of the external world. Taste transduction is one of the more sophisticated forms of chemically triggered sensation in animals. Signaling of taste is found throughout the animal kingdom, from simple metazoans to the most complex of vertebrates. Mammals are believed to have five basic taste modalities: sweet, bitter, sour, salty, and umami.

Sweetness is the taste most commonly perceived when eating foods rich in sugars. Mammals generally perceive sweetness to be a pleasurable sensation, except in excess. Caloric sweeteners, such as sucrose and fructose, are the prototypical examples of sweet substances. Although a variety of no-calorie and low-calorie substitutes exist, these caloric sweeteners are still the predominant means by which comestible products induce the perception of sweetness upon consumption.

Metabolic disorders and related conditions, such as obesity, diabetes, and cardiovascular disease, are major public health concerns throughout the world. And their prevalence is increasing at alarming rates in almost every developed country. Caloric sweeteners are a key contributor to this trend, as they are included in various packaged food and beverage products to make them more palatable to consumers. In many cases, no-calorie or low-calorie substitutes can be used in foods and beverages in place of sucrose or fructose. Even so, these compounds impart sweetness differently from caloric sweeteners, and a number of consumers fail to view them as suitable alternatives. Moreover, such compounds may be difficult to incorporate into certain products. In some instances, they may be used as partial replacements for caloric sweeteners, but their mere presence can cause many consumers to perceive unpleasant off-tastes including, astringency, bitterness, and metallic and licorice tastes. Thus, lower-calorie sweeteners face certain challenges to their adoption.

Sweetness enhancement provides an alternative approach to overcoming some of adoption challenges faced by lower-calorie sweeteners. Such compounds can be used in combination with sucrose or fructose to enhance their sweetness, thereby permitting the use of lower quantities of such caloric sweeteners in various food or beverage products. But, in addition to enhancing the perceived sweetness of the primary sweetener, such compounds nevertheless alter the perceived taste of the sweetener. Thus, many consumers find that it is less pleasurable to consume such sweetness-enhanced products in comparison to unenhanced alternatives having higher calories. Thus, there is a continuing need to discover compounds that enhance the sweetness of caloric sweeteners without altering their perceived taste in a way that detracts from the pleasure that consumers experience in eating or drinking products containing such sweeteners.

SUMMARY

The present disclosure relates to the discovery that certain compounds exhibit a desirable and surprising sweetness enhancing effect when combined with primary sweeteners at amounts effective to enhance sweetness.

In a first aspect, the disclosure provides flavor-modifying compounds, which are compounds of formula (I):

(I)

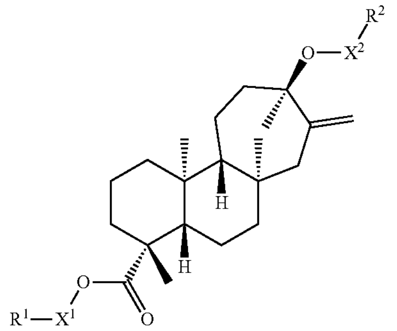

or salts thereof, wherein:

$R^1$ and $R^2$ are independently —H or a moiety of the formula —C(O)—$CH_2$—C(O)—$OR^3$, wherein $R^1$ and $R^2$ are not both —H; and $X^1$ and $X^2$ are independently a direct bond or a saccharide moiety that comprises from 1 to 5 monosaccharide units, wherein $X^1$ and $X^2$ are not both a direct bond.

In a second aspect, the disclosure provides uses of any flavor-modifying compounds of the first aspect.

In a third aspect, the disclosure provides uses of any flavor-modifying compounds of the first aspect to sweeten a comestible composition. In some embodiments thereof, the comestible composition comprises a caloric sweetener. In some other embodiments thereof, the comestible composition comprises a non-caloric sweetener. In some embodiments, the sweetener is a high-intensity sweetener.

In a fourth aspect, the disclosure provides uses of any flavor-modifying compounds of the first aspect to enhance the sweetness of a comestible composition. In some embodiments thereof, the comestible composition comprises a caloric sweetener. In some other embodiments thereof, the comestible composition comprises a non-caloric sweetener. In some embodiments, the sweetener is a high-intensity sweetener.

In a fifth aspect, the disclosure provides uses of any flavor-modifying compounds of the first aspect to reduce the sourness of a comestible composition.

In a sixth aspect, the disclosure provides uses of any flavor-modifying compounds of the first aspect to reduce the bitterness of a comestible composition.

In a seventh aspect, the disclosure provides uses of any flavor-modifying compounds of the first aspect in the manufacture of a comestible composition to sweeten a comestible composition or to enhance the sweetness of the comestible composition. In some embodiments thereof, the comestible composition comprises a caloric sweetener. In some other embodiments thereof, the comestible composition comprises a non-caloric sweetener. In some embodiments, the sweetener is a high-intensity sweetener.

In an eighth aspect, the disclosure provides uses of any flavor-modifying compounds of the first aspect in the manufacture of a comestible composition to reduce the sourness of the comestible composition.

In a ninth aspect, the disclosure provides uses of any flavor-modifying compounds of the first aspect in the manufacture of a comestible composition to reduce the bitterness of the comestible composition.

In a tenth aspect, the disclosure provides methods of sweetening a comestible composition, comprising introducing an amount (such as a sweetness-enhancing effective amount) of any compounds of the first aspect to the comestible composition. In a related aspect, the disclosure provides methods of enhancing the sweetness of a comestible composition, comprising introducing an amount (such as a sweetness-enhancing effective amount) of any compounds of the first aspect to the comestible composition.

In an eleventh aspect, the disclosure provides methods of reducing the sourness of a comestible composition, comprising introducing an amount (such as a sourness-reducing effective amount) of any compounds of the first aspect to the comestible composition.

In a twelfth aspect, the disclosure provides methods of reducing the bitterness of a comestible composition, comprising introducing an amount (such as a bitterness-reducing effective amount) of any compounds of the first aspect to the comestible composition.

In a thirteenth aspect, the disclosure provides compositions comprising any compounds of the first aspect. In some embodiments, the compounds of the first aspect make up at least 20% by weight of the compositions on a dry weight basis (e.g., based on the total weight of the composition excluding the weight of any liquid carrier).

In a fourteenth aspect, the disclosure provides solid-state compositions comprising any compounds of the first aspect, wherein the compounds of the first aspect make up at least 20% by weight of the solid-state compositions, based on the total weight of composition.

In a fifteenth aspect, the disclosure provides comestible compositions comprising any compounds of the first aspect, wherein the concentration of the compounds of the first aspect in the comestible compositions is no more than 200 ppm. In some embodiments, the comestible composition is not a naturally occurring composition.

In a sixteenth aspect, the disclosure provides comestible compositions comprising any compounds of the first aspect and, optionally, a sweetener. In some embodiments, the sweetener is a caloric sweetener, such as sucrose, fructose, glucose, xylitol, erythritol, or combinations thereof. In some embodiments, the sweetener is a non-caloric sweetener, such as a steviol glycoside, a mogroside, aspartame, sucralose, acesulfame K, saccharin, or any combinations thereof. In some embodiments, the comestible composition comprises one or more high-intensity sweeteners.

In a seventeenth aspect, the disclosure provides a concentrated sweetening composition comprising any compounds of the first aspect and a sweetener.

In an eighteenth aspect, the disclosure provides flavored products comprising any compositions of the preceding five aspects. In some embodiment, the flavored products are beverage products, such as soda, flavored water, tea, and the like. In some other embodiments, the flavored products are food products, such as yogurt.

Further aspects, and embodiments thereof, are set forth below in the Detailed Description, the Drawings, the Abstract, and the Claims.

BRIEF DESCRIPTION OF THE DRAWINGS

The following drawings are provided for purposes of illustrating various embodiments of the compositions and methods disclosed herein. The drawings are provided for illustrative purposes only, and are not intended to describe any preferred compositions or preferred methods, or to serve as a source of any limitations on the scope of the claimed inventions.

DETAILED DESCRIPTION

Figure 1:
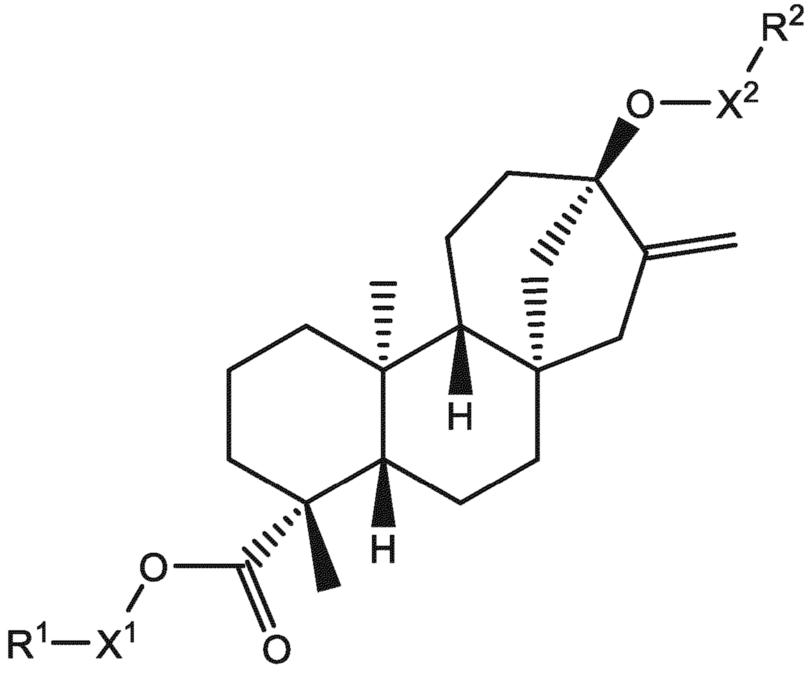
FIG. 1 shows a chemical formula that represents non-limiting examples of compounds (or salts thereof) disclosed herein, wherein: $R^1$ and $R^2$ are independently —H or moiety of the formula —C(O)—$CH_2$—C(O)—OH, wherein both $R^1$ and $R^2$ are not both —H; and $X^1$ and $X^2$ are independently a saccharide moiety, which comprises from 1 to 5 monosaccharide units.

The following Detailed Description sets forth various aspects and embodiments provided herein. The description is to be read from the perspective of the person of ordinary skill in the relevant art. Therefore, information that is well known to such ordinarily skilled artisans is not necessarily included.

Definitions

The following terms and phrases have the meanings indicated below, unless otherwise provided herein. This disclosure may employ other terms and phrases not expressly defined herein. Such other terms and phrases have the meanings that they would possess within the context of this disclosure to those of ordinary skill in the art. In some instances, a term or phrase may be defined in the singular or plural. In such instances, it is understood that any term in the singular may include its plural counterpart and vice versa, unless expressly indicated to the contrary As used herein, "solvate" means a compound formed by the interaction of one or more solvent molecules and one or more compounds described herein. In some embodiments, the solvates are ingestibly acceptable solvates, such as hydrates.

As used herein, "$C_a$ to $C_b$" or "$C_{a-b}$" in which "a" and "b" are integers, refer to the number of carbon atoms in the specified group. That is, the group can contain from "a" to "b", inclusive, carbon atoms. Thus, for example, a "$C_1$ to $C_4$ alkyl" or "$C_{1-4}$ alkyl" group refers to all alkyl groups having from 1 to 4 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$— and $(CH_3)_3C$—.

As used herein, a "monosaccharide unit" is a monovalent or polyvalent moiety in which one or more of the hydroxyl groups of the monosaccharide are replaced by an ether linkage (oxygen atom linkage) to the steviol core structure, a malonyl moiety, or one or more other monosaccharide units. The monosaccharide units can have either an open (acyclic) configuration of a closed (cyclic) configuration, and can have any suitable stereochemistry. Unless otherwise specified, the glucose can have any suitable stereochemistry (e.g., D or L, and alpha or beta). The carbon atoms of the saccharide moiety follow the conventional numbering, as shown below for a β-D glucose unit (as a non-limiting example), but applies in an analogous way to other monosaccharide units in an analogous way:

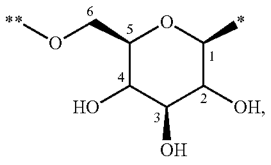

where the * and ** denote covalent connections to other monosaccharide units, the malonyl moiety, a hydrogen atom, or the steviol moiety. For example, the monosaccharide unit shown here may, for example, be X1, where the * denotes a connection to the oxygen atom of the steviol moiety, and the ** denotes a connection to $R^1$. This example shows a divalent monosaccharide unit. In some other examples, the monosaccharide unit can be monovalent, trivalent, and the like.

As used herein, a "saccharide moiety" is a divalent moiety that includes from one (1) to five (5) monosaccharide units. When the saccharide moiety includes two or more monosaccharide units, the saccharide units are connected to each other via an ether linkage (oxygen atom linkage).

It is to be understood that certain radical naming conventions can include either a mono-radical or a di-radical, depending on the context. For example, where a substituent requires two points of attachment to the rest of the molecule, it is understood that the substituent is a di-radical. For example, a substituent identified as alkyl that requires two points of attachment includes di-radicals such as —$CH_2$—, —$CH_2CH_2$—, —$CH_2CH(CH_3)CH_2$—, and the like.

Wherever a substituent is depicted as a di-radical (i.e., has two points of attachment to the rest of the molecule), it is to be understood that the substituent can be attached in any directional configuration unless otherwise indicated. Thus, for example, a substituent depicted as -AE- or

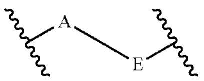

includes the substituent being oriented such that the A is attached at the leftmost attachment point of the molecule as well as the case in which A is attached at the rightmost attachment point of the molecule.

A "sweetener", "sweet flavoring agent", "sweet flavor entity", or "sweet compound" herein refers to a compound or ingestibly acceptable salt thereof that elicits a detectable sweet flavor in a subject, e.g., a compound that activates a T1R2/T1R3 receptor in vitro.

As used herein, the singular forms "a," "an," and "the" include plural referents unless the context clearly dictates otherwise. For example, reference to "a substituent" encompasses a single substituent as well as two or more substituents, and the like.

As used herein, "for example," "for instance," "such as," or "including" are meant to introduce examples that further clarify more general subject matter. Unless otherwise expressly indicated, such examples are provided only as an aid for understanding embodiments illustrated in the present disclosure, and are not meant to be limiting in any fashion. Nor do these phrases indicate any kind of preference for the disclosed embodiment.

As used herein, "comprise" or "comprises" or "comprising" or "comprised of" refer to groups that are open, meaning that the group can include additional members in addition to those expressly recited. For example, the phrase, "comprises A" means that A must be present, but that other members can be present too. The terms "include," "have," and "composed of" and their grammatical variants have the same meaning. In contrast, "consist of" or "consists of" or "consisting of" refer to groups that are closed. For example, the phrase "consists of A" means that A and only A is present.

As used herein, "optionally" means that the subsequently described event(s) may or may not occur. In some embodiments, the optional event does not occur. In some other embodiments, the optional event does occur one or more times.

As used herein, "or" is to be given its broadest reasonable interpretation, and is not to be limited to an either/or construction. Thus, the phrase "comprising A or B" means that A can be present and not B, or that B is present and not A, or that A and B are both present. Further, if A, for example, defines a class that can have multiple members, e.g., $A_1$ and $A_2$, then one or more members of the class can be present concurrently.

As used herein, certain substituents or linking groups having only a single atom may be referred to by the name of the atom. For example, in some cases, the substituent "—H" may be referred to as "hydrogen" or "a hydrogen atom," the substituent "—F" may be referred to as "fluorine" or "a fluorine atom," and the linking group "—O—" may be referred to as "oxygen" or "an oxygen atom."

Points of attachment for groups are generally indicated by a terminal dash (-) or by an asterisk (*). For example, a group such as $*—CH_2—CH_3$ or $—CH_2—CH_3$ both represent an ethyl group.

Chemical structures are often shown using the "skeletal" format, such that carbon atoms are not explicitly shown, and hydrogen atoms attached to carbon atoms are omitted entirely. For example, the structure

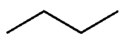

represents butane (i.e., n-butane). Furthermore, aromatic groups, such as benzene, are represented by showing one of the contributing resonance structures. For example, the structure

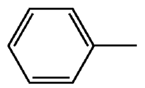

represents toluene.

Other terms are defined in other portions of this description, even though not included in this subsection.

Malonyl Steviol Glycosides

In a first aspect, the disclosure provides flavor-modifying compounds, which are compounds of formula (I):

(I)

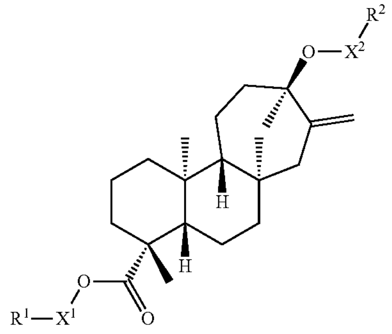

or salts thereof, wherein:

$R^1$ and $R^2$ are independently —H or moiety of the formula —C(O)—$CH_2$—C(O)—OH, wherein $R^1$ and $R^2$ are not both —H; and $X^1$ and $X^2$ are independently a direct bond or a saccharide moiety that comprises from 1 to 5 monosaccharide units, wherein $X^1$ and $X^2$ are not both a direct bond.

$R^1$ and $R^2$ can have any suitable value, according to the definitions set forth above. In some embodiments, $R^1$ is —H and $R^2$ is —C(O)—$CH_2$—C(O)—OH. In some other embodiments, $R^1$ is —C(O)—$CH_2$—C(O)—OH and $R^2$ is —H. In some other embodiments, $R^1$ and $R^2$ are both —C(O)—$CH_2$—C(O)—OH.

$X^1$ can have any suitable value according to the definitions set forth above. In some embodiments of any of the foregoing embodiments, $X^1$ comprises one or two saccharide units. In some such embodiments, $X^1$ comprises one saccharide unit. In some other such embodiments, $X^1$ comprises two saccharide units. In some further such embodiments of the foregoing embodiments, the saccharide units are glucose units, galactose units, rhamnose units, arabinose units, xylose units, 6-deoxyglucose units, or any combination thereof. In some such embodiments, $X^1$ comprises at least one D-glucose unit.

$X^2$ can have any suitable value according to the definitions set forth above. In some embodiments of any of the foregoing embodiments, $X^2$ comprises from 1 to 4, or from 1 to 3, saccharide units. In some such embodiments, $X^2$ comprises one saccharide unit. In some other such embodiments, $X^2$ comprises two saccharide units. In some other such embodiments, $X^2$ comprises three saccharide units. In some other such embodiments, $X^2$ comprises four saccharide units. In some further such embodiments of the foregoing embodiments, the saccharide units are glucose units, galactose units, rhamnose units, arabinose units, xylose units, 6-deoxyglucose units, or any combination thereof. In some such embodiments, $X^2$ comprises at least one D-glucose unit.

In some embodiments of any of the foregoing embodiments, one of —$X^1$—$R^1$ or —$X^2$—$R^2$ is a moiety selected from the group consisting of: a hydrogen atom, 1-β-D-glucopyranosyl, 2-(1-β-D-glucopyranosyl)-1-β-D-glucopyranosyl, 3-(1-β-D-glucopyranosyl)-1-β-D-glucopyranosyl, 6-(1-β-D-glucopyranosyl)-1-β-D-glucopyranosyl, 2-(1-α-D-glucopyranosyl)-1-β-D-glucopyranosyl, 3-(1-α-D-glucopyranosyl)-1-β-D-glucopyranosyl, 6-(1-α-D-glucopyranosyl)-1-β-D-glucopyranosyl, 2-(1-α-L-rhamnopyranosyl))-1-β-D-glucopyranosyl, 2-(1-β-D-xylopyranosyl)-1-β-D-glucopyranosyl, 6-(1-β-D-xylopyranosyl)-1-β-D-glucopyranosyl, 2-(1-β-D-6-deoxy glucopyranosyl)-1-β-D-glucopyranosyl, 2-(1-α-L-arabinopyranosyl))-1-β-D-glucopyranosyl, 6-(1-α-L-arabinopyranosyl))-1-β-D-glucopyranosyl, 2-(1-β-D-galactopyranosyl))-1-β-D-glucopyranosyl, 6-(1-β-D-galactopyranosyl))-1-β-D-glucopyranosyl, 2,3-bis(1-β-D-glucopyranosyl)-1-β-D-glucopyranosyl, 2,6-bis(1-β-D-glucopyranosyl)-1-β-D-glucopyranosyl, 2-(1-α-L-rhamnopyranosyl)-3-(1-β-D-glucopyranosyl)-1-β-D-glucopyranosyl, 2-(1-β-D-xylopyranosyl)-3-(1-β-D-glucopyranosyl)-1-β-D-glucopyranosyl, 2-(1-β-D-6 deoxy glucopyranosyl)-3-(1-β-D-glucopyranosyl)-1-β-D-glucopyranosyl, and 2,3,6,-tris(1-β-D-glucopyranosyl)-1-β-D-glucopyranosyl. In some such embodiments, —$X^1$—$R^1$ is a moiety selected from the group consisting of: a hydrogen atom, 1-β-D-glucopyranosyl, 2-(1-β-D-glucopyranosyl)-1-β-D-glucopyranosyl, 3-(1-β-D-glucopyranosyl)-1-β-D-glucopyranosyl, 6-(1-β-D-glucopyranosyl)-1-β-D-glucopyranosyl, 2-(1-α-D-glucopyranosyl)-1-β-D-glucopyranosyl, 3-(1-α-D-glucopyranosyl)-1-β-D-glucopyranosyl, 6-(1-α-D-glucopyranosyl)-1-β-D-glucopyranosyl, 2-(1-α-L-rhamnopyranosyl))-1-β-D-glucopyranosyl, 2-(1-β-D-xylopyranosyl)-1-β-D-glucopyranosyl, 6-(1-β-D-xylopyranosyl)-1-β-D-glucopyranosyl, 2-(1-β-D-6-deoxy glucopyranosyl)-1-β-D-glucopyranosyl, 2-(1-α-L-arabinopyranosyl))-1-β-D- glucopyranosyl, 6-(1-α-L-arabinopyranosyl))-1-β-D-glucopyranosyl, 2-(1-β-D-galactopyranosyl))-1-β-D-glucopyranosyl, 6-(1-β-D-galactopyranosyl))-1-β-D-glucopyranosyl, 2,3-bis(1-β-D-glucopyranosyl)-1-β-D-glucopyranosyl, 2,6-bis(1-β-D-glucopyranosyl)-1-β-D-glucopyranosyl, 2-(1-α-L-rhamnopyranosyl)-3-(1-β-D-glucopyranosyl)-1-β-D-glucopyranosyl, 2-(1-β-D xylopyranosyl)-3-(1-β-D-glucopyranosyl)-1-β-D-glucopyranosyl, 2-(1-β-D-6-deoxy glucopyranosyl)-3-(1-β-D-glucopyranosyl)-1-β-D-glucopyranosyl, and 2,3,6,-tris(1-β-D-glucopyranosyl)-1-β-D-glucopyranosyl. In some other such embodiments, —$X^2$—$R^2$ is a moiety selected from the group consisting of: a hydrogen atom, 1-β-D-glucopyranosyl, 2-(1-β-D-glucopyranosyl)-1-β-D-glucopyranosyl, 3-(1-β-D-glucopyranosyl)-1-β-D-glucopyranosyl, 6-(1-β-D-glucopyranosyl)-1-β-D-glucopyranosyl, 2-(1-α-D-glucopyranosyl)-1-β-D-glucopyranosyl, 3-(1-α-D-glucopyranosyl)-1-β-D-glucopyranosyl, 6-(1-α-D-glucopyranosyl)-1-β-D-glucopyranosyl, 2-(1-α-L-rhamnopyranosyl))-1-β-D-glucopyranosyl, 2-(1-β-D-xylopyranosyl)-1-β-D-glucopyranosyl, 6-(1-β-D-xylopyranosyl)-1-β-D-glucopyranosyl, 2-(1-β-D-6-deoxy glucopyranosyl)-1-β-D-glucopyranosyl, 2-(1-α-L-arabinopyranosyl))-1-β-D-glucopyranosyl, 6-(1-α-L-arabinopyranosyl))-1-β-D-glucopyranosyl, 2-(1-β-D-galactopyranosyl))-1-β-D-glucopyranosyl, 6-(1-β-D-galactopyranosyl))-1-β-D-glucopyranosyl, 2,3-bis(1-β-D-glucopyranosyl)-1-β-D-glucopyranosyl, 2,6-bis(1-β-D-glucopyranosyl)-1-β-D-glucopyranosyl, 2-(1-α-L-rhamnopyranosyl)-3-(1-β-D-glucopyranosyl)-1-β-D-glucopyranosyl, 2-(1-β-D-xylopyranosyl)-3-(1-β-D-glucopyranosyl)-1-β-D-glucopyranosyl, 2-(1-β-D-6-deoxy glucopyranosyl)-3-(1-β-D-glucopyranosyl)-1-β-D-glucopyranosyl, and 2,3,6,-tris(1-β-D-glucopyranosyl)-1-β-D-glucopyranosyl.

In some embodiments of any of the foregoing embodiments, one of —$X^1$—$R^1$ or —$X^2$—$R^2$ is a moiety selected from the group consisting of: 1-β-D-6-O-malonyl glucopyranosyl, 2-(1-β-D-6-O-malonyl glucopyranosyl)-1-β-D-glucopyranosyl, 2-(1-β-D-glucopyranosyl)-1-β-D-6-O-malonyl glucopyranosyl, 3-(1-β-D-6-O-malonyl glucopyranosyl)-1-β-D-glucopyranosyl, 3-(1-β-D-glucopyranosyl)-1-β-D-6-O-malonyl glucopyranosyl, 6-(1-β-D-6-O-malonyl glucopyranosyl)-1-β-D-glucopyranosyl, 6-(1-β-D-glucopyranosyl)-1-β-D-6-O-malonyl glucopyranosyl, 2-(1-α-L-rhamnopyranosyl))-1-β-D-6-O-malonyl glucopyranosyl, 2-(1-β-D-xylopyranosyl)-1-β-D-6-O-malonyl glucopyranosyl, 2,3-bis(1-β-D-glucopyranosyl)-1-β-D-6-O-malonyl glucopyranosyl, 2-(1-β-D-6-O-malonyl glucopyranosyl)-3-(1-β-D-glucopyranosyl)-1-β-D-glucopyranosyl, 2-(1-β-D-glucopyranosyl)-3-(1-β-D-6-O-malonyl glucopyranosyl)-1-β-D-glucopyranosyl, 2-(1-α-L-rhamnopyranosyl)-3-(1-β-D-6-O-malonyl glucopyranosyl)-1-β-D-glucopyranosyl, 2-(1-α-L-rhamnopyranosyl)-3-(1-β-D-glucopyranosyl)-1-β-D-6-O-malonyl glucopyranosyl, 2-(1-β-D-xylopyranosyl)-3-(1-β-D-6-O-malonyl glucopyranosyl)-1-β-D-glucopyranosyl, 2-(1-β-D-xylopyranosyl)-3-(1-β-D-glucopyranosyl)-1-β-D-6-O-malonyl glucopyranosyl, 2-(1-β-D-6-deoxy glucopyranosyl)-3-(1-β-D-6-O-malonyl glucopyranosyl)-1-β-D-glucopyranosyl, 2-(1-β-D-6-deoxy glucopyranosyl)-3-(1-β-D-glucopyranosyl)-1-β-D-6-O-malonyl glucopyranosyl, 2,3,6,-tris(1-β-D-glucopyranosyl)-1-β-D-6-O-malonyl glucopyranosyl, 2-(1-β-D-6-O-malonyl glucopyranosyl)-3,6,bis-(1-β-D-glucopyranosyl)-1-β-D-glucopyranosyl, 2,6-bis(1-β-D-glucopyranosyl)-3-(1-β-D-6-malonyl glucopyranosyl)-1-β-D-glucopyranosyl, and 2,3-bis(1-β-D-glucopyranosyl)-6-(1-β-D-6-malonyl glucopyranosyl)-1-β-D-glucopyranosyl. In some such embodiments —$X^1$—$R^1$ is a moiety selected from the group consisting of 1-β-D-6-O-malonyl glucopyranosyl, 2-(1-β-D-6-O-malonyl glucopyranosyl)-1-β-D-glucopyranosyl, 2-(1-β-D-glucopyranosyl)-1-β-D-6-O-malonyl glucopyranosyl, 3-(1-β-D-6-O-malonyl glucopyranosyl)-1-β-D-glucopyranosyl, 3-(1-β-D-glucopyranosyl)-1-β-D-6-O-malonyl glucopyranosyl, 6-(1-β-D-6-O-malonyl glucopyranosyl)-1-β-D-glucopyranosyl, 6-(1-β-D-glucopyranosyl)-1-β-D-6-O-malonyl glucopyranosyl, 2-(1-α-L-rhamnopyranosyl))-1-β-D-6-O-malonyl glucopyranosyl, 2-(1-β-D-xylopyranosyl)-1-β-D-6-O-malonyl glucopyranosyl, 2,3-bis(1-β-D-glucopyranosyl)-1-β-D-6-O-malonyl glucopyranosyl, 2-(1-β-D-6-O-malonyl glucopyranosyl)-3-(1-β-D-glucopyranosyl)-1-β-D-glucopyranosyl, 2-(1-β-D-glucopyranosyl)-3-(1-β-D-6-O-malonyl glucopyranosyl)-1-β-D-glucopyranosyl, 2-(1-α-L-rhamnopyranosyl)-3-(1-β-D-6-O-malonyl glucopyranosyl)-1-β-D-glucopyranosyl, 2-(1-α-L-rhamnopyranosyl)-3-(1-β-D-glucopyranosyl)-1-β-D-6-O-malonyl glucopyranosyl, 2-(1-β-D-xylopyranosyl)-3-(1-β-D-6-O-malonyl glucopyranosyl)-1-β-D-glucopyranosyl, 2-(1-β-D-xylopyranosyl)-3-(1-β-D-glucopyranosyl)-1-β-D-6-O-malonyl glucopyranosyl, 2-(1-β-D-6-deoxy glucopyranosyl)-3-(1-β-D-6-O-malonyl glucopyranosyl)-1-β-D-glucopyranosyl, 2-(1-β-D-6-deoxy glucopyranosyl)-3-(1-β-D-glucopyranosyl)-1-β-D-6-O-malonyl glucopyranosyl, 2,3,6,-tris(1-β-D-glucopyranosyl)-1-β-D-6-O-malonyl glucopyranosyl, 2-(1-β-D-6-O-malonyl glucopyranosyl)-3,6,bis-(β-D-glucopyranosyl)-1-β-D-glucopyranosyl, 2,6-bis(1-β-D-glucopyranosyl)-3-(1-β-D-6-malonyl glucopyranosyl)-1-β-D-glucopyranosyl, and 2,3-bis(1-β-D-glucopyranosyl)-6-(1-β-D-6-malonyl glucopyranosyl)-1-β-D-glucopyranosyl. In some other such embodiments —$X^2$—$R^2$ is a moiety selected from the group consisting of: 1-β-D-6-O-malonyl glucopyranosyl, 2-(1-β-D-6-O-malonyl glucopyranosyl)-1-β-D-glucopyranosyl, 2-(1-β-D-glucopyranosyl)-1-β-D-6-O-malonyl glucopyranosyl, 3-(1-β-D-6-O-malonyl glucopyranosyl)-1-β-D-glucopyranosyl, 3-(1-β-D-glucopyranosyl)-1-β-D-6-O-malonyl glucopyranosyl, 6-(1-β-D-6-O-malonyl glucopyranosyl)-1-β-D-glucopyranosyl, 6-(1-β-D-glucopyranosyl)-1-β-D-6-O-malonyl glucopyranosyl, 2-(1-α-L-rhamnopyranosyl))-1-β-D-6-O-malonyl glucopyranosyl, 2-(1-β-D-xylopyranosyl)-1-β-D-6-O-malonyl glucopyranosyl, 2,3-bis(1-β-D-glucopyranosyl)-1-β-D-6-O-malonyl glucopyranosyl, 2-(1-β-D-6-O-malonyl glucopyranosyl)-3-(1-β-D-glucopyranosyl)-1-β-D-glucopyranosyl, 2-(1-β-D-glucopyranosyl)-3-(1-β-D-6-O-malonyl glucopyranosyl)-1-β-D-glucopyranosyl, 2-(1-α-L-rhamnopyranosyl)-3-(1-β-D-6-O-malonyl glucopyranosyl)-1-β-D-glucopyranosyl, 2-(1-α-L-rhamnopyranosyl)-3-(1-β-D-glucopyranosyl)-1-β-D-6-O-malonyl glucopyranosyl, 2-(1-β-D-xylopyranosyl)-3-(1-β-D-6-O-malonyl glucopyranosyl)-1-β-D-glucopyranosyl, 2-(1-β-D-xylopyranosyl)-3-(1-β-D-glucopyranosyl)-1-β-D-6-O-malonyl glucopyranosyl, 2-(1-β-D-6-deoxy glucopyranosyl)-3-(1-β-D-6-O-malonyl glucopyranosyl)-1-β-D-glucopyranosyl, 2-(β-D-6-deoxy glucopyranosyl)-3-(1-β-D-glucopyranosyl)-1-β-D-6-O-malonyl glucopyranosyl, 2,3,6,-tris(1-β-D-glucopyranosyl)-1-β-D-6-O-malonyl glucopyranosyl, 2-(1-β-D-6-O-malonyl glucopyranosyl)-3,6,bis-(1-β-D-glucopyranosyl)-1-β-D-glucopyranosyl, 2,6-bis(1-β-D-glucopyranosyl)-3-(1-β-D-6-malonyl glucopyranosyl)-1-β-D-glucopyranosyl, and 2,3-bis(1-β-D-glucopyranosyl)-6-(1-β-D-6-malonyl glucopyranosyl)-1-β-D-glucopyranosyl.

In some embodiments of any of the foregoing embodiments, the taste-modifying compounds of the present aspect (for example, compounds of formula (I)) are: 6-O-malonyl Rebaudioside A, 6-O-malonyl Stevioside, 6-O-malonyl Rebaudioside C, 6-O-malonyl Rebaudioside D, 6-O-malonyl Rebaudioside E, 6-O-malonyl Rebaudioside M, 6-O-malonyl Rebaudioside I, 6-O-malonyl Rebaudioside F, 6-O-malonyl Rebaudioside B, 6-O-malonyl Rebaudioside C acid, 6-O-malonyl Rubusoside, 6-O-malonyl steviol monoside, 6-O-malonyl Rebaudioside G, 6-O-malonyl steviol dioside, 6-O-malonyl dulcoside A, or any combination thereof.

Table 1 sets forth several additional examples of taste-modifying compounds of the present disclosure. In some embodiments, the taste-modifying compounds comprise Compound 101. In some embodiments, the taste-modifying compounds comprise Compound 102. In some embodiments, the taste-modifying compounds comprise Compound 103. In some embodiments, the taste-modifying compounds comprise Compound 104. In some embodiments, the taste-modifying compounds comprise Compound 105. In some embodiments, the taste-modifying compounds comprise Compound 106.

TABLE 1

| No. | Structure |
|---|---|
| 101 | 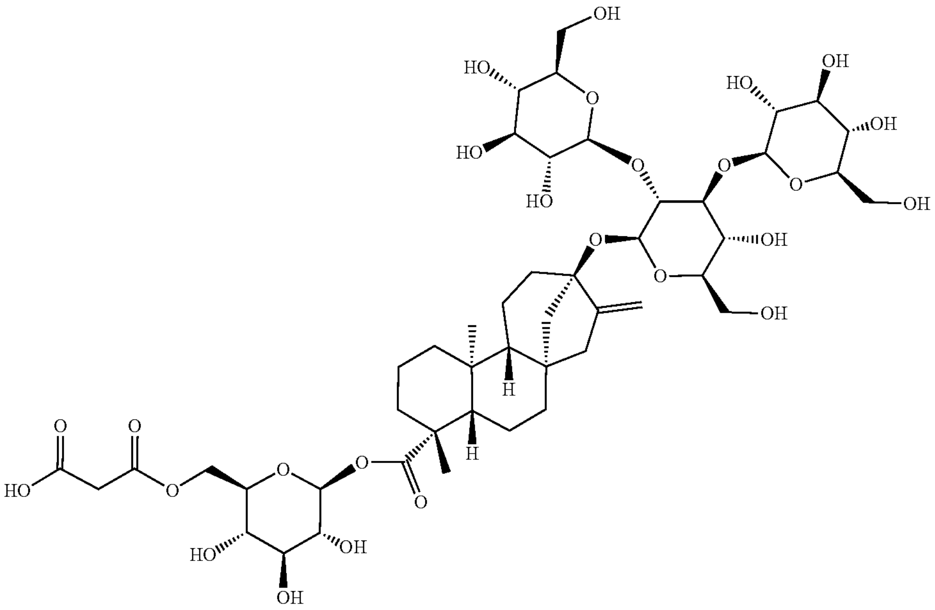 |
| 102 | 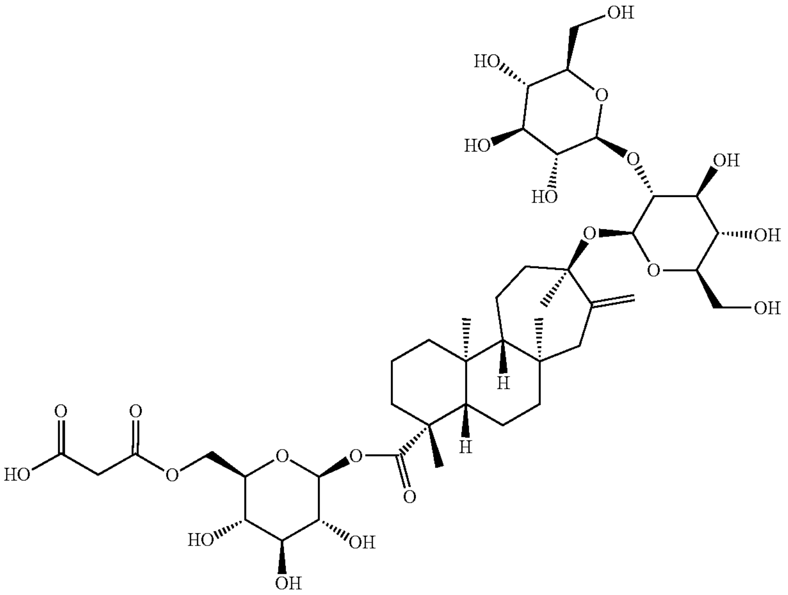 |

TABLE 1-continued
| No. | Structure |
| --- | --- |
| 103 | 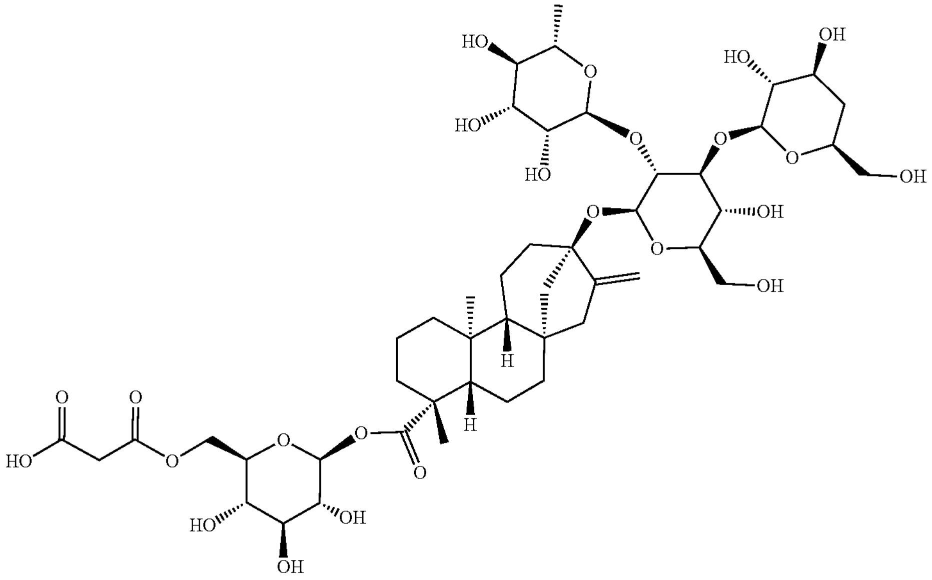 |
| 104 | 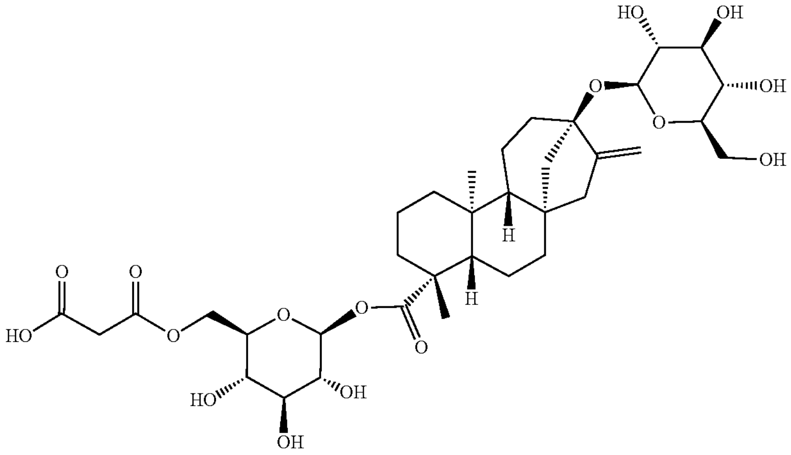 |

TABLE 1-continued
| No. | Structure |
| --- | --- |
| 105 | 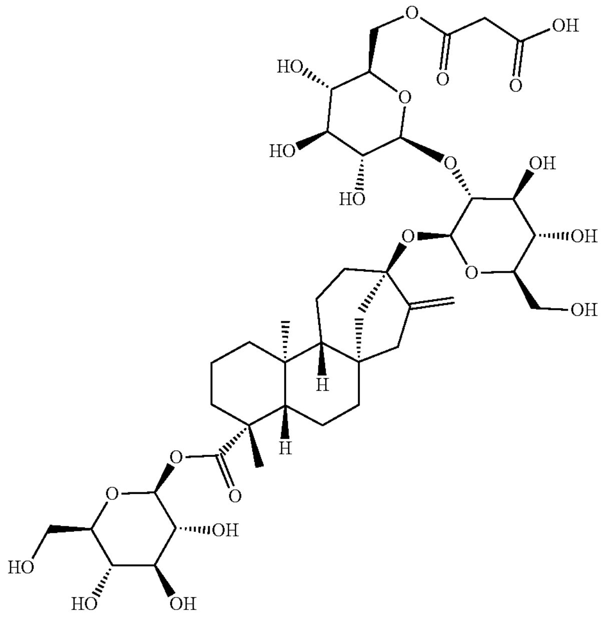 |
| 106 | 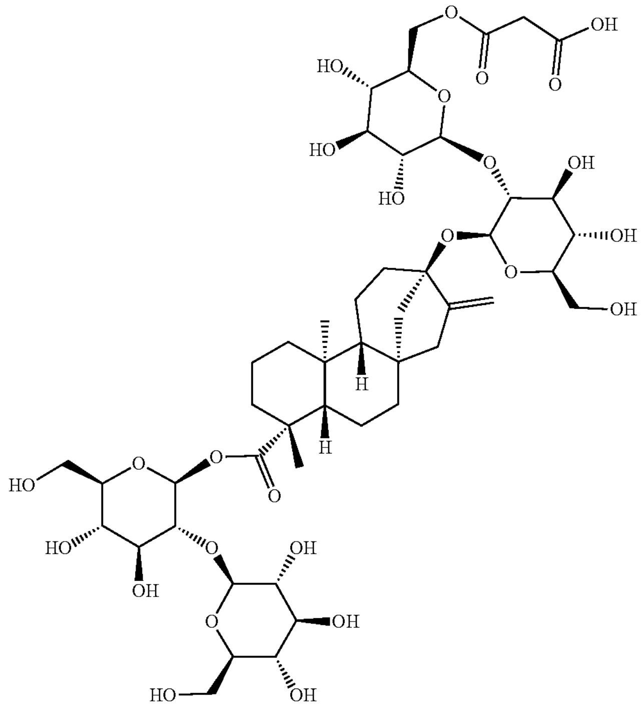 |

TABLE 1-continued

| No. | Structure |
| --- | --- |
| 107 | 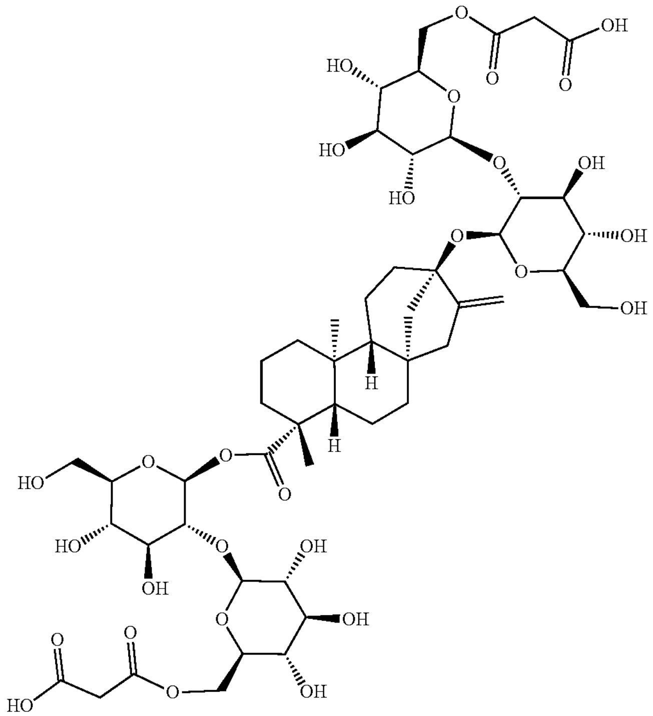 |

Where the compounds disclosed herein have at least one chiral center, they may exist as individual enantiomers and diastereomers or as mixtures of such isomers. In some embodiments in connection with the second aspect, the sweet-enhancing compound has substantial enantiomeric purity.

Separation of the individual isomers or selective synthesis of the individual isomers is accomplished by application of various methods which are well known to practitioners in the art. Unless otherwise indicated (e.g., where the stereochemistry of a chiral center is explicitly shown), all such isomers and mixtures thereof are included in the scope of the compounds disclosed herein. Furthermore, compounds disclosed herein may exist in one or more crystalline or amorphous forms. Unless otherwise indicated, all such forms are included in the scope of the compounds disclosed herein including any polymorphic forms. In addition, some of the compounds disclosed herein may form solvates with water (i.e., hydrates) or common organic solvents. Unless otherwise indicated, such solvates are included in the scope of the compounds disclosed herein.

The skilled artisan will recognize that some structures described herein may be resonance forms or tautomers of compounds that may be fairly represented by other chemical structures, even when kinetically; the artisan recognizes that such structures may only represent a very small portion of a sample of such compound(s). Such compounds are considered within the scope of the structures depicted, though such resonance forms or tautomers are not represented herein.

Isotopes may be present in the compounds described. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise.

In some embodiments, the compounds disclosed herein are capable of forming acid and/or base salts by virtue of the presence of amino and/or carboxyl groups or groups similar thereto. Physiologically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Physiologically acceptable salts can be formed using inorganic and organic bases. Inorganic bases from which salts can be derived include, for example, bases that contain sodium, potassium, lithium, ammonium, calcium, magnesium, iron, zinc, copper, manganese, aluminum, and the like; particularly preferred are the ammonium, potassium, sodium, calcium and magnesium salts. In some embodiments, treatment of the compounds disclosed herein with an inorganic base results in loss of a labile hydrogen from the compound to afford the salt form including an inorganic cation such as $Li^+$, $Na^+$, $K^+$, $Mg^{2+}$ and $Ca^{2+}$ and the like. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. In some embodiments, the salts are comestibly acceptable salts, which are salts suitable for inclusion in comestible food and/or beverage products.

Solid State Forms and Solutions of Flavor-Modifying Compounds

In another aspect, the disclosure provides various solid-state forms of the malonyl steviol glycosides.

In some embodiments, the malonyl steviol glycosides exists as a crystalline solid, either in substantially pure form or in a formulation such as those set forth below. The crystalline solid can have any suitable polymorphic form, such as any polymorphic form obtainable via recrystallization in any suitable solvent system, according to techniques commonly used in the art of polymorph screening.

In some other embodiments, the malonyl steviol glycosides exist as an amorphous solid or a semi-amorphous solid, meaning that it lacks any regular crystalline structure. Such solids can be generated using standard techniques, such as spray drying, and the like.

In some embodiments, the malonyl steviol glycosides exist as a solvate, which is a pseudomorphic form of the compound in which one or more solvent molecules (such as water molecules) are taken up into the crystalline structure. Any suitable solvent or combination of solvents can be used, including, but not limited to, water, methanol, ethanol, n-propanol, isopropanol, n-butanol, 2-butanol, isobutanol, ethyl acetate, ethylene glycol, 1,2-propylene glycol, 1,3-propylene glycol, and the like. In some embodiments, the disclosure provides hydrates of the Malonyl steviol glycosides or its comestibly acceptable salts. Such solvates can be generated by any suitable means, such as those techniques typically used by skilled artisans in the field of polymorph and solvate screening.

In some other embodiments, the malonyl steviol glycosides exist as a co-crystal with one or more other compounds, such as one or more other sweetener compounds. The malonyl steviol glycosides can form a co-crystal with any suitable compound. Non-limiting examples of such suitable compounds include fructose, glucose, galactose, sucrose, lactose, maltose, allulose, sugar alcohols (such as erythritol, sorbitol, xylitol, and the like), sucralose, steviol glycosides (such as rebaudioside A, rebaudioside E, rebaudioside M, and the like natural stevioside compounds), mogrosides (such as mogroside V, and other like natural mogroside compounds), aspartame, saccharin, acesulfame K, cyclamate, inulin, isomalt, and maltitol. Such co-crystals can be generated by any suitable means, such as those set forth in U.S. Patent Application Publication No. 2018/0363074, which is incorporated herein by reference.

In some embodiments, the malonyl steviol glycosides are in the form of a dry particle. Such dry particles can be formed by standard techniques in the art, such as dry granulation, wet granulation, and the like. Such particles can also contain a number of excipients, including, inert diluents, such as calcium carbonate, sodium carbonate, lactose, calcium phosphate, and sodium phosphate; granulating and disintegrating agents, such as starch, cellulosic materials, and alginic acid; binding agents, such as gelatin, guar gum, and acacia; and lubricating agents, such as magnesium stearate, stearic acid, and talc. Other excipients typically used in food and beverage products can also be included, such as typical foodstuff materials.

In some embodiments, the malonyl steviol glycosides are in the form of a liquid solution or a liquid suspension. Such compositions can also include: carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide such as lecithin, or condensation products of an alkylene oxide with fatty acids, for example polyoxyethylene stearate, or condensation products of ethylene oxide with long chain aliphatic alcohols, for example, heptadecaethyl-eneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. Such compositions can also include one or more coloring agents, one or more flavoring agents, and the like. Such liquid suspensions and solutions have a liquid carrier. In general, the liquid carrier comprises water. In some such cases, the liquid composition is an emulsion, such as an oil-in-water or a water-in-oil emulsion. Further, in some cases, water may be too polar to dissolve the Malonyl steviol glycosides to the desired concentration. In such instances, it can be desirable to introduce water-miscible solvents, such as alcohols, glycols, polyols, and the like, to the solvent to enhance solubilization of the Malonyl steviol glycosides.

In some embodiments, the malonyl steviol glycosides are in the form of a solution, i.e., are solvated within a liquid carrier. In some embodiments, the liquid carrier is an aqueous carrier. In some such embodiments, the solutions comprise a comestibly acceptable salt of TM1, such as a hydrochloride sale, a potassium salt, or a sodium salt. Such solutions can be diluted to any suitable concentration.

Formulations, Uses, and Methods

In other aspects, the disclosure provides formulations, uses, and methods of using the malonyl steviol glycosides. In another aspect, the disclosure provides a comestible composition comprises the malonyl steviol glycosides. In other aspects, the disclosure provides uses of the malonyl steviol glycosides to sweeten a comestible composition. In other aspects, the disclosure provides uses of the malonyl steviol glycosides to reduce the bitterness of a comestible composition. In other aspects, the disclosure provides uses of the malonyl steviol glycosides to enhance the sweetness of the comestible composition. In some embodiments thereof, the comestible composition comprises a another sweetener (according to any of the embodiments set forth below). In other aspects, the disclosure provides uses of the malonyl steviol glycosides to enhance the umami taste of a comestible composition. In other aspects, the disclosure provides uses of the malonyl steviol glycosides to reduce the sourness of a comestible composition.

The disclosure also provides methods that correspond to each of the foregoing uses. Thus, in certain related aspects, the disclosure provides methods of enhancing the sweetness of a comestible composition, comprising introducing an amount (such as a sweetness-enhancing effective amount) of the malonyl steviol glycosides to the comestible composition. In some other related aspects, the disclosure provides methods of sweetening a comestible composition, comprising introducing an amount (such as a sweetening effective amount) of the malonyl steviol glycosides to the comestible composition. In some other related aspects, the disclosure provides methods of reducing the bitterness of a comestible composition, comprising introducing an amount (such as a bitterness-reducing effective amount) of the malonyl steviol glycosides to the comestible composition.

The foregoing uses and methods generally involve the use of the malonyl steviol glycosides in a composition containing one or more additional ingredients. For example, in at least one aspect, the disclosure provides compositions comprising the malonyl steviol glycosides wherein the malonyl steviol glycosides makes up at least 1% by weight, or at least 2% by weight, or at least 3% by weight, or at least 5% by weight, or at least 10% by weight, or at least 20% by weight, or at least 30% by weight, or at least 40% by weight, of the compositions on a dry weight basis (e.g., based on the total weight of the composition excluding the weight of any liquid carrier). In a related aspect, the disclosure provides solid-state compositions comprising the malonyl steviol glycosides wherein the malonyl steviol glycosides make up at least 1% by weight, or at least 2% by weight, or at least 3% by weight, or at least 5% by weight, or at least 10% by weight, or at least 20% by weight, or at least 30% by weight, or at least 40% by weight, of the solid-state compositions, based on the total weight of composition. In another related aspect, the disclosure provides comestible compositions comprising the malonyl steviol glycosides wherein the concentration of the malonyl steviol glycosides in the comestible compositions is at least 10 ppm, or at least 15 ppm, or at least 20 ppm, or at least 25 ppm, or at least 30 ppm, or at least 40 ppm, or at least 50 ppm, or at least 75 ppm, or at least 100 ppm, or at least 150 ppm, or at least 200 ppm, or at least 250 ppm, or at least 300 ppm. In another related aspect, the disclosure provides comestible compositions comprising the malonyl steviol glycosides wherein the comestible compositions comprise another sweetener, such as sucrose, fructose, xylitol, erythritol, allulose, glucose, or combinations thereof. In another related aspect, the disclosure provides a concentrated sweetening composition comprising any malonyl steviol glycosides of the foregoing aspects, including any embodiments or combination of embodiments thereof, as set forth above, and, optionally, another sweetener.

In certain particular embodiments, the comestible composition comprises sucrose and the malonyl steviol glycosides. In some such embodiments, the introduction of the malonyl steviol glycosides permits one to use less sucrose (such as more than 10% less, more than 20% less, more than 30% less, more than 40% less, more than 50% less, more than 60% less, or more than 70% less) and still achieve a level of sweetness characteristic of a comparable product that employs more sucrose. In some embodiments, the concentration of the malonyl steviol glycosides is no more than 1000 ppm, or no more than 900 ppm, or no more than 800 ppm, or no more than 700 ppm, or no more than 600 ppm, or no more than 500 ppm, or no more than 400 ppm, or no more than 300 ppm, or no more than 200 ppm, or no more than 100 ppm, or no more than 50 ppm, or no more than 25 ppm, or no more than 10 ppm. In some further such embodiments, the concentration of the malonyl steviol glycosides is at least 5 ppm. Such comestible compositions can be in any suitable form. In some embodiments, the comestible composition is a food product, such as any of those specifically listed below. In other embodiments, the comestible composition is a beverage product, such as a soda, and the like. The sucrose can be introduced in any suitable form, such as natural syrups (cane syrup) and the like.

In certain particular embodiments, the comestible composition comprises fructose and the malonyl steviol glycosides. In some such embodiments, the introduction of the malonyl steviol glycosides permits one to use less fructose (such as more than 10% less, more than 20% less, more than 30% less, more than 40% less, more than 50% less, more than 60% less, or more than 70% less) and still achieve a level of sweetness characteristic of a comparable product that employs more fructose. In some embodiments, the concentration of the malonyl steviol glycosides is no more than 1000 ppm, or no more than 900 ppm, or no more than 800 ppm, or no more than 700 ppm, or no more than 600 ppm, or no more than 500 ppm, or no more than 400 ppm, or no more than 300 ppm, or no more than 200 ppm, or no more than 100 ppm, or no more than 50 ppm, or no more than 25 ppm, or no more than 10 ppm. In some further such embodiments, the concentration of the malonyl steviol glycosides is at least 5 ppm. In some embodiments, the comestible composition is a food product, such as any of those specifically listed below. In other embodiments, the comestible composition is a beverage product, such as a soda, and the like. The fructose can be supplied in any suitable form, such as natural syrups, high-fructose corn syrup, and the like.

In certain particular embodiments, the comestible composition comprises high-fructose corn syrup and the malonyl steviol glycosides. In some such embodiments, the introduction of the malonyl steviol glycosides permits one to use less high-fructose corn syrup (such as more than 10% less, more than 20% less, more than 30% less, more than 40% less, more than 50% less, more than 60% less, or more than 70% less) and still achieve a level of sweetness characteristic of a comparable product that employs more high-fructose corn syrup. In some embodiments, the concentration of the malonyl steviol glycosides is no more than 1000 ppm, or no more than 900 ppm, or no more than 800 ppm, or no more than 700 ppm, or no more than 600 ppm, or no more than 500 ppm, or no more than 400 ppm, or no more than 300 ppm, or no more than 200 ppm, or no more than 100 ppm, or no more than 50 ppm, or no more than 25 ppm, or no more than 10 ppm. In some further such embodiments, the concentration of the malonyl steviol glycosides is at least 5 ppm. In some embodiments, the comestible composition is a food product, such as any of those specifically listed below. In other embodiments, the comestible composition is a beverage product, such as a soda, and the like.

In certain particular embodiments, the comestible composition comprises glucose (for example, D-glucose, in either its alpha or beta forms, or a combination thereof) and the malonyl steviol glycosides. In some such embodiments, the introduction of the malonyl steviol glycosides permits one to use less glucose (such as more than 10% less, more than 20% less, more than 30% less, more than 40% less, more than 50% less, more than 60% less, or more than 70% less) and still achieve a level of sweetness characteristic of a comparable product that employs more glucose. In some embodiments, the concentration of the malonyl steviol glycosides is no more than 1000 ppm, or no more than 900 ppm, or no more than 800 ppm, or no more than 700 ppm, or no more than 600 ppm, or no more than 500 ppm, or no more than 400 ppm, or no more than 300 ppm, or no more than 200 ppm, or no more than 100 ppm, or no more than 50 ppm, or no more than 25 ppm, or no more than 10 ppm. In some further such embodiments, the concentration of the malonyl steviol glycosides is at least 5 ppm. Such comestible compositions can be in any suitable form. In some embodiments, the comestible composition is a food product, such as any of those specifically listed below. In other embodiments, the comestible composition is a beverage product, such as a soda, and the like. The glucose can be introduced in any suitable form, such as natural syrups and the like.

In certain particular embodiments, the comestible composition comprises sucralose and the malonyl steviol glycosides. In some such embodiments, the introduction of the malonyl steviol glycosides permits one to use less sucralose (such as more than 10% less, more than 20% less, more than 30% less, more than 40% less, more than 50% less, more than 60% less, or more than 70% less) and still achieve a level of sweetness characteristic of a comparable product that employs more sucralose. In some embodiments, the concentration of the malonyl steviol glycosides is no more than 1000 ppm, or no more than 900 ppm, or no more than 800 ppm, or no more than 700 ppm, or no more than 600 ppm, or no more than 500 ppm, or no more than 400 ppm, or no more than 300 ppm, or no more than 200 ppm, or no more than 100 ppm, or no more than 50 ppm, or no more than 25 ppm, or no more than 10 ppm. In some further such embodiments, the concentration of the malonyl steviol glycosides is at least 5 ppm. Such comestible compositions can be in any suitable form. In some embodiments, the comestible composition is a food product, such as any of those specifically listed below. In other embodiments, the comestible composition is a beverage product, such as a soda, and the like.

In certain particular embodiments, the comestible composition comprises rebaudiosides (such as rebaudioside A, rebaudioside D, rebaudioside E, rebaudioside M, or any combination thereof) and the malonyl steviol glycosides. In some such embodiments, the introduction of the malonyl steviol glycosides permits one to use less rebaudioside (such as more than 10% less, more than 20% less, more than 30% less, more than 40% less, more than 50% less, more than 60% less, or more than 70% less) and still achieve a level of sweetness characteristic of a comparable product that employs more rebaudioside. In some embodiments, the concentration of the malonyl steviol glycosides is no more than 1000 ppm, or no more than 900 ppm, or no more than 800 ppm, or no more than 700 ppm, or no more than 600 ppm, or no more than 500 ppm, or no more than 400 ppm, or no more than 300 ppm, or no more than 200 ppm, or no more than 100 ppm, or no more than 50 ppm, or no more than 25 ppm, or no more than 10 ppm. In some further such embodiments, the concentration of the malonyl steviol glycosides is at least 5 ppm. Such comestible compositions can be in any suitable form. In some embodiments, the comestible composition is a food product, such as any of those specifically listed below. In other embodiments, the comestible composition is a beverage product, such as a soda, and the like.

In certain particular embodiments, the comestible composition comprises acefulfame K and the malonyl steviol glycosides. In some such embodiments, the introduction of the malonyl steviol glycosides permits one to use less acesulfame K (such as more than 10% less, more than 20% less, more than 30% less, more than 40% less, more than 50% less, more than 60% less, or more than 70% less) and still achieve a level of sweetness characteristic of a comparable product that employs more acesulfame K. In some embodiments, the concentration of the malonyl steviol glycosides is no more than 1000 ppm, or no more than 900 ppm, or no more than 800 ppm, or no more than 700 ppm, or no more than 600 ppm, or no more than 500 ppm, or no more than 400 ppm, or no more than 300 ppm, or no more than 200 ppm, or no more than 100 ppm, or no more than 50 ppm, or no more than 25 ppm, or no more than 10 ppm. In some further such embodiments, the concentration of the malonyl steviol glycosides is at least 5 ppm. Such comestible compositions can be in any suitable form. In some embodiments, the comestible composition is a food product, such as any of those specifically listed below. In other embodiments, the comestible composition is a beverage product, such as a soda, and the like.

In certain particular embodiments, the comestible composition comprises allulose and the malonyl steviol glycosides. In some such embodiments, the introduction of the malonyl steviol glycosides permits one to use less allulose (such as more than 10% less, more than 20% less, more than 30% less, more than 40% less, more than 50% less, more than 60% less, or more than 70% less) and still achieve a level of sweetness characteristic of a comparable product that employs more allulose. In some embodiments, the concentration of the malonyl steviol glycosides is no more than 1000 ppm, or no more than 900 ppm, or no more than 800 ppm, or no more than 700 ppm, or no more than 600 ppm, or no more than 500 ppm, or no more than 400 ppm, or no more than 300 ppm, or no more than 200 ppm, or no more than 100 ppm, or no more than 50 ppm, or no more than 25 ppm, or no more than 10 ppm. In some further such embodiments, the concentration of the malonyl steviol glycosides is at least 5 ppm. Such comestible compositions can be in any suitable form. In some embodiments, the comestible composition is a food product, such as any of those specifically listed below. In some particular embodiments, the comestible composition is a protein bar or a meal replacement bar. In other embodiments, the comestible composition is a beverage product, such as a soda, and the like.

In certain particular embodiments, the comestible composition comprises erythritol and the malonyl steviol glycosides. In some such embodiments, the introduction of the malonyl steviol glycosides permits one to use less erythritol (such as more than 10% less, more than 20% less, more than 30% less, more than 40% less, more than 50% less, more than 60% less, or more than 70% less) and still achieve a level of sweetness characteristic of a comparable product that employs more erythritol. In some embodiments, the concentration of the malonyl steviol glycosides is no more than 1000 ppm, or no more than 900 ppm, or no more than 800 ppm, or no more than 700 ppm, or no more than 600 ppm, or no more than 500 ppm, or no more than 400 ppm, or no more than 300 ppm, or no more than 200 ppm, or no more than 100 ppm, or no more than 50 ppm, or no more than 25 ppm, or no more than 10 ppm. In some further such embodiments, the concentration of the malonyl steviol glycosides is at least 5 ppm. Such comestible compositions can be in any suitable form. In some embodiments, the comestible composition is a food product, such as any of those specifically listed below. In other embodiments, the comestible composition is a beverage product, such as a soda, and the like.

In certain particular embodiments, the comestible composition comprises aspartame and the malonyl steviol glycosides. In some such embodiments, the introduction of the malonyl steviol glycosides permits one to use less aspartame (such as more than 10% less, more than 20% less, more than 30% less, more than 40% less, more than 50% less, more than 60% less, or more than 70% less) and still achieve a level of sweetness characteristic of a comparable product that employs more aspartame. In some embodiments, the concentration of the malonyl steviol glycosides is no more than 1000 ppm, or no more than 900 ppm, or no more than 800 ppm, or no more than 700 ppm, or no more than 600 ppm, or no more than 500 ppm, or no more than 400 ppm, or no more than 300 ppm, or no more than 200 ppm, or no more than 100 ppm, or no more than 50 ppm, or no more than 25 ppm, or no more than 10 ppm. In some further such embodiments, the concentration of the malonyl steviol glycosides is at least 5 ppm. Such comestible compositions can be in any suitable form. In some embodiments, the comestible composition is a food product, such as any of those specifically listed below. In other embodiments, the comestible composition is a beverage product, such as a soda, and the like.

In certain particular embodiments, the comestible composition comprises cyclamate and the malonyl steviol glycosides. In some such embodiments, the introduction of the malonyl steviol glycosides permits one to use less cyclamate (such as more than 10% less, more than 20% less, more than 30% less, more than 40% less, more than 50% less, more than 60% less, or more than 70% less) and still achieve a level of sweetness characteristic of a comparable product that employs more cyclamate. In some embodiments, the concentration of the malonyl steviol glycosides is no more than 1000 ppm, or no more than 900 ppm, or no more than 800 ppm, or no more than 700 ppm, or no more than 600 ppm, or no more than 500 ppm, or no more than 400 ppm, or no more than 300 ppm, or no more than 200 ppm, or no more than 100 ppm, or no more than 50 ppm, or no more than 25 ppm, or no more than 10 ppm. In some further such embodiments, the concentration of the malonyl steviol glycosides is at least 5 ppm. Such comestible compositions can be in any suitable form. In some embodiments, the comestible composition is a food product, such as any of those specifically listed below. In other embodiments, the comestible composition is a beverage product, such as a soda, and the like.

In certain particular embodiments, the comestible composition comprises another mogroside (such as mogroside III, mogroside IV, mogroside V, siamenoside I, isomogroside V, mogroside $IV_E$, isomogroside IV, mogroside $III_E$, 11-oxomogroside V, the 1,6-α isomer of siamenoside I, and any combinations thereof) and the malonyl steviol glycosides. In some such embodiments, the introduction of the malonyl steviol glycosides permits one to use less of another mogroside (such as more than 10% less, more than 20% less, more than 30% less, more than 40% less, more than 50% less, more than 60% less, or more than 70% less) and still achieve a level of sweetness characteristic of a comparable product that employs more of the other mogroside. In some embodiments, the concentration of the malonyl steviol glycosides is no more than 1000 ppm, or no more than 900 ppm, or no more than 800 ppm, or no more than 700 ppm, or no more than 600 ppm, or no more than 500 ppm, or no more than 400 ppm, or no more than 300 ppm, or no more than 200 ppm, or no more than 100 ppm, or no more than 50 ppm, or no more than 25 ppm, or no more than 10 ppm. In some further such embodiments, the concentration of the malonyl steviol glycosides is at least 5 ppm. Such comestible compositions can be in any suitable form. In some embodiments, the comestible composition is a food product, such as any of those specifically listed below. In other embodiments, the comestible composition is a beverage product, such as a soda, and the like. Additional mogroside compounds that may be suitably used are described in U.S. Patent Application Publication No. 2017/0119032.

In certain embodiments of any aspects and embodiments set forth herein that refer to a comestible composition, the comestible composition is a non-naturally-occurring product, such as a composition specifically manufactured for the production of a flavored product, such as manufactured food or beverage product.

In general, compounds as disclosed and described herein, individually or in combination, can be provided in a composition, such as a comestible composition. In one embodiment, compounds as disclosed and described herein, individually or in combination, can impart a more sugar-like temporal profile or flavor profile to a sweetener composition by combining one or more of the compounds as disclosed and described herein with one or more sweeteners in the sweetener composition. In another embodiment, compounds as disclosed and described herein, individually or in combination, can increase or enhance the sweet taste of a composition by contacting the composition thereof with the compounds as disclosed and described herein to form a modified composition.

Thus, in some embodiments, the compositions set forth in any of the foregoing aspects (including in any uses or methods), comprise the malonyl steviol glycosides. In some embodiments, the composition further comprises a vehicle. In some embodiments, the vehicle is water. In some other embodiments, the vehicle is a bulking agent. In some embodiments, the malonyl steviol glycosides is present at a concentration at or below its sweetness recognition threshold. In some other embodiments, the malonyl steviol glycosides is present at a concentration at or above its sweetness recognition threshold.

In some embodiments, an additional sweetener is present. The additional sweetener can be present in any suitable concentration, depending on factors such as the sweetener's potency as a sweetener, its water solubility, and the like. For example, in some embodiments, the additional sweetener is present in an amount from 0.10% to 12% by weight. In some embodiments, the additional sweetener is present in an amount from 0.2% to 10% by weight. In some embodiments, the additional sweetener is present in an amount from 0.3% to 8% by weight. In some embodiments, the additional sweetener is present in an amount from 0.4% to 6% by weight. In some embodiments, the additional sweetener is present in an amount from 0.5% to 5% by weight. In some embodiments, the additional sweetener is present in an amount from 1% to 2% by weight. In some embodiments, the additional sweetener is present in an amount from 0.1% to 5% by weight. In some embodiments, the additional sweetener is present in an amount from 0.10% to 4% by weight. In some embodiments, the additional sweetener is present in an amount from 0.10% to 3% by weight. In some embodiments, the additional sweetener is present in an amount from 0.1% to 2% by weight. In some embodiments, the additional sweetener is present in an amount from 0.1% to 1% by weight. In some embodiments, the additional sweetener is present in an amount from 0.1% to 0.5% by weight. In some embodiments, the additional sweetener is present in an amount from 0.5% to 10% by weight. In some embodiments, the additional sweetener is present in an amount from 2% to 8% by weight. In some further embodiments of the embodiments set forth in this paragraph, the additional sweetener is sucrose, fructose, glucose, xylitol, erythritol, glucose, allulose, or combinations thereof.

In some other embodiments, the additional sweetener is present in an amount from 10 ppm to 1000 ppm. In some embodiments, the additional sweetener is present in an amount from 20 ppm to 800 ppm. In some embodiments, the additional sweetener is present in an amount from 30 ppm to 600 ppm. In some embodiments, the additional sweetener is present in an amount from 40 ppm to 500 ppm. In some embodiments, the additional sweetener is present in an amount from 50 ppm to 400 ppm. In some embodiments, the additional sweetener is present in an amount from 50 ppm to 300 ppm. In some embodiments, the additional sweetener is present in an amount from 50 ppm to 200 ppm. In some embodiments, the additional sweetener is present in an amount from 50 ppm to 150 ppm. In some further embodiments of the embodiments set forth in this paragraph, the additional sweetener is a steviol glycoside, a mogroside, a derivative of either of the foregoing, such as glycoside derivatives (e.g., glucosylates), or any combination thereof.

The compositions can include any suitable sweeteners or combination of sweeteners. In some embodiments, the sweetener is a common saccharide sweeteners, such as sucrose, fructose, glucose, and sweetener compositions comprising natural sugars, such as corn syrup (including high fructose corn syrup) or other syrups or sweetener concentrates derived from natural fruit and vegetable sources. In some embodiments, the sweetener is sucrose, fructose, or a combination thereof. In some embodiments, the sweetener is sucrose. In some other embodiments, the sweetener is selected from rare natural sugars including D-allose, D-psicose, L-ribose, D-tagatose, L-glucose, L-fucose, L-arbinose, D-turanose, and D-leucrose. In some embodiments, the sweetener is selected from semi-synthetic "sugar alcohol" sweeteners such as erythritol, isomalt, lactitol, mannitol, sorbitol, xylitol, maltodextrin, and the like. In some embodiments, the sweetener is selected from artificial sweeteners such as aspartame, saccharin, acesulfame-K, cyclamate, sucralose, and alitame. In some embodiments, the sweetener is selected from the group consisting of cyclamic acid, mogroside, tagatose, maltose, galactose, mannose, sucrose, fructose, lactose, allulose, neotame and other aspartame derivatives, glucose, D-tryptophan, glycine, maltitol, lactitol, isomalt, hydrogenated glucose syrup (HGS), hydrogenated starch hydrolyzate (HSH), stevioside, rebaudioside A, other sweet *Stevia*-based glycosides, chemically modified steviol glycosides (such as glucosylated steviol glycosides), mogrosides, chemically modified mogrosides (such as glucosylated mogrosides), carrelame and other guanidine-based sweeteners. In some embodiments, the additional sweetener is a combination of two or more of the sweeteners set forth in this paragraph. In some embodiments, the sweetener may combinations of two, three, four or five sweeteners as disclosed herein. In some embodiments, the additional sweetener is a sugar. In some embodiments, the additional sweetener is a combination of one or more sugars and other natural and artificial sweeteners. In some embodiments, the additional sweetener is a sugar. In some embodiments, the sugar is cane sugar. In some embodiments, the sugar is beet sugar. In some embodiments, the sugar may be sucrose, fructose, glucose or combinations thereof. In some embodiments, the sugar is sucrose. In some embodiments, the sugar is a combination of fructose and glucose.

In some embodiments, the additional sweeteners can also include, for example, sweetener compositions comprising one or more natural or synthetic carbohydrate, such as corn syrup, high fructose corn syrup, high maltose corn syrup, glucose syrup, sucralose syrup, hydrogenated glucose syrup (HGS), hydrogenated starch hydrolyzate (HSH), or other syrups or sweetener concentrates derived from natural fruit and vegetable sources, or semi-synthetic "sugar alcohol" sweeteners such as polyols. Non-limiting examples of polyols in some embodiments include erythritol, maltitol, mannitol, sorbitol, lactitol, xylitol, isomalt, propylene glycol, glycerol (glycerin), threitol, galactitol, palatinose, reduced isomalto-oligosaccharides, reduced xylo-oligosaccharides, reduced gentio-oligosaccharides, reduced maltose syrup, reduced glucose syrup, isomaltulose, maltodextrin, and the like, and sugar alcohols or any other carbohydrates or combinations thereof capable of being reduced which do not adversely affect taste.

The additional sweetener may be a natural or synthetic sweetener that includes, but is not limited to, agave inulin, agave nectar, agave syrup, amazake, brazzein, brown rice syrup, coconut crystals, coconut sugars, coconut syrup, date sugar, fructans (also referred to as inulin fiber, fructo-oligosaccharides, or oligo-fructose), green *Stevia* powder, *Stevia rebaudiana*, rebaudioside A, rebaudioside B, rebaudioside C, rebaudioside D, rebaudioside E, rebaudioside F, rebaudioside I, rebaudioside H, rebaudioside L, rebaudioside K, rebaudioside J, rebaudioside N, rebaudioside O, rebaudioside M and other sweet *Stevia*-based glycosides, stevioside, stevioside extracts, honey, Jerusalem artichoke syrup, licorice root, luo han guo (fruit, powder, or extracts), lucuma (fruit, powder, or extracts), maple sap (including, for example, sap extracted from *Acer saccharum, Acer nigrum, Acer rubrum, Acer saccharinum, Acer platanoides, Acer negundo, Acer macrophyllum, Acer grandidentatum, Acer glabrum, Acer mono*), maple syrup, maple sugar, walnut sap (including, for example, sap extracted from *Juglans cinerea, Juglans nigra, Juglans ailatifolia, Juglans regia*), birch sap (including, for example, sap extracted from *Betula papyrifera, Betula alleghaniensis, Betula lenta, Betula nigra, Betula populifolia, Betula pendula*), sycamore sap (such as, for example, sap extracted from *Platanus occidentalis*), ironwood sap (such as, for example, sap extracted from *Ostrya virginiana*), mascobado, molasses (such as, for example, blackstrap molasses), molasses sugar, monatin, monellin, cane sugar (also referred to as natural sugar, unrefined cane sugar, or sucrose), palm sugar, panocha, piloncillo, rapadura, raw sugar, rice syrup, sorghum, sorghum syrup, cassava syrup (also referred to as tapioca syrup), thaumatin, yacon root, malt syrup, barley malt syrup, barley malt powder, beet sugar, cane sugar, crystalline juice crystals, caramel, carbitol, carob syrup, castor sugar, hydrogenated starch hydrolates, hydrolyzed can juice, hydrolyzed starch, invert sugar, anethole, arabinogalactan, arrope, syrup, P-4000, acesulfame potassium (also referred to as acesulfame K or ace-K), alitame (also referred to as aclame), advantame, aspartame, baiyunoside, neotame, benzamide derivatives, bemadame, canderel, carrelame and other guanidine-based sweeteners, vegetable fiber, corn sugar, coupling sugars, curculin, cyclamates, cyclocarioside I, demerara, dextran, dextrin, diastatic malt, dulcin, sucrol, valzin, dulcoside A, dulcoside B, emulin, enoxolone, maltodextrin, saccharin, estragole, ethyl maltol, glucin, gluconic acid, glucono-lactone, glucosamine, glucoronic acid, glycerol, glycine, glycyphillin, glycyrrhizin, glycyrrhetic acid monoglucuronide, golden sugar, yellow sugar, golden syrup, granulated sugar, gynostemma, hernandulcin, isomerized liquid sugars, jallab, chicory root dietary fiber, kynurenine derivatives (including N'-formyl-kynurenine, N'-acetyl-kynurenine, 6-chloro-kynurenine), galactitol, litesse, ligicane, lycasin, lugduname, guanidine, falemum, mabinlin I, mabinlin II, maltol, maltisorb, maltodextrin, maltotriol, mannosamine, miraculin, mizuame, mogrosides (including, for example, mogroside IV, mogroside V, and neomogroside), mukurozioside, nano sugar, naringin dihydrochalcone, neohesperidine dihydrochalcone, nib sugar, nigero-oligosaccharide, norbu, orgeat syrup, osladin, pekmez, pentadin, periandrin I, perillaldehyde, perillartine, petphyllum, phenylalanine, phlomisoside I, phlorodizin, phyllodulcin, polyglycitol syrups, polypodoside A, pterocaryoside A, pterocaryoside B, rebiana, refiners syrup, rub syrup, rubusoside, selligueain A, shugr, siamenoside I, siraitia grosvenorii, soybean oligosaccharide, Splenda, SRI oxime V, steviol glycoside, steviolbioside, stevioside, strogins 1, 2, and 4, sucronic acid, sucrononate, sugar, suosan, phloridzin, superaspartame, tetrasaccharide, threitol, treacle, trilobtain, tryptophan and derivatives (6-trifluoromethyl-tryptophan, 6-chloro-D-tryptophan), vanilla sugar, volemitol, birch syrup, aspartame-acesulfame, assugrin, and combinations or blends of any two or more thereof.

In still other embodiments, the additional sweetener can be a chemically or enzymatically modified natural high potency sweetener. Modified natural high potency sweeteners include glycosylated natural high potency sweetener such as glucosyl-, galactosyl-, or fructosyl-derivatives containing 1-50 glycosidic residues. Glycosylated natural high potency sweeteners may be prepared by enzymatic transglycosylation reaction catalyzed by various enzymes possessing transglycosylating activity. In some embodiments, the modified sweetener can be substituted or unsubstituted.

Additional sweeteners also include combinations of any two or more of any of the aforementioned sweeteners. In some embodiments, the sweetener may comprise combinations of two, three, four or five sweeteners as disclosed herein. In some embodiments, the sweetener may be a sugar. In some embodiments, the sweetener may be a combination of one or more sugars and other natural and artificial sweeteners. In some embodiments, the sweetener is a caloric sweetener, such as sucrose, fructose, xylitol, erythritol, or combinations thereof. In some embodiments, the comestible compositions are free (or, in some embodiments) substantially free of *Stevia*-derived sweeteners, such as steviol glycosides, glucosylated steviol glycosides, or rebaudiosides. For example, in some embodiments, the comestible compositions are either free of *Stevia*-derived sweeteners or comprise *Stevia*-derived sweeteners in a concentration of no more than 1000 ppm, or no more than 500 ppm, or no more than 200 ppm, or no more than 100 ppm, or no more than 50 ppm, or no more than 20 ppm, or no more than 10 ppm, or no more than 5 ppm, or no more than 3 ppm, or no more than 1 ppm.

The malonyl steviol glycosides can be present in the comestible compositions in any suitable amount. In some embodiments, the malonyl steviol glycosides is present in an amount sufficient to enhance the taste (e.g., enhance the sweetness, reduce the sourness, or reduce the bitterness) of the compositions. Thus, in some embodiments, the comestible composition comprises the malonyl steviol glycosides in a concentration no greater than 1000 ppm, or no greater than 900 ppm, or no greater than 800 ppm, or no greater than 700 ppm, or no greater than 600 ppm, or no greater than 500 ppm, or no greater than 450 ppm, or no greater than 400 ppm, or no greater than 350 ppm, or no greater than 300 ppm, or no greater than 250 ppm, or no greater than 200 ppm, or no greater than 150 ppm, or no greater than 100 ppm, or no greater than 50 ppm, or no greater than 40 ppm, or no greater than 30 ppm, or no greater than 20 ppm. In some embodiments, the malonyl steviol glycosides are present in a minimum amount, such as 1 ppm or 5 ppm. Thus, in some embodiments, the comestible composition comprises the malonyl steviol glycosides in a concentration ranging from 1 ppm to 1000 ppm, or from 1 ppm to 900 ppm, or from 1 ppm to 800 ppm, or from 1 ppm to 700 ppm, or from 1 ppm to 600 ppm, or from 1 ppm to 500 ppm, or from 1 ppm to 450 ppm, or from 1 ppm to 400 ppm, or from 1 ppm to 350 ppm, or from 1 ppm to 300 ppm, or from 1 ppm to 250 ppm, or from 1 ppm to 200 ppm, or from 1 ppm to 150 ppm, or from 1 ppm to 100 ppm, or from 1 ppm to 50 ppm, or from 1 ppm to 40 ppm, or from 1 ppm to 30 ppm, or from 1 ppm to 20 ppm, or from 5 ppm to 1000 ppm, or from 5 ppm to 900 ppm, or from 5 ppm to 800 ppm, or from 5 ppm to 700 ppm, or from 5 ppm to 600 ppm, or from 5 ppm to 500 ppm, or from 5 ppm to 450 ppm, or from 5 ppm to 400 ppm, or from 5 ppm to 350 ppm, or from 5 ppm to 300 ppm, or from 5 ppm to 250 ppm, or from 5 ppm to 200 ppm, or from 5 ppm to 150 ppm, or from 5 ppm to 100 ppm, or from 5 ppm to 50 ppm, or from 5 ppm to 40 ppm, or from 5 ppm to 30 ppm, or from 5 ppm to 20 ppm. In embodiments where a sweetener, such as sucrose or fructose, are present, the weight-to-weight ratio of sweetener to the malonyl steviol glycosides in the comestible composition ranges from 1000:1 to 50000:1, or from 1000:1 to 10000:1, or from 2000:1 to 8000:1.

The comestible compositions or sweetener concentrates comprising the malonyl steviol glycosides can, in certain embodiments, comprise any additional ingredients or combination of ingredients as are commonly used in food and beverage products, including, but not limited to:

- acids, including, for example citric acid, phosphoric acid, ascorbic acid, sodium acid sulfate, lactic acid, or tartaric acid;
- bitter ingredients, including, for example caffeine, quinine, green tea, catechins, polyphenols, green *robusta* coffee extract, green coffee extract, potassium chloride, menthol, or proteins (such as proteins and protein isolates derived from plants, algae, or fungi);
- coloring agents, including, for example caramel color, Red #40, Yellow #5, Yellow #6, Blue #1, Red #3, purple carrot, black carrot juice, purple sweet potato, vegetable juice, fruit juice, beta carotene, turmeric curcumin, or titanium dioxide;
- preservatives, including, for example sodium benzoate, potassium benzoate, potassium sorbate, sodium metabisulfate, sorbic acid, or benzoic acid;
- antioxidants including, for example ascorbic acid, calcium disodium EDTA, alpha tocopherols, mixed tocopherols, rosemary extract, grape seed extract, resveratrol, or sodium hexametaphosphate;
- vitamins or functional ingredients including, for example resveratrol, Co-Q10, omega 3 fatty acids, theanine, choline chloride (citocoline), fibersol, inulin (chicory root), taurine, *Panax ginseng* extract, guanana extract, ginger extract, L-phenylalanine, L-carnitine, L-tartrate, D-glucoronolactone, inositol, bioflavonoids, *Echinacea*, ginko *biloba*, yerba mate, flax seed oil, garcinia cambogia rind extract, white tea extract, ribose, milk thistle extract, grape seed extract, pyrodixine HCl (vitamin B6), cyanoobalamin (vitamin B12), niacinamide (vitamin B3), biotin, calcium lactate, calcium pantothenate (pantothenic acid), calcium phosphate, calcium carbonate, chromium chloride, chromium polynicotinate, cupric sulfate, folic acid, ferric pyrophosphate, iron, magnesium lactate, magnesium carbonate, magnesium sulfate, monopotassium phosphate, monosodium phosphate, phosphorus, potassium iodide, potassium phosphate, riboflavin, sodium sulfate, sodium gluconate, sodium polyphosphate, sodium bicarbonate, thiamine mononitrate, vitamin D3, vitamin A palmitate, zinc gluconate, zinc lactate, or zinc sulphate;
- clouding agents, including, for example ester gun, brominated vegetable oil (BVO), or sucrose acetate isobutyrate (SAIB);
- buffers, including, for example sodium citrate, potassium citrate, or salt;
- flavors, including, for example propylene glycol, ethyl alcohol, glycerine, gum Arabic (gum acacia), maltodextrin, modified corn starch, dextrose, natural flavor, natural flavor with other natural flavors (natural flavor WONF), natural and artificial flavors, artificial flavor, silicon dioxide, magnesium carbonate, or tricalcium phosphate; or starches and stabilizers, including, for example pectin, xanthan gum, carboxylmethylcellulose (CMC), polysorbate 60, polysorbate 80, medium chain triglycerides, cellulose gel, cellulose gum, sodium caseinate, modified food starch, gum Arabic (gum acacia), inulin, or carrageenan.

The comestible compositions or sweetener concentrates comprising the malonyl steviol glycosides can have any suitable pH. In some embodiments, the malonyl steviol glycosides enhance the sweetness of a sweetener under a broad range of pH, e.g., from lower pH to neutral pH. The lower and neutral pH includes, but is not limited to, a pH from 1.5 to 9.0, or from 2.5 to 8.5; from 3.0 to 8.0; from 3.5 to 7.5; and from 4.0 to 7. In certain embodiments, the malonyl steviol glycosides can enhance the perceived sweetness of a fixed concentration of a sweetener in taste tests at a compound concentration of 50 μM, 40 μM, 30 μM, 20 μM, or 10 μM at both low to neutral pH value. In certain embodiments, the enhancement factor of the compounds as disclosed and described herein, individually or in combination, at the lower pH is substantially similar to the enhancement factor of the compounds at neutral pH. Such consistent sweet enhancing property under a broad range of pH allow a broad use in a wide variety of foods and beverages of the compounds as disclosed and described herein, individually or in combination.

The comestible compositions set forth according to any of the foregoing embodiments, also include, in certain embodiments, one or more additional flavor-modifying compounds, such as compounds that enhance sweetness (e.g., hesperetin, naringenin, glucosylated steviol glycosides, etc.), compounds that block bitterness, compounds that enhance umami, compounds that reduce sourness or licorice taste, compounds that enhance saltiness, compounds that enhance a cooling effect, or any combinations of the foregoing.

Thus, in some embodiments, comestible compositions disclosed herein comprise the malonyl steviol glycosides are combined with one or more other sweetness enhancing compounds. Such sweetness enhancing compounds include, but are not limited to, naturally derived compounds, such as hesperitin, naringenin, glucosylated steviol glycosides, or synthetic compounds, such as any compounds set forth in U.S. Pat. Nos. 8,541,421; 8,815,956; 9,834,544; 8,592,592; 8,877,922; 9,000,054; and 9,000,051, as well as U.S. Patent Application Publication No. 2017/0119032. The malonyl steviol glycosides may be used in combination with such other sweetness enhancers in any suitable ratio (w/w) ranging from 1:1000 to 1000:1, or from 1:100 to 100:1, or from, 1:50 to 50:1, or from 1:25 to 25:1, or from 1:10 to 10:1, such as 1:25, 1:24, 1:23, 1:22, 1:21, 1:20, 1:19, 1:18, 1:17, 1:16, 1:15, 1:14, 1:13, 1:12, 1:11, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 21:1, 22:1, 23:1, 24:1, or 25:1. In some embodiments of any of the preceding embodiments, the malonyl steviol glycosides is combined with glucosylated steviol glycosides in any of the above ratios. As used herein, the term "glucosylated steviol glycoside" refers to the product of enzymatically glucosylating natural steviol glycoside compounds. The glucosylation generally occurs through a glycosidic bond, such as an α-1,2 bond, an α-1,4 bond, an α-1.6 bond, a β-1,2 bond, a β-1,4 bond, a β-1,6 bond, and so forth. In some embodiments of any of the preceding embodiments, the malonyl steviol glycosides is combined with 3-((4-amino-2,2-dioxo-1H-benzo[c][1,2,6]thiadiazin-5-yl)oxy)-2,2-dimethyl-N-propyl-propanamide, in any of the above ratios.

In some further embodiments, comestible compositions disclosed herein comprise the malonyl steviol glycosides are combined with one or more umami enhancing compounds. Such umami enhancing compounds include, but are not limited to, naturally derived compounds, such as ericamide, or synthetic compounds, such as any compounds set forth in U.S. Pat. Nos. 8,735,081; 8,124,121; and 8,968,708. The malonyl steviol glycosides may be used in combination with such umami enhancers in any suitable ratio (w/w) ranging from 1:1000 to 1000:1, or from 1:100 to 100:1, or from, 1:50 to 50:1, or from 1:25 to 25:1, or from 1:10 to 10:1, such as 1:25, 1:24, 1:23, 1:22, 1:21, 1:20, 1:19, 1:18, 1:17, 1:16, 1:15, 1:14, 1:13, 1:12, 1:11, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 21:1, 22:1, 23:1, 24:1, or 25:1.

In some further embodiments, comestible compositions disclosed herein comprise the malonyl steviol glycosides are combined with one or more cooling enhancing compounds. Such cooling enhancing compounds include, but are not limited to, naturally derived compounds, such as menthol or analogs thereof, or synthetic compounds, such as any compounds set forth in U.S. Pat. Nos. 9,394,287 and 10,421,727. The malonyl steviol glycosides may be used in combination with such umami enhancers in any suitable ratio (w/w) ranging from 1:1000 to 1000:1, or from 1:100 to 100:1, or from, 1:50 to 50:1, or from 1:25 to 25:1, or from 1:10 to 10:1, such as 1:25, 1:24, 1:23, 1:22, 1:21, 1:20, 1:19, 1:18, 1:17, 1:16, 1:15, 1:14, 1:13, 1:12, 1:11, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 21:1, 22:1, 23:1, 24:1, or 25:1.

In some further embodiments, comestible compositions disclosed herein comprise the malonyl steviol glycosides are combined with one or more bitterness blocking compounds. Such bitterness blocking compounds include, but are not limited to, naturally derived compounds, such as menthol or analogs thereof, or synthetic compounds, such as any compounds set forth in U.S. Pat. Nos. 8,076,491; 8,445,692; and 9,247,759. The malonyl steviol glycosides may be used in combination with such bitterness blockers in any suitable ratio (w/w) ranging from 1:1000 to 1000:1, or from 1:100 to 100:1, or from, 1:50 to 50:1, or from 1:25 to 25:1, or from 1:10 to 10:1, such as 1:25, 1:24, 1:23, 1:22, 1:21, 1:20, 1:19, 1:18, 1:17, 1:16, 1:15, 1:14, 1:13, 1:12, 1:11, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 21:1, 22:1, 23:1, 24:1, or 25:1.

In some further embodiments, comestible compositions disclosed herein comprise the malonyl steviol glycosides are combined with one or more sour taste modulating compounds. The malonyl steviol glycosides may be used in combination with such sour taste modulating compounds in any suitable ratio (w/w) ranging from 1:1000 to 1000:1, or from 1:100 to 100:1, or from, 1:50 to 50:1, or from 1:25 to 25:1, or from 1:10 to 10:1, such as 1:25, 1:24, 1:23, 1:22, 1:21, 1:20, 1:19, 1:18, 1:17, 1:16, 1:15, 1:14, 1:13, 1:12, 1:11, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 21:1, 22:1, 23:1, 24:1, or 25:1.

In some further embodiments, comestible compositions disclosed herein comprise the malonyl steviol glycosides are combined with one or more mouthfeel modifying compounds. Such mouthfeel modifying compounds include, but are not limited to, tannins, cellulosic materials, bamboo powder, and the like. The malonyl steviol glycosides may be used in combination with such mouthfeel enhancers in any suitable ratio (w/w) ranging from 1:1000 to 1000:1, or from 1:100 to 100:1, or fro, 1:50 to 50:1, or from 1:25 to 25:1, or from 1:10 to 10:1, such as 1:25, 1:24, 1:23, 1:22, 1:21, 1:20, 1:19, 1:18, 1:17, 1:16, 1:15, 1:14, 1:13, 1:12, 1:11, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 21:1, 22:1, 23:1, 24:1, or 25:1.

In some further embodiments, comestible compositions disclosed herein comprise the malonyl steviol glycosides are combined with one or more flavor masking compounds. Such flavor masking compounds include, but are not limited to, cellulosic materials, materials extracted from fungus, materials extracted from plants, citric acid, carbonic acid (or carbonates), and the like. The malonyl steviol glycosides may be used in combination with such mouthfeel enhancers in any suitable ratio (w/w) ranging from 1:1000 to 1000:1, or from 1:100 to 100:1, or from, 1:50 to 50:1, or from 1:25 to 25:1, or from 1:10 to 10:1, such as 1:25, 1:24, 1:23, 1:22, 1:21, 1:20, 1:19, 1:18, 1:17, 1:16, 1:15, 1:14, 1:13, 1:12, 1:11, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 21:1, 22:1, 23:1, 24:1, or 25:1.

In some aspects related to the preceding aspects and embodiments, the disclosure provides uses of the malonyl steviol glycosides to enhance the flavor of a flavored composition, such as a flavored article. Such flavored compositions can use any suitable flavors, such as any of the flavors set forth above.

Flavored Products and Concentrates

In certain aspects, the disclosure provides flavored products comprising any compositions of the preceding five aspects. In some embodiment, the flavored products are beverage products, such as soda, flavored water, tea, and the like. In some other embodiments, the flavored products are food products, such as yogurt.

In embodiments where the flavored product is a beverage, the beverage may be selected from the group consisting of enhanced sparkling beverages, colas, lemon-lime flavored sparkling beverages, orange flavored sparkling beverages, grape flavored sparkling beverages, strawberry flavored sparkling beverages, pineapple flavored sparkling beverages, ginger-ales, root beers, fruit juices, fruit-flavored juices, juice drinks, nectars, vegetable juices, vegetable-flavored juices, sports drinks, energy drinks, enhanced water drinks, enhanced water with vitamins, near water drinks, coconut waters, tea type drinks, coffees, cocoa drinks, beverages containing milk components, beverages containing cereal extracts and smoothies. In some embodiments, the beverage may be a soft drink.

In certain embodiments of any aspects and embodiments set forth herein that refer to an flavored product, the flavored product is a non-naturally-occurring product, such as a packaged food or beverage product.

Further non-limiting examples of food and beverage products or formulations include sweet coatings, frostings, or glazes for such products or any entity included in the Soup category, the Dried Processed Food category, the Beverage category, the Ready Meal category, the Canned or Preserved Food category, the Frozen Processed Food category, the Chilled Processed Food category, the Snack Food category, the Baked Goods category, the Confectionery category, the Dairy Product category, the Ice Cream category, the Meal Replacement category, the Pasta and Noodle category, and the Sauces, Dressings, Condiments category, the Baby Food category, and/or the Spreads category.

In general, the Soup category refers to canned/preserved, dehydrated, instant, chilled, UHT and frozen soup. For the purpose of this definition soup(s) means a food prepared from meat, poultry, fish, vegetables, grains, fruit and other ingredients, cooked in a liquid which may include visible pieces of some or all of these ingredients. It may be clear (as a broth) or thick (as a chowder), smooth, pureed or chunky, ready-to-serve, semi-condensed or condensed and may be served hot or cold, as a first course or as the main course of a meal or as a between meal snack (sipped like a beverage). Soup may be used as an ingredient for preparing other meal components and may range from broths (consomme) to sauces (cream or cheese-based soups).

The Dehydrated and Culinary Food Category usually means: (i) Cooking aid products such as: powders, granules, pastes, concentrated liquid products, including concentrated bouillon, bouillon and bouillon like products in pressed cubes, tablets or powder or granulated form, which are sold separately as a finished product or as an ingredient within a product, sauces and recipe mixes (regardless of technology); (ii) Meal solutions products such as: dehydrated and freeze dried soups, including dehydrated soup mixes, dehydrated instant soups, dehydrated ready-to-cook soups, dehydrated or ambient preparations of ready-made dishes, meals and single serve entrees including pasta, potato and rice dishes; and (iii) Meal embellishment products such as: condiments, marinades, salad dressings, salad toppings, dips, breading, batter mixes, shelf stable spreads, barbecue sauces, liquid recipe mixes, concentrates, sauces or sauce mixes, including recipe mixes for salad, sold as a finished product or as an ingredient within a product, whether dehydrated, liquid or frozen.

The Beverage category usually means beverages, beverage mixes and concentrates, including but not limited to, carbonated and non-carbonated beverages, alcoholic and non-alcoholic beverages, ready to drink beverages, liquid concentrate formulations for preparing beverages such as sodas, and dry powdered beverage precursor mixes. The Beverage category also includes the alcoholic drinks, the soft drinks, sports drinks, isotonic beverages, and hot drinks. The alcoholic drinks include, but are not limited to beer, cider/perry, FABs, wine, and spirits. The soft drinks include, but are not limited to carbonates, such as colas and non-cola carbonates; fruit juice, such as juice, nectars, juice drinks and fruit flavored drinks; bottled water, which includes sparkling water, spring water and purified/table water; functional drinks, which can be carbonated or still and include sport, energy or elixir drinks; concentrates, such as liquid and powder concentrates in ready to drink measure. The drinks, either hot or cold, include, but are not limited to coffee or ice coffee, such as fresh, instant, and combined coffee; tea or ice tea, such as black, green, white, oolong, and flavored tea; and other drinks including flavor-, malt- or plant-based powders, granules, blocks or tablets mixed with milk or water.

The Snack Food category generally refers to any food that can be a light informal meal including, but not limited to Sweet and savory snacks and snack bars. Examples of snack food include, but are not limited to fruit snacks, chips/crisps, extruded snacks, tortilla/corn chips, popcorn, pretzels, nuts and other sweet and savory snacks. Examples of snack bars include, but are not limited to granola/muesli bars, breakfast bars, energy bars, fruit bars and other snack bars.

The Baked Goods category generally refers to any edible product the process of preparing which involves exposure to heat or excessive sunlight. Examples of baked goods include, but are not limited to bread, buns, cookies, muffins, cereal, toaster pastries, pastries, waffles, tortillas, biscuits, pies, bagels, tarts, quiches, cake, any baked foods, and any combination thereof.

The Ice Cream category generally refers to frozen dessert containing cream and sugar and flavoring. Examples of ice cream include, but are not limited to: impulse ice cream; take-home ice cream; frozen yoghurt and artisanal ice cream; soy, oat, bean (e.g., red bean and mung bean), and rice-based ice creams.

The Confectionery category generally refers to edible product that is sweet to the taste. Examples of confectionery include, but are not limited to candies, gelatins, chocolate confectionery, sugar confectionery, gum, and the likes and any combination products.

The Meal Replacement category generally refers to any food intended to replace the normal meals, particularly for people having health or fitness concerns. Examples of meal replacement include, but are not limited to slimming products and convalescence products.

The Ready Meal category generally refers to any food that can be served as meal without extensive preparation or processing. The ready meal includes products that have had recipe "skills" added to them by the manufacturer, resulting in a high degree of readiness, completion and convenience. Examples of ready meal include, but are not limited to canned/preserved, frozen, dried, chilled ready meals; dinner mixes; frozen pizza; chilled pizza; and prepared salads.

The Pasta and Noodle category includes any pastas and/or noodles including, but not limited to canned, dried and chilled/fresh pasta; and plain, instant, chilled, frozen and snack noodles.

The Canned/Preserved Food category includes, but is not limited to canned/preserved meat and meat products, fish/seafood, vegetables, tomatoes, beans, fruit, ready meals, soup, pasta, and other canned/preserved foods.

The Frozen Processed Food category includes, but is not limited to frozen processed red meat, processed poultry, processed fish/seafood, processed vegetables, meat substitutes, processed potatoes, bakery products, desserts, ready meals, pizza, soup, noodles, and other frozen food.

The Dried Processed Food category includes, but is not limited to rice, dessert mixes, dried ready meals, dehydrated soup, instant soup, dried pasta, plain noodles, and instant noodles. The Chill Processed Food category includes, but is not limited to chilled processed meats, processed fish/seafood products, lunch kits, fresh cut fruits, ready meals, pizza, prepared salads, soup, fresh pasta and noodles.

The Sauces, Dressings and Condiments category includes, but is not limited to tomato pastes and purees, bouillon/stock cubes, herbs and spices, monosodium glutamate (MSG), table sauces, soy based sauces, pasta sauces, wet/cooking sauces, dry sauces/powder mixes, ketchup, mayonnaise, mustard, salad dressings, vinaigrettes, dips, pickled products, and other sauces, dressings and condiments.

The Baby Food category includes, but is not limited to milk- or soybean-based formula; and prepared, dried and other baby food.

The Spreads category includes, but is not limited to jams and preserves, honey, chocolate spreads, nut based spreads, and yeast based spreads.

The Dairy Product category generally refers to edible product produced from mammal's milk. Examples of dairy product include, but are not limited to drinking milk products, cheese, yoghurt and sour milk drinks, and other dairy products.

Additional examples for flavored products, particularly food and beverage products or formulations, are provided as follows. Exemplary comestible compositions include one or more confectioneries, chocolate confectionery, tablets, countlines, bagged selflines/softlines, boxed assortments, standard boxed assortments, twist wrapped miniatures, seasonal chocolate, chocolate with toys, alfajores, other chocolate confectionery, mints, standard mints, power mints, boiled sweets, pastilles, gums, jellies and chews, toffees, caramels and nougat, medicated confectionery, lollipops, liquorice, other sugar confectionery, bread, packaged/industrial bread, unpackaged/artisanal bread, pastries, cakes, packaged/industrial cakes, unpackaged/artisanal cakes, cookies, chocolate coated biscuits, sandwich biscuits, filled biscuits, savory biscuits and crackers, bread substitutes, breakfast cereals, rte cereals, family breakfast cereals, flakes, muesli, other cereals, children's breakfast cereals, hot cereals, ice cream, impulse ice cream, single portion dairy ice cream, single portion water ice cream, multi-pack dairy ice cream, multi-pack water ice cream, take-home ice cream, take-home dairy ice cream, ice cream desserts, bulk ice cream, take-home water ice cream, frozen yoghurt, artisanal ice cream, dairy products, milk, fresh/pasteurized milk, full fat fresh/pasteurized milk, semi skimmed fresh/pasteurized milk, long-life/uht milk, full fat long life/uht milk, semi skimmed long life/uht milk, fat-free long life/uht milk, goat milk, condensed/evaporated milk, plain condensed/evaporated milk, flavored, functional and other condensed milk, flavored milk drinks, dairy only flavored milk drinks, flavored milk drinks with fruit juice, soy milk, sour milk drinks, fermented dairy drinks, coffee whiteners, powder milk, flavored powder milk drinks, cream, cheese, processed cheese, spreadable processed cheese, unspreadable processed cheese, unprocessed cheese, spreadable unprocessed cheese, hard cheese, packaged hard cheese, unpackaged hard cheese, yoghurt, plain/natural yoghurt, flavored yoghurt, fruited yoghurt, probiotic yoghurt, drinking yoghurt, regular drinking yoghurt, probiotic drinking yoghurt, chilled and shelf-stable desserts, dairy-based desserts, soy-based desserts, chilled snacks, fromage frais and quark, plain fromage frais and quark, flavored fromage frais and quark, savory fromage frais and quark, sweet and savory snacks, fruit snacks, chips/crisps, extruded snacks, tortilla/corn chips, popcorn, pretzels, nuts, other sweet and savory snacks, snack bars, granola bars, breakfast bars, energy bars, fruit bars, other snack bars, meal replacement products, slimming products, convalescence drinks, ready meals, canned ready meals, frozen ready meals, dried ready meals, chilled ready meals, dinner mixes, frozen pizza, chilled pizza, soup, canned soup, dehydrated soup, instant soup, chilled soup, hot soup, frozen soup, pasta, canned pasta, dried pasta, chilled/fresh pasta, noodles, plain noodles, instant noodles, cups/bowl instant noodles, pouch instant noodles, chilled noodles, snack noodles, canned food, canned meat and meat products, canned fish/seafood, canned vegetables, canned tomatoes, canned beans, canned fruit, canned ready meals, canned soup, canned pasta, other canned foods, frozen food, frozen processed red meat, frozen processed poultry, frozen processed fish/seafood, frozen processed vegetables, frozen meat substitutes, frozen potatoes, oven baked potato chips, other oven baked potato products, non-oven frozen potatoes, frozen bakery products, frozen desserts, frozen ready meals, frozen pizza, frozen soup, frozen noodles, other frozen food, dried food, dessert mixes, dried ready meals, dehydrated soup, instant soup, dried pasta, plain noodles, instant noodles, cups/bowl instant noodles, pouch instant noodles, chilled food, chilled processed meats, chilled fish/seafood products, chilled processed fish, chilled coated fish, chilled smoked fish, chilled lunch kit, chilled ready meals, chilled pizza, chilled soup, chilled/fresh pasta, chilled noodles, oils and fats, olive oil, vegetable and seed oil, cooking fats, butter, margarine, spreadable oils and fats, functional spreadable oils and fats, sauces, dressings and condiments, tomato pastes and purees, bouillon/stock cubes, stock cubes, gravy granules, liquid stocks and fonds, herbs and spices, fermented sauces, soy based sauces, pasta sauces, wet sauces, dry sauces/powder mixes, ketchup, mayonnaise, regular mayonnaise, mustard, salad dressings, regular salad dressings, low fat salad dressings, vinaigrettes, dips, pickled products, other sauces, dressings and condiments, baby food, milk formula, standard milk formula, follow-on milk formula, toddler milk formula, hypoallergenic milk formula, prepared baby food, dried baby food, other baby food, spreads, jams and preserves, honey, chocolate spreads, nut-based spreads, and yeast-based spreads. Exemplary comestible compositions also include confectioneries, bakery products, ice creams, dairy products, sweet and savory snacks, snack bars, meal replacement products, ready meals, soups, pastas, noodles, canned foods, frozen foods, dried foods, chilled foods, oils and fats, baby foods, or spreads or a mixture thereof. Exemplary comestible compositions also include breakfast cereals, sweet beverages or solid or liquid concentrate compositions for preparing beverages, ideally so as to enable the reduction in concentration of previously known saccharide sweeteners, or artificial sweeteners.

Some embodiments provide a chewable composition that may or may not be intended to be swallowed. In some embodiments, the chewable composition may be gum, chewing gum, sugarized gum, sugar-free gum, functional gum, bubble gum including compounds as disclosed and described herein, individually or in combination.

In some embodiments, the malonyl steviol glycosides modulates the sweet taste or other taste properties of other natural or synthetic sweet tastants, and comestible compositions made therefrom. In one embodiment, the malonyl steviol glycosides may be used or provided in its ligand enhancing concentration(s). For example, in some such embodiments, the malonyl steviol glycosides is present in the comestible composition at a concentration ranging from 0.001 ppm to 100 ppm, or narrower alternative ranges from 0.1 ppm to 50 ppm, from 0.01 ppm to 40 ppm, from 0.05 ppm to 30 ppm, from 0.01 ppm to 25 ppm, or from 0.1 ppm to 30 ppm, or from 0.1 ppm to 25 ppm, or from 1 ppm to 30 ppm, or from 1 ppm to 25 ppm.

In some embodiments, the malonyl steviol glycosides is provided in a flavoring concentrate formulation, e.g., suitable for subsequent processing to produce a ready-to-use (i.e., ready-to-serve) product. By "a flavoring concentrate formulation", it is meant a formulation which should be reconstituted with one or more diluting medium to become a ready-to-use composition. The term "ready-to-use composition" is used herein interchangeably with "comestible composition", which denotes any substance that, either alone or together with another substance, can be taken by mouth whether intended for consumption or not. In one embodiment, the ready-to-use composition includes a composition that can be directly consumed by a human or animal. The flavoring concentrate formulation is typically used by mixing with or diluted by one or more diluting medium, e.g., any consumable or comestible ingredient or product, to impart or modify one or more flavors to the diluting medium. Such a use process is often referred to as reconstitution. The reconstitution can be conducted in a household setting or an industrial setting. For example, a frozen fruit juice concentrate can be reconstituted with water or other aqueous medium by a consumer in a kitchen to obtain the ready-to-use fruit juice beverage. In another example, a soft drink syrup concentrate can be reconstituted with water or other aqueous medium by a manufacturer in large industrial scales to produce the ready-to-use soft drinks. Since the flavoring concentrate formulation has the flavoring agent or flavor modifying agent in a concentration higher than the ready-to-use composition, the flavoring concentrate formulation is typically not suitable for being consumed directly without reconstitution. There are many benefits of using and producing a flavoring concentrate formulation. For example, one benefit is the reduction in weight and volume for transportation as the flavoring concentrate formulation can be reconstituted at the time of usage by the addition of suitable solvent, solid or liquid.

In certain embodiments of any aspects and embodiments set forth herein that refer to a sweetening or flavoring concentrate, the sweetening or flavoring concentrate is a non-naturally-occurring product, such as a composition specifically manufactured for the production of a flavored product, such as food or beverage product.

In some embodiments, the flavoring concentrate formulation comprises: the malonyl steviol glycosides; a carrier; and, optionally, at least one adjuvant. The term "carrier" denotes a usually inactive accessory substance, such as solvents, binders, bulking agents, or other inert medium, which is used in combination with the present compound and one or more optional adjuvants to form the formulation. For example, water or starch can be a carrier for a flavoring concentrate formulation. In some embodiments, the carrier is the same as the diluting medium for reconstituting the flavoring concentrate formulation; and in other embodiments, the carrier is different from the diluting medium. The term "carrier" as used herein includes, but is not limited to, comestibly acceptable carrier.

The term "adjuvant" denotes an additive which supplements, stabilizes, maintains, or enhances the intended function or effectiveness of the active ingredient, such as the compound of the present invention. In one embodiment, the at least one adjuvant comprises one or more flavoring agents. The flavoring agent may be of any flavor known to one skilled in the art or consumers, such as the flavor of chocolate, coffee, tea, mocha, French vanilla, peanut butter, chai, or combinations thereof. In another embodiment, the at least one adjuvant comprises one or more sweeteners. The one or more sweeteners can be any of the sweeteners described in this application. In another embodiment, the at least one adjuvant comprises one or more ingredients selected from the group consisting of a emulsifier, a stabilizer, an antimicrobial preservative, an antioxidant, vitamins, minerals, fats, starches, protein concentrates and isolates, salts, and combinations thereof. Examples of emulsifiers, stabilizers, antimicrobial preservatives, antioxidants, vitamins, minerals, fats, starches, protein concentrates and isolates, and salts are described in U.S. Pat. No. 6,468,576, the content of which is hereby incorporated by reference in its entirety for all purposes.

In some embodiments, the present flavoring concentrate formulation can be in a form selected from the group consisting of liquid including solution and suspension, solid, foamy material, paste, gel, cream, and a combination thereof, such as a liquid containing certain amount of solid contents. In one embodiment, the flavoring concentrate formulation is in form of a liquid including aqueous-based and nonaqueous-based. In some embodiments, the present flavoring concentrate formulation can be carbonated or non-carbonated.

The flavoring concentrate formulation may further comprise a freezing point depressant, nucleating agent, or both as the at least one adjuvant. The freezing point depressant is an ingestibly acceptable compound or agent which can depress the freezing point of a liquid or solvent to which the compound or agent is added. That is, a liquid or solution containing the freezing point depressant has a lower freezing point than the liquid or solvent without the freezing point depressant. In addition to depress the onset freezing point, the freezing point depressant may also lower the water activity of the flavoring concentrate formulation. The examples of the freezing point depressant include, but are not limited to, carbohydrates, oils, ethyl alcohol, polyol, e.g., glycerol, and combinations thereof. The nucleating agent denotes an ingestibly acceptable compound or agent which is able to facilitate nucleation. The presence of nucleating agent in the flavoring concentrate formulation can improve the mouthfeel of the frozen Blushes of a frozen slush and to help maintain the physical properties and performance of the slush at freezing temperatures by increasing the number of desirable ice crystallization centers. Examples of nucleating agents include, but are not limited to, calcium silicate, calcium carbonate, titanium dioxide, and combinations thereof.

In some embodiments, the flavoring concentrate formulation is formulated to have a low water activity for extended shelf life. Water activity is the ratio of the vapor pressure of water in a formulation to the vapor pressure of pure water at the same temperature. In one embodiment, the flavoring concentrate formulation has a water activity of less than about 0.85. In another embodiment, the flavoring concentrate formulation has a water activity of less than about 0.80. In another embodiment, the flavoring concentrate formulation has a water activity of less than about 0.75.

In some embodiments, the flavoring concentrate formulation has the present compound in a concentration that is at least 2 times of the concentration of the compound in a ready-to-use composition. In one embodiment, the flavoring concentrate formulation has the present compound in a concentration that is at least 5 times of the concentration of the compound in a ready-to-use composition. In one embodiment, the flavoring concentrate formulation has the present compound in a concentration that is at least 10 times of the concentration of the compound in a ready-to-use composition. In one embodiment, the flavoring concentrate formulation has the present compound in a concentration that is at least 15 times of the concentration of the compound in a ready-to-use composition. In one embodiment, the flavoring concentrate formulation has the present compound in a concentration that is at least 20 times of the concentration of the compound in a ready-to-use composition. In one embodiment, the flavoring concentrate formulation has the present compound in a concentration that is at least 30 times of the concentration of the compound in a ready-to-use composition. In one embodiment, the flavoring concentrate formulation has the present compound in a concentration that is at least 40 times of the concentration of the compound in a ready-to-use composition. In one embodiment, the flavoring concentrate formulation has the present compound in a concentration that is at least 50 times of the concentration of the compound in a ready-to-use composition. In one embodiment, the flavoring concentrate formulation has the present compound in a concentration that is at least 60 times of the concentration of the compound in a ready-to-use composition. In one embodiment, the flavoring concentrate formulation has the present compound in a concentration that is up to 100 times of the concentration of the compound in a ready-to-use composition.

The sweetening or flavoring concentrates set forth according to any of the foregoing embodiments, also include, in certain embodiments, one or more additional mogroside compounds, such as compounds that enhance sweetness (e.g., hesperetin, naringenin, glucosylated steviol glycosides, etc.), compounds that block bitterness (e.g., eriodictyol, homoeriodictyol, sterubin, and salts or glycoside derivatives thereof, as well as vanillyl lignans, e.g., matairesinol and other compounds set forth in PCT Publication No. WO 2012/146584), compounds that enhance umami (e.g., rubemamine, rubescenamine, (E)-3-(3,4-dimethoxyphenyl)-N-(4-methoxyphenethyl)acrylamide, and the like), compounds that reduce sourness and/or licorice taste, compounds that enhance saltiness, compounds that enhance a cooling effect, or any combinations of the foregoing.

In some embodiments, the comestible compositions comprising the malonyl steviol glycosides also include one or more vanilla flavor compounds, such as 4-hydroxy-3-methoxy-benzaldehyde or 2-hydroxy-4-methoxybenzaldehyde. Such comestible compositions can suitably be used in a variety of different flavored products, such as coffee-based drinks, protein mixes, meal-replacement drinks, ice cream, and the like.

Tabletop Compositions

In some further aspects, the disclosure provides a tabletop sweetener composition comprising: (a) at least one sweetener composition according to any of the preceding aspects and embodiments thereof (namely, compositions comprising a sweetener and the malonyl steviol glycosides); and (b) at least one bulking agent.

The tabletop sweetener composition may take any suitable form including, but not limited to, an amorphous solid, a crystal, a powder, a tablet, a liquid, a cube, a glace or coating, a granulated product, an encapsulated form abound to or coated on to carriers/particles, wet or dried, or combinations thereof.

The tabletop sweetener composition may contain further additives known to those skilled in the art. These additives include but are not limited to bubble forming agents, bulking agents, carriers, fibers, sugar alcohols, oligosaccharides, sugars, high intensity sweeteners, nutritive sweeteners, flavorings, flavor enhancers, flavor stabilizers, acidulants, anti-caking and free-flow agents. Such additives are for example described by H. Mitchell (H. Mitchell, Sweeteners and Sugar Alternatives in Food Technology, Blackwell Publishing Ltd, 2006, which is incorporated herein by reference in its entirety). As used herein, the term "flavorings" may include those flavors known to the skilled person, such as natural and artificial flavors. These flavorings may be chosen from synthetic flavor oils and flavoring aromatics or oils, oleoresins and extracts derived from plants, leaves, flowers, fruits, and so forth, and combinations thereof. Non-limiting representative flavor oils include spearmint oil, cinnamon oil, oil of wintergreen (methyl salicylate), peppermint oil, Japanese mint oil, clove oil, bay oil, anise oil, *eucalyptus* oil, thyme oil, cedar leaf oil, oil of nutmeg, allspice, oil of sage, mace, oil of bitter almonds, and *cassia* oil. Also useful flavorings are artificial, natural and synthetic fruit flavors such as vanilla, and citrus oils including lemon, orange, lime, grapefruit, yazu, sudachi, and fruit essences including apple, pear, peach, grape, blueberry, strawberry, raspberry, cherry, plum, pineapple, watermelon, apricot, banana, melon, apricot, ume, cherry, raspberry, blackberry, tropical fruit, mango, mangosteen, pomegranate, *papaya* and so forth. Other potential flavors include a milk flavor, a butter flavor, a cheese flavor, a cream flavor, and a yogurt flavor; a vanilla flavor; tea or coffee flavors, such as a green tea flavor, a oolong tea flavor, a tea flavor, a cocoa flavor, a chocolate flavor, and a coffee flavor; mint flavors, such as a peppermint flavor, a spearmint flavor, and a Japanese mint flavor; spicy flavors, such as an asafetida flavor, an ajowan flavor, an anise flavor, an *angelica* flavor, a fennel flavor, an allspice flavor, a cinnamon flavor, a camomile flavor, a mustard flavor, a cardamom flavor, a caraway flavor, a cumin flavor, a clove flavor, a pepper flavor, a coriander flavor, a *sassafras* flavor, a savory flavor, a Zanthoxyli Fructus flavor, a *perilla* flavor, a juniper berry flavor, a ginger flavor, a star anise flavor, a horseradish flavor, a thyme flavor, a tarragon flavor, a dill flavor, a *capsicum* flavor, a nutmeg flavor, a basil flavor, a marjoram flavor, a rosemary flavor, a bayleaf flavor, and a wasabi (Japanese horseradish) flavor; alcoholic flavors, such as a wine flavor, a whisky flavor, a brandy flavor, a rum flavor, a gin flavor, and a liqueur flavor; floral flavors; and vegetable flavors, such as an onion flavor, a garlic flavor, a cabbage flavor, a carrot flavor, a celery flavor, mushroom flavor, and a tomato flavor. These flavoring agents may be used in liquid or solid form and may be used individually or in admixture. Commonly used flavors include mints such as peppermint, menthol, spearmint, artificial vanilla, cinnamon derivatives, and various fruit flavors, whether employed individually or in admixture. Flavors may also provide breath freshening properties, particularly the mint flavors when used in combination with cooling agents.

Flavors may also provide breath freshening properties, particularly the mint flavors when used in combination with cooling agents. These flavorings may be used in liquid or solid form and may be used individually or in admixture. Other useful flavorings include aldehydes and esters such as cinnamyl acetate, cinnamaldehyde, citral diethylacetal, dihydrocarvyl acetate, eugenyl formate, p-methylamisol, and so forth may be used. Generally any flavoring or food additive such as those described in Chemicals Used in Food Processing, Publication 1274, pp. 63-258 (National Academy of Sciences) may be used. This publication is incorporated herein by reference.

Further examples of aldehyde flavorings include but are not limited to acetaldehyde (apple), benzaldehyde (cherry, almond), anisic aldehyde (licorice, anise), cinnamic aldehyde (cinnamon), citral, i.e., alpha-citral (lemon, lime), neral, i.e., beta-citral (lemon, lime), decanal (orange, lemon), ethyl vanillin (vanilla, cream), heliotrope, i.e., piperonal (vanilla, cream), vanillin (vanilla, cream), alpha-amyl cinnamaldehyde (spicy fruity flavors), butyraldehyde (butter, cheese), valeraldehyde (butter, cheese), citronellal (modifies, many types), decanal (citrus fruits), aldehyde C-8 (citrus fruits), aldehyde C-9 (citrus fruits), aldehyde C-12 (citrus fruits), 2-ethyl butyraldehyde (berry fruits), hexenal, i.e., trans-2 (berry fruits), tolyl aldehyde (cherry, almond), veratraldehyde (vanilla), 2,6-dimethyl-5-heptenal, i.e., melonal (melon), 2,6-dimethyloctanal (green fruit), and 2-dodecenal (citrus, mandarin), cherry, grape, strawberry shortcake, and mixtures thereof. These listings of flavorings are merely exemplary and are not meant to limit either the term "flavoring" or the scope of the disclosure generally.

In some embodiments, the flavoring may be employed in either liquid form and/or dried form. When employed in the latter form, suitable drying means such as spray drying the oil may be used. Alternatively, the flavoring may be absorbed onto water soluble materials, such as cellulose, starch, sugar, maltodextrin, gum arabic and so forth or may be encapsulated. The actual techniques for preparing such dried forms are well-known.

In some embodiments, the tabletop sweetener can be made to be similar to brown sugar. In such embodiments, compounds imparting brown notes can be added to the composition to make it taste more similar to brown sugar.

In some embodiments, the flavorings may be used in many distinct physical forms well-known in the art to provide an initial burst of flavor and/or a prolonged sensation of flavor. Without being limited thereto, such physical forms include free forms, such as spray dried, powdered, beaded forms, encapsulated forms, and mixtures thereof.

Suitable bulking agents include, but are not limited to maltodextrin (10 DE, 18 DE, or 5 DE), corn syrup solids (20 or 36 DE), sucrose, fructose, glucose, invert sugar, sorbitol, xylose, ribulose, mannose, xylitol, mannitol, galactitol, erythritol, maltitol, lactitol, isomalt, maltose, tagatose, lactose, inulin, glycerol, propylene glycol, polyols, polydextrose, fructooligosaccharides, cellulose and cellulose derivatives, and the like, and mixtures thereof. Additionally, granulated sugar (sucrose) or other caloric sweeteners such as crystalline fructose, other carbohydrates, or sugar alcohols can be used as a bulking agent due to their provision of good content uniformity without the addition of significant calories.

In one embodiment, the at least one bulking agent may be a bulking agent described in U.S. Pat. No. 8,993,027. In another embodiment, the at least one bulking agent may be a bulking agent described in U.S. Pat. No. 6,607,771. In another embodiment, the at least one bulking agent may be a bulking agent described in U.S. Pat. No. 6,932,982.

In some embodiments, the tabletop sweetener composition may further comprise at least one anti-caking agent. As used herein the phrase "anti-caking agent" and "flow agent" refer to any composition which prevents, reduces, inhibits, or suppresses the at least one sweetener from attaching, binding, or contacting to another sweetener molecule. Alternatively, anti-caking agent may refer to any composition which assists in content uniformity and uniform dissolution. Non-limiting examples of anti-caking agents include cream of tartar, calcium silicate, silicon dioxide, microcrystalline cellulose (Avicel, FMC BioPolymer, Philadelphia, Pa.), and tricalcium phosphate. In one embodiment, the anti-caking agents are present in the tabletop sweetener composition in an amount from about 0.001 to about 3% by weight of the tabletop sweetener composition.

In some embodiments, the sweetener compositions of any of the preceding aspects and embodiments thereof are encapsulated using typical means for encapsulating flavor or fragrance compounds. Non-limiting examples of such technology are set forth in U.S. Patent Application Publication Nos. 2016/0235102, 2019/0082727, 2018/0369777, 2018/0103667, 2016/0346752, 2015/0164117, 2014/0056836, 2012/0027866, 2010/0172945, and 2007/0128234, as well as U.S. Pat. Nos. 7,488,503, 6,416,799, 5,897,897, 5,786,017, 5,603,971, 4,689,235, 4,610,890, 3,704,137, 3,041,180, and 2,809,895. All of the preceding patent publications and patents are hereby incorporated by reference as though set forth herein in their entireties.

Methods of Preparation

The compounds disclosed herein may be synthesized by methods described below, or by modification of these methods. Ways of modifying the methodology include, among others, temperature, solvent, reagents etc., known to those skilled in the art. In general, during any of the processes for preparation of the compounds disclosed herein, it may be necessary or desirable to protect sensitive or reactive groups on any of the molecules concerned.

In certain aspects, the disclosure provides methods of forming malonyl steviol glycosides, comprising reacting a steviol glycoside with malonic acid in the presence of an enzyme to form a malonyl steviol glycoside. Any steviol glycoside can be used. In certain embodiments, the steviol glycoside is selected from the group consisting of: Rebaudioside A, Stevioside, Rebaudioside C, Rebaudioside D, Rebaudioside E, Rebaudioside M, Rebaudioside I, Rebaudioside F, Rebaudioside B, Rebaudioside C acid, Rubusoside, steviol monoside, Rebaudioside G, steviol dioside, and dulcoside A. Any suitable enzyme may be used. In some embodiments, the enzyme is a lipase. Suitable examples of lipases are Novozymes 435 or lipases from *Candida antarctica, Candida rugosa, Humicola lanuginosa, Pseudomonas cepacia, Rhizopus oryzae, Rhizomucor miehei, Moesziomyces rugulosus, Ustilago siamensis, Ustilago maydis, Candida cylindracea*, or *Candida rugose*. Other suitable lipases are lipases from *Pichia pastoris, Trichoderma reesei, Aspergillus niger, Penicillium camemberti, Mucor javanicus, Aspergillus oryzae, Hansenula polymorpha, Candida cylindracea, Candida rugose, Rhizopus niveus, Penicillium roqueforti*, or *Rhizopus oryzae*. Any suitable malonyl compound can result from the method. In some embodiments, the malonyl steviol glycoside is: 6-O-malonyl Rebaudioside A, 6-O-malonyl Stevioside, 6-O-malonyl Rebaudioside C, 6-O-malonyl Rebaudioside D, 6-O-malonyl Rebaudioside E, 6-O-malonyl Rebaudioside M, 6-O-malonyl Rebaudioside I, 6-O-malonyl Rebaudioside F, 6-O-malonyl Rebaudioside B, 6-O-malonyl Rebaudioside C acid, 6-O-malonyl Rubusoside, 6-O-malonyl steviol monoside, 6-O-malonyl Rebaudioside G, 6-O-malonyl steviol dioside, or 6-O-malonyl dulcoside A.

EXAMPLES

To further illustrate this invention, the following examples are included. The examples should not, of course, be construed as specifically limiting the invention. Variations of these examples within the scope of the claims are within the purview of one skilled in the art and are considered to fall within the scope of the invention as described, and claimed herein. The reader will recognize that the skilled artisan, armed with the present disclosure, and skill in the art is able to prepare and use the invention without exhaustive examples.

Example 1—Extraction and Isolation of Compounds 101 and 102

Figure 2:
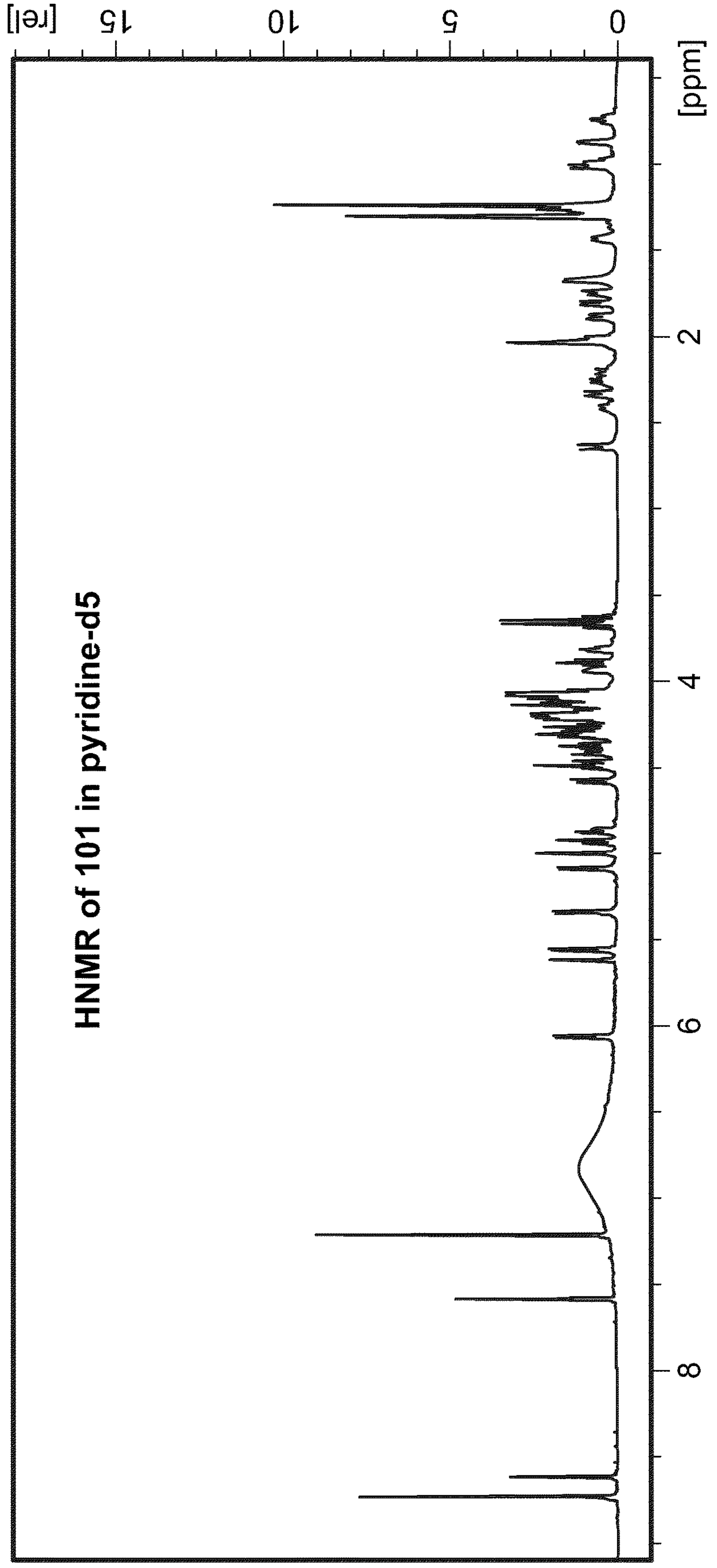
FIG. 2 shows the $^1$H NMR spectrum for Compound 101.
Figure 3:
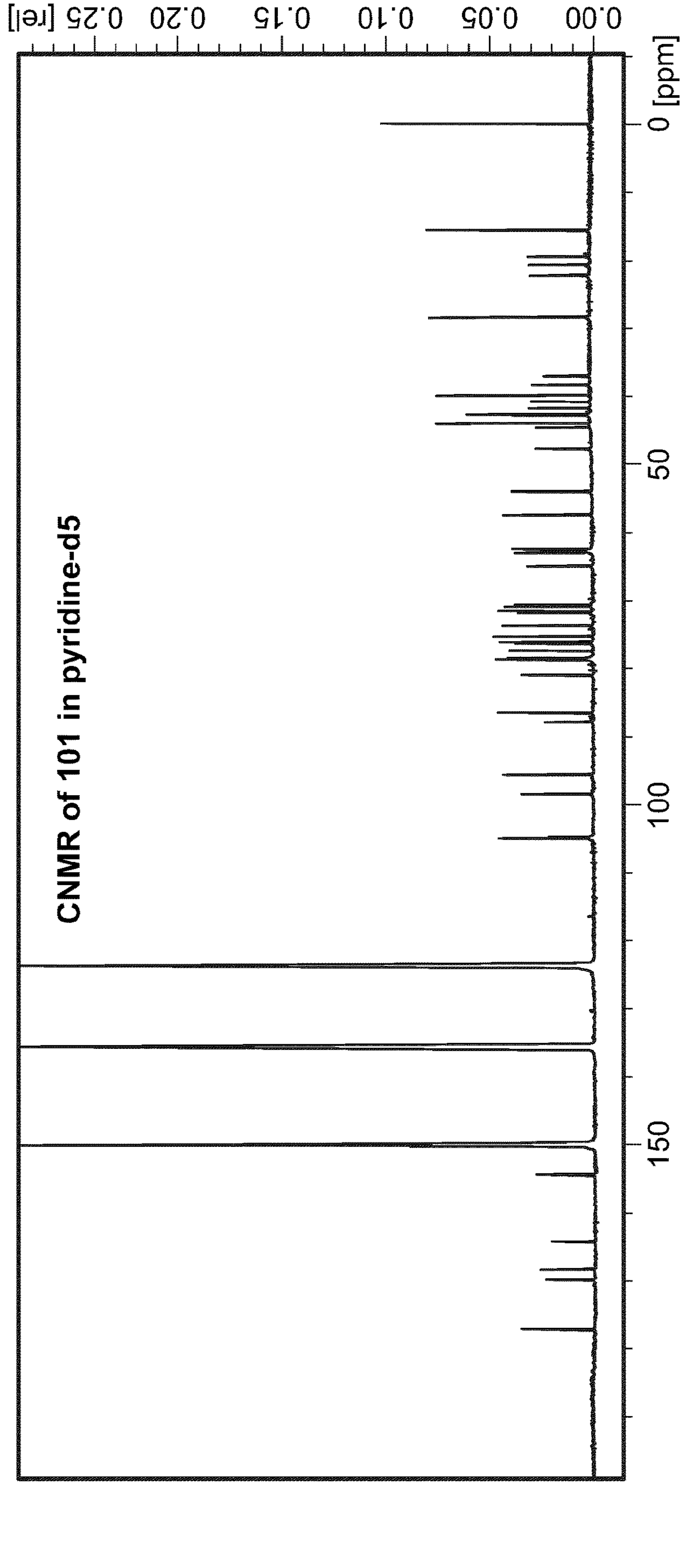
FIG. 3 shows the $^{13}$C NMR spectrum for Compound 101.
Figure 4:
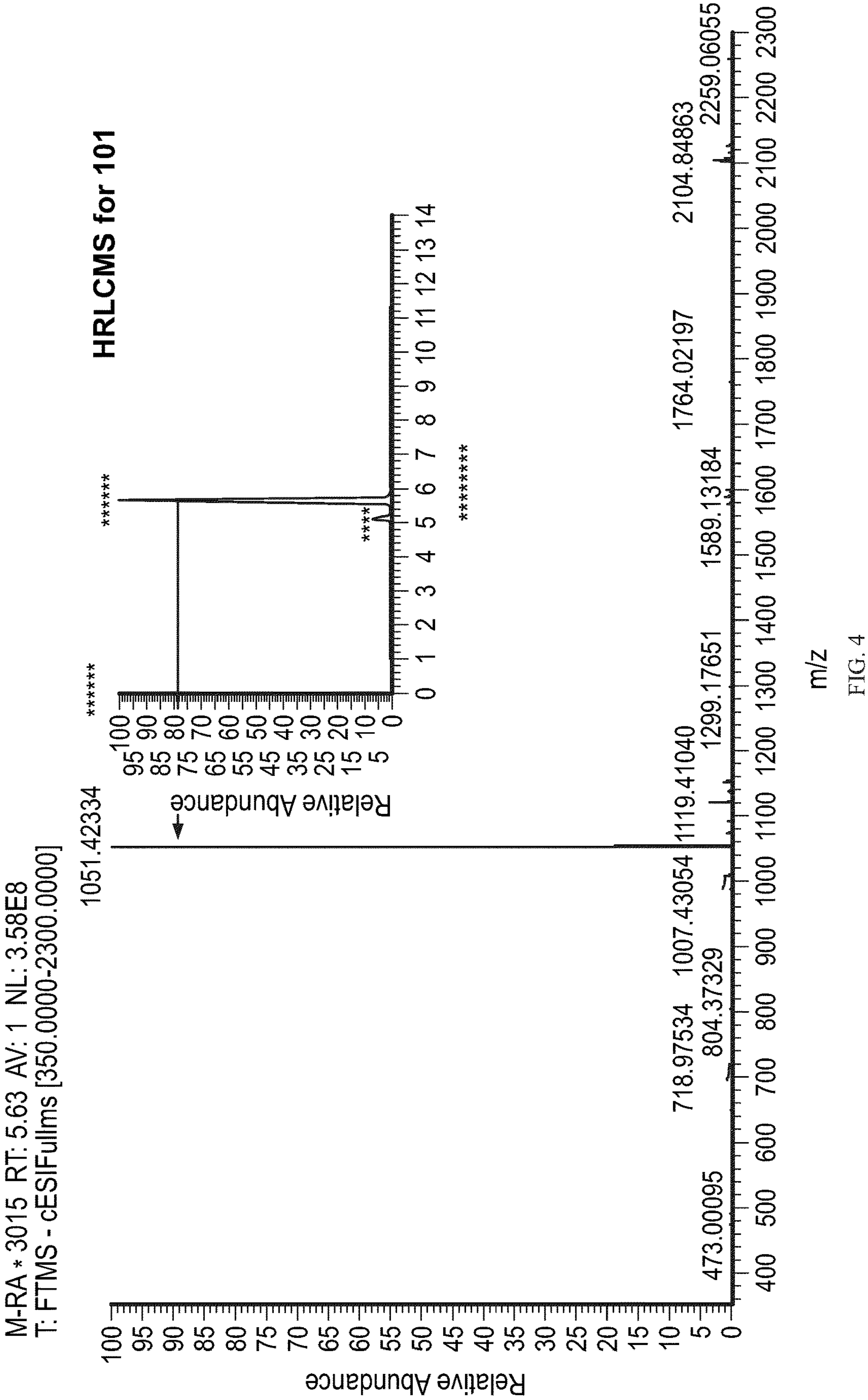
FIG. 4 shows the readout for the high-resolution HPLC for Compound 101.

The fresh leaves of *Stevia rebaudiana* (300 g) were extracted three times with 50% v/v ethanol/water. The combined extraction was filtrated and concentrated under reduced pressure at 50° C. by Rotavapor. The residue (~30 g) was suspended in water and loaded on a 330-gram XAD resin column. The system subsequently eluted with acidic aqueous ethanol of 10%, 30% and 60% to yield three fractions (F1-F3). Fraction F2 was further chromatographed on reverse phase (C18) preparative HPLC. Solvent system included A: water and B: acetonitrile, buffered with 0.1% of formic acid. A gradient program from 30% B to 40% B was used. Main peak of malonyl RebA was collected. 200 mg of Compound 101 was obtained and determined as 6'-O-malonyl Rebaudioside A by NMR and HRESIMS analysis. FIG. 2 shows the $^1$H NMR spectrum for Compound 101. FIG. 3 shows the $^{13}$C NMR spectrum for Compound 101. FIG. 4 shows the readout for the high-resolution HPLC for Compound 101.

Figure 5:
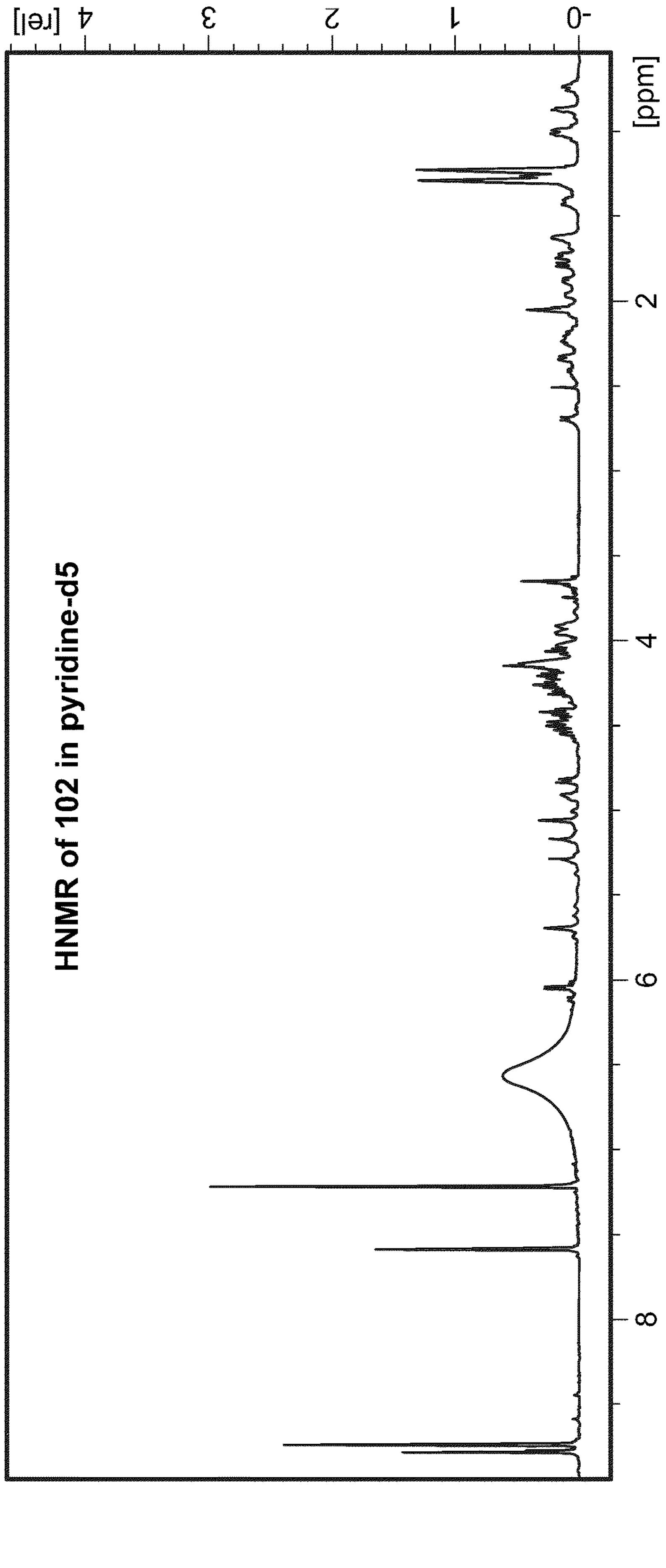
FIG. 5 shows the $^1$H NMR spectrum for Compound 102.
Figure 6:
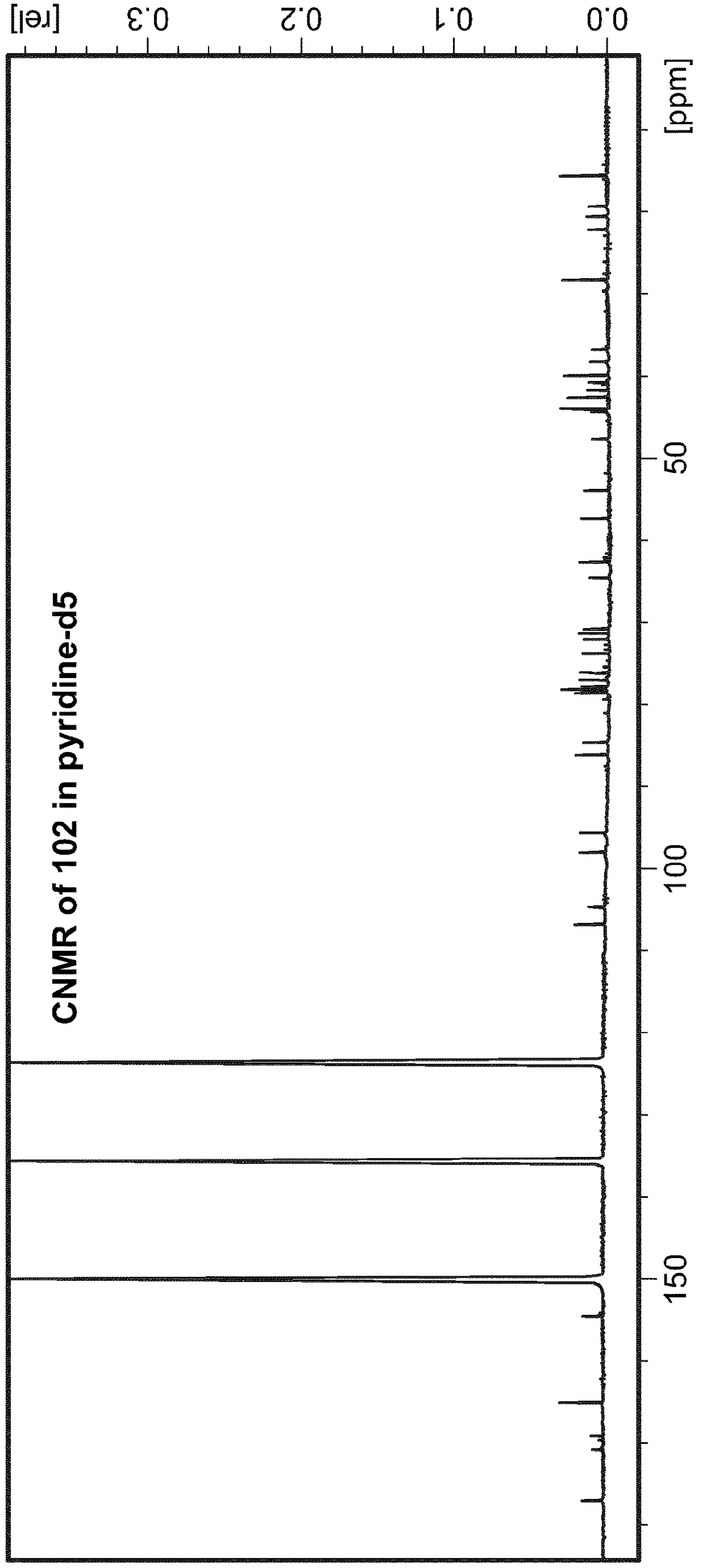
FIG. 6 shows the $^{13}$C NMR spectrum for Compound 102.
Figure 7:
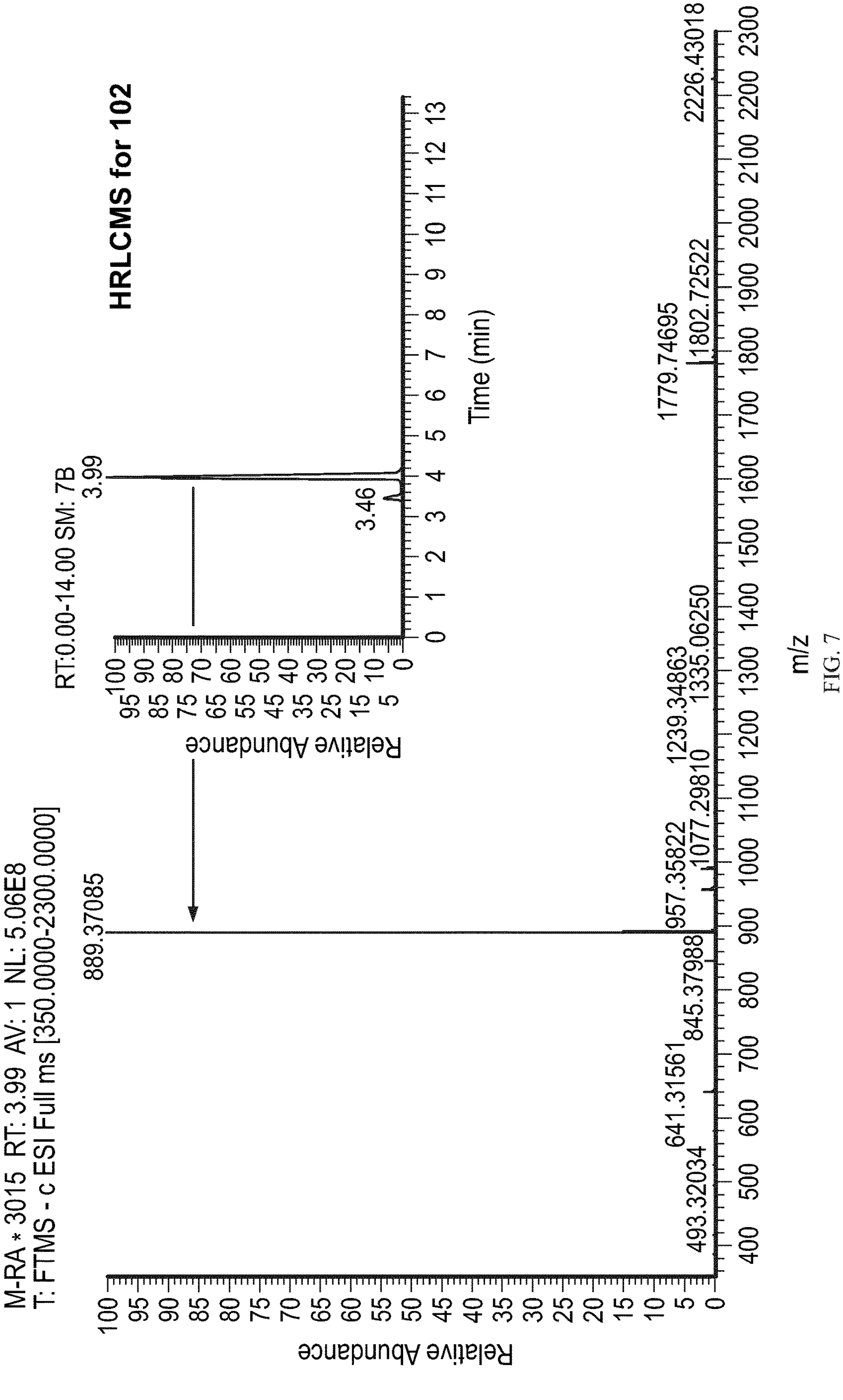
FIG. 7 shows the readout for the high-resolution HPLC for Compound 102.

The dry leaves of *Stevia rebaudiana* (300 g) were extracted three times with 50% v/v ethanol/water. The combined extraction was filtrated and concentrated under reduced pressure at 40° C. by Rotavapor. Part of the residue (~50 g) was suspended in water and loaded on a 330-gram MCI resin column. The system subsequently eluted with acidic aqueous ethanol of 10%, 30% and 60% to yield three fractions (F1-F3). Fraction F2 was used for further purification on reverse phase (C18) preparative HPLC. Solvent system included A: water and B: acetonitrile, both with 0.10% of formic acid. Eluted starting from 30% B and end with 40% B. Main peak of malonyl Stevioside was collected. 100 mg of Compound 102 was obtained and determined as 6'-O-malonyl stevioside by NMR and HRESIMS analysis. FIG. 5 shows the $^1$H NMR spectrum for Compound 102. FIG. 6 shows the $^{13}$C NMR spectrum for Compound 102. FIG. 7 shows the readout for the high-resolution HPLC for Compound 102.

Example 2—Enzymatic Synthesis of Compounds 103-106

Figure 8:
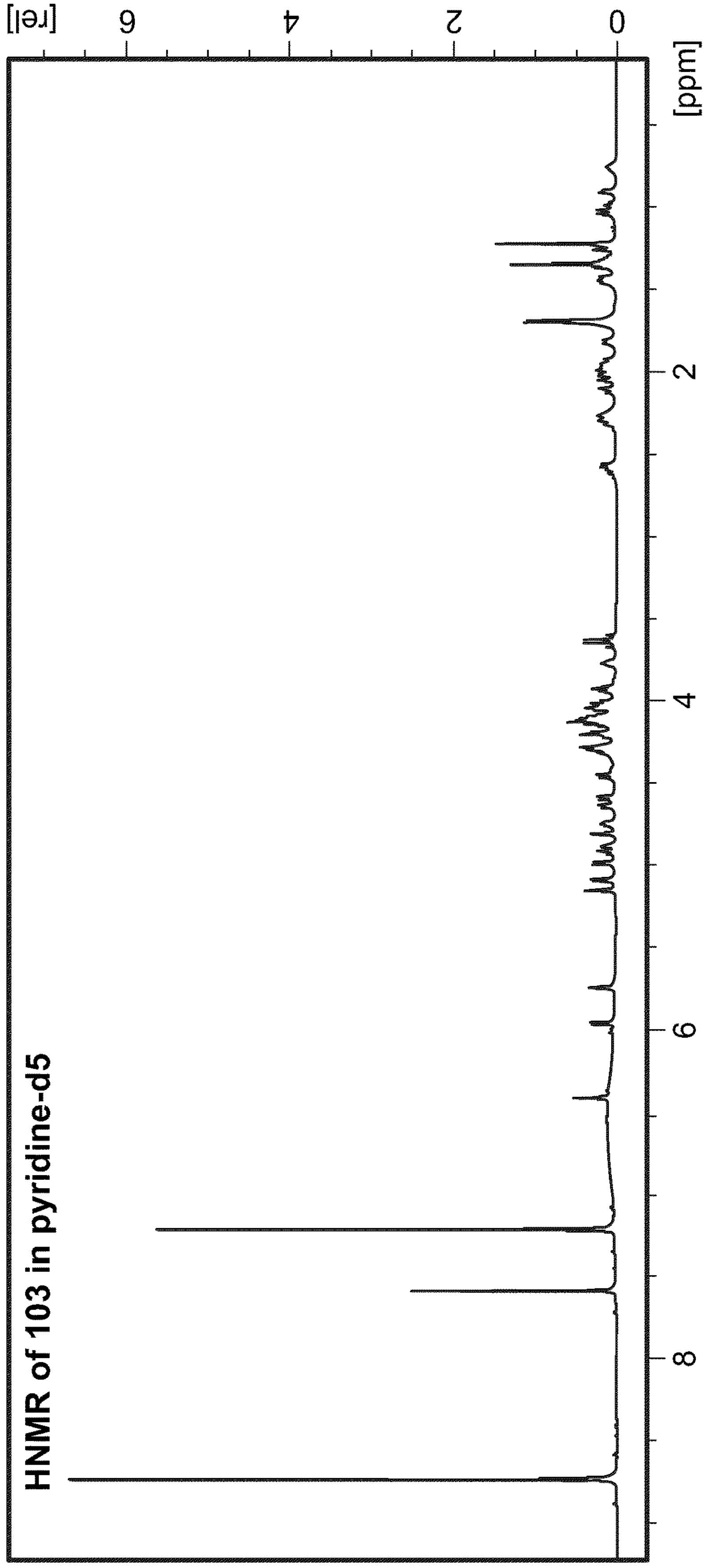
FIG. 8 shows the $^1$H NMR spectrum for Compound 103.
Figure 9:
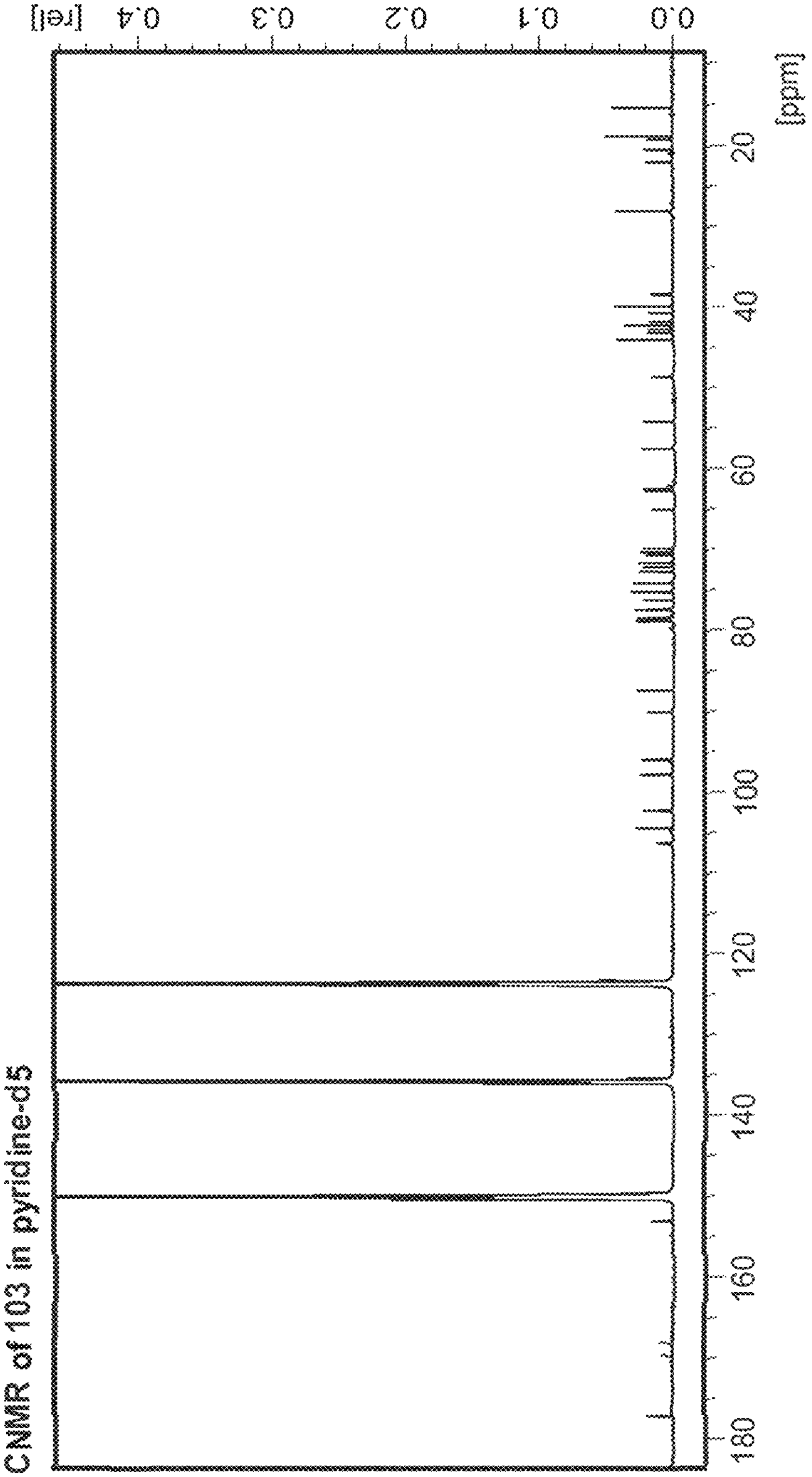
FIG. 9 shows the $^{13}$C NMR spectrum for Compound 103.
Figure 10:
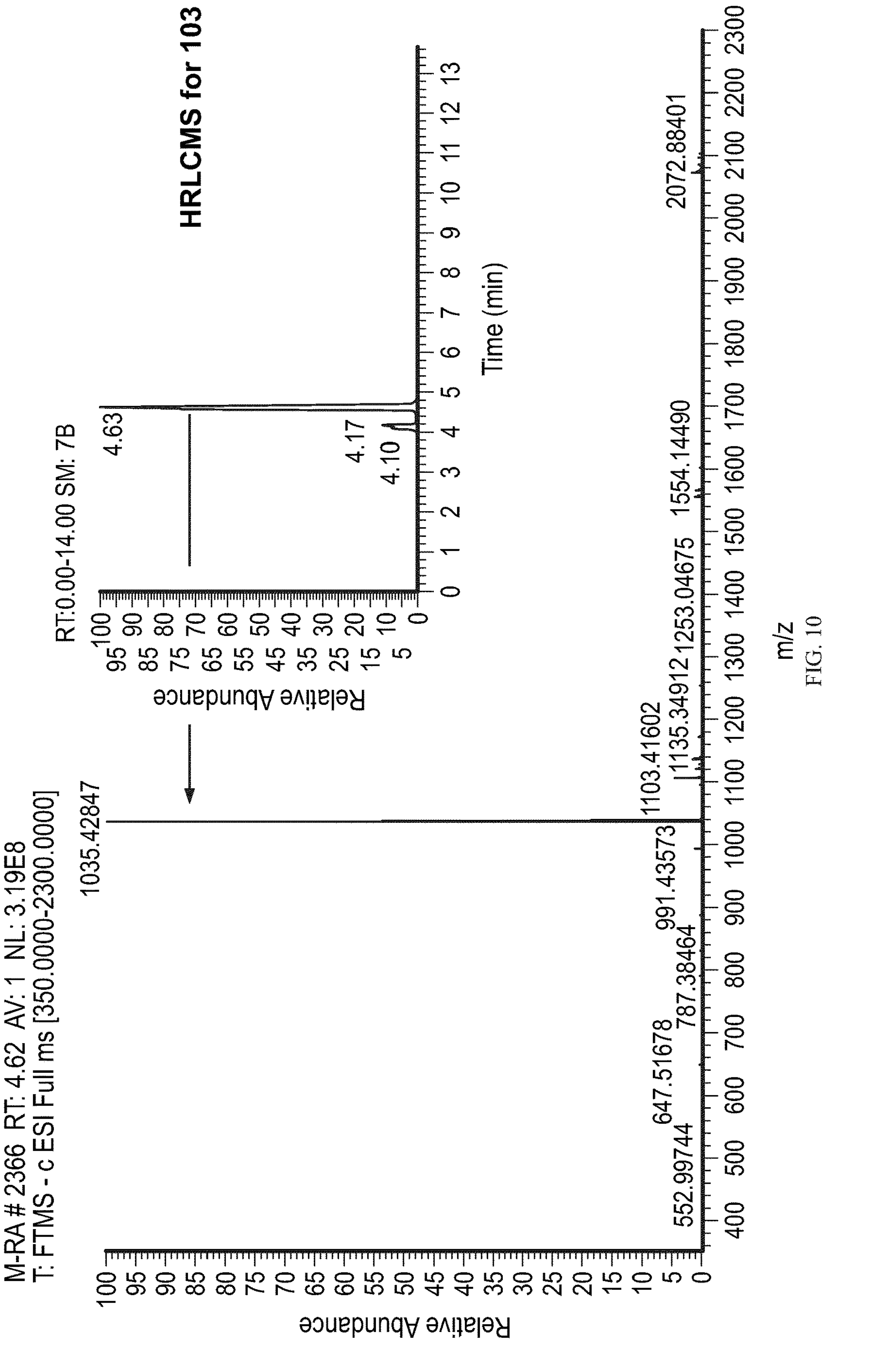
FIG. 10 shows the readout for the high-resolution HPLC for Compound 103.

Rebaudioside C (2.4 g) was added into a 150-mL flask with malonic acid (2.6 g), activated molecular sieve (4 g) and dried t-butanol (100 mL). The mixture was stirred and heated to dissolve Rebaudioside C. After cooling, an enzyme (Novozyme 435) (2 g) was added and the reaction was stirred at 60° C. for 2 weeks in water bath. After the reaction was stopped, the mixture was filtered with paper and washed with water. The filtrate was evaporated and subjected to an ion-exchange SPE column (Agela PAX column) which was preconditioned with 1% $NH_3$—$H_2O$. The column was washed by methanol with 1% $NH_3$ and water, eluted with 1% formic acid aqueous solution (F1) and 1% formic acid in 30% methanol aqueous solution (F2). The F2 fraction was collected and purified via the prep-HPLC system by using 40% v/v acetonitrile/water solution with 0.1% formic acid. The collected major product was concentrated to dry to obtain 65 mg 6'-malonyl rebaudioside C (Compound 103). FIG. 8 shows the $^1$H NMR spectrum for Compound 103. FIG. 9 shows the $^{13}$C NMR spectrum for Compound 103. FIG. 10 shows the readout for the high-resolution HPLC for Compound 103.

Figure 11:
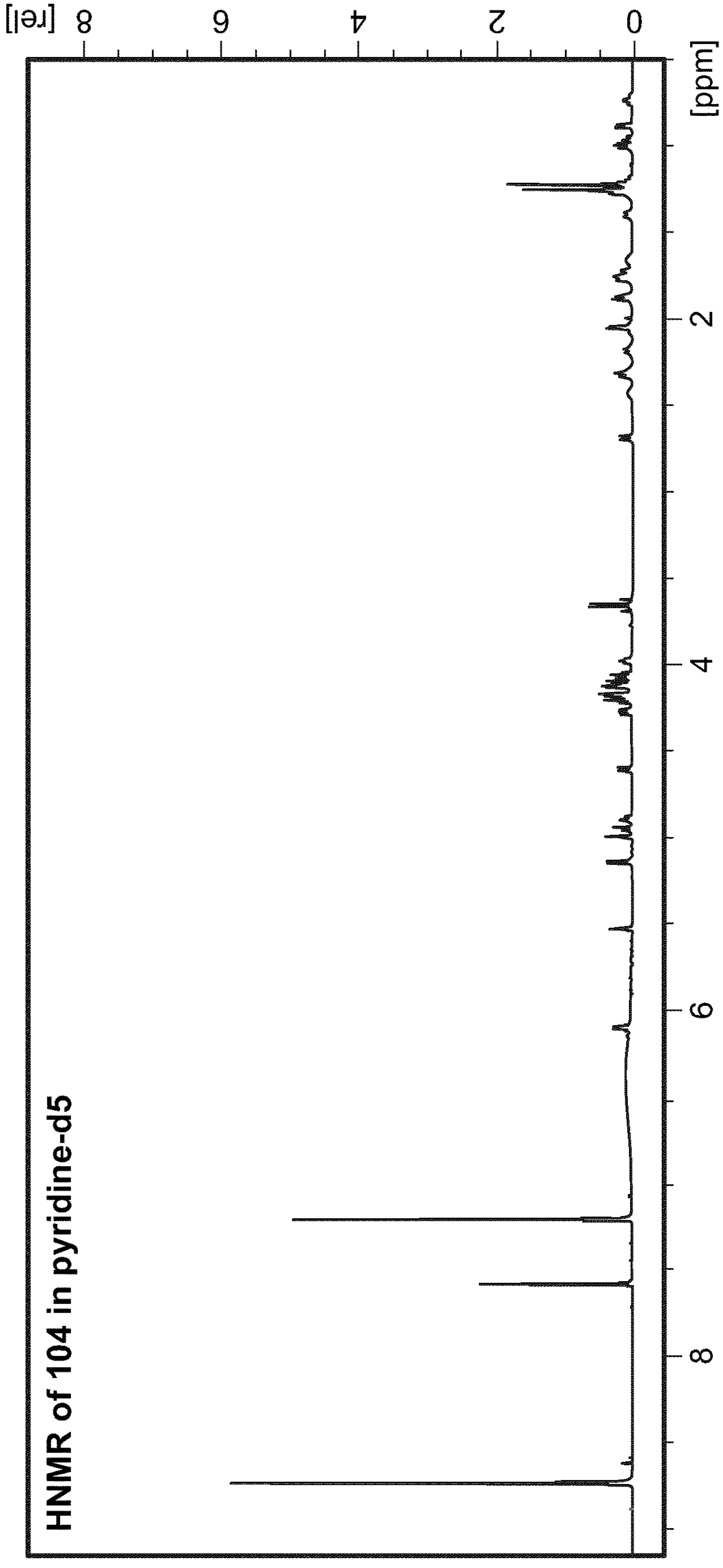
FIG. 11 shows the $^1$H NMR spectrum for Compound 104.
Figure 12:
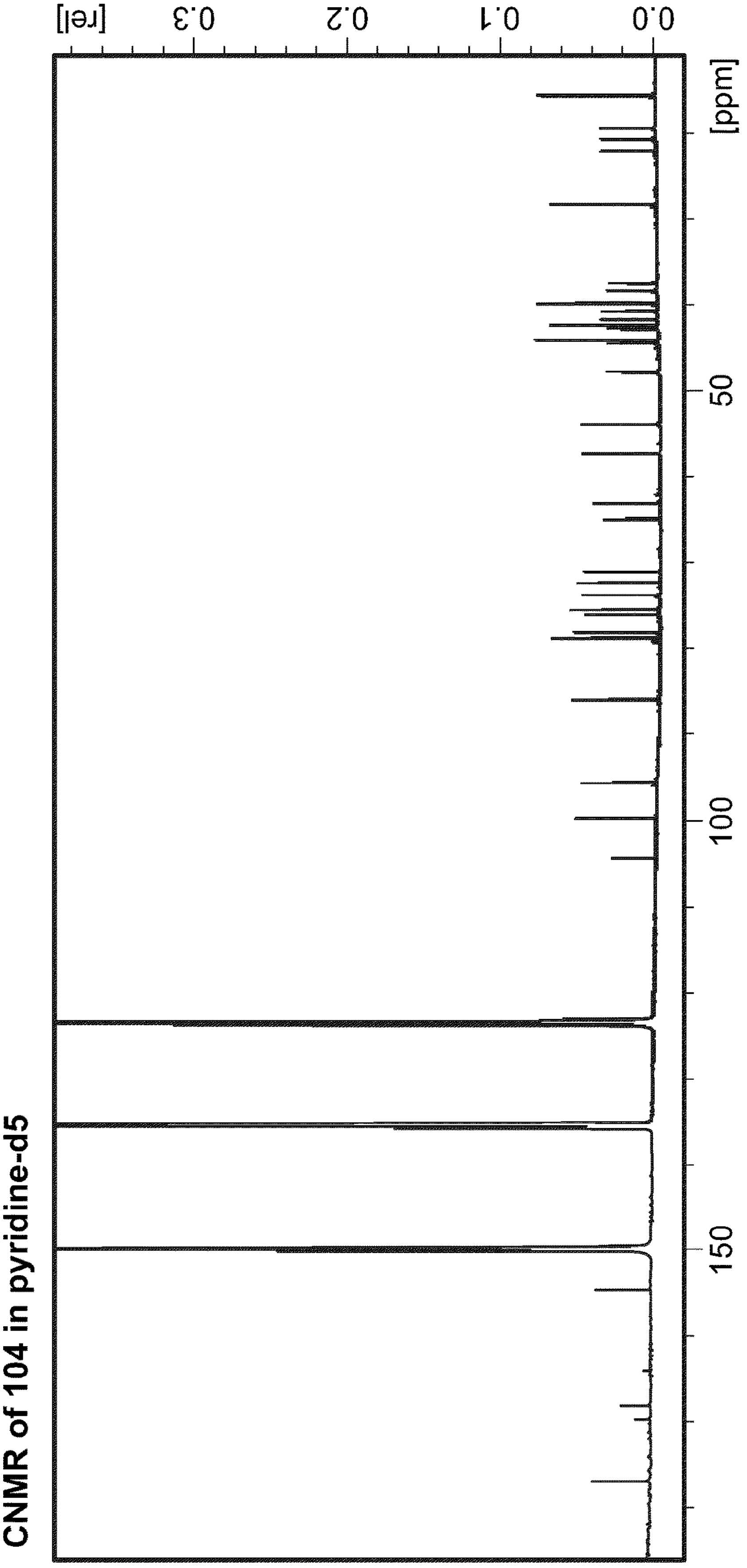
FIG. 12 shows the $^{13}$C NMR spectrum for Compound 104.
Figure 13:
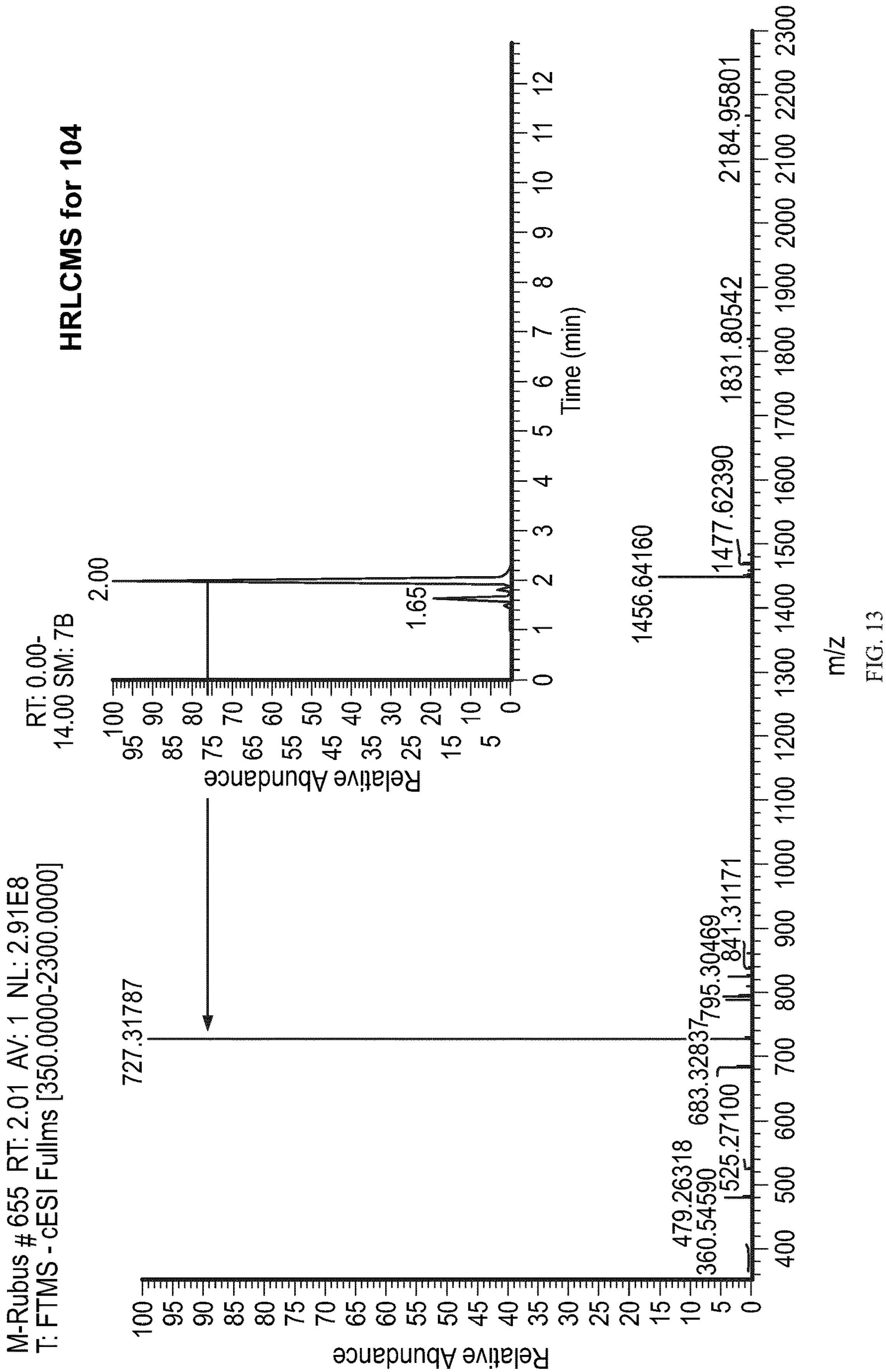
FIG. 13 shows the readout for the high-resolution HPLC for Compound 104.

Rubusoside (1.6 g) was added into a 150-mL flask with malonic acid (2.6 g), sieve-dried t-butanol (100 mL). The enzyme (Novozyme 435) (2 g) was subsequently added and the reaction was stirred at 50° C. for 2 weeks in oil bath. After the reaction was cooled, the mixture was filtered and washed with water. The filtrate was concentrated and subjected to an ion-exchange SPE column (Waters Oasis MAX column) which was preconditioned with 1% $NH_3$—$H_2O$. The column was washed by methanol with 1% $NH_3$ and water, eluted with 1% formic acid aqueous solution (F1) and 1% formic acid in 30% methanol aqueous solution (F2). The F2 fractions were collected and purified via the prep-HPLC system with a gradient B from 30% to 40%, where solvent A is water with 0.10% formic acid and solvent B was acetonitrile with 0.1% formic acid. The collected fraction was evaporated and freeze dried. 100 mg 6'-O-malonyl rubusoside (Compound 104) was obtained. FIG. 11 shows the $^1$H NMR spectrum for Compound 104. FIG. 12 shows the $^{13}C$ NMR spectrum for Compound 104. FIG. 13 shows the readout for the high-resolution HPLC for Compound 104.

Figure 14:
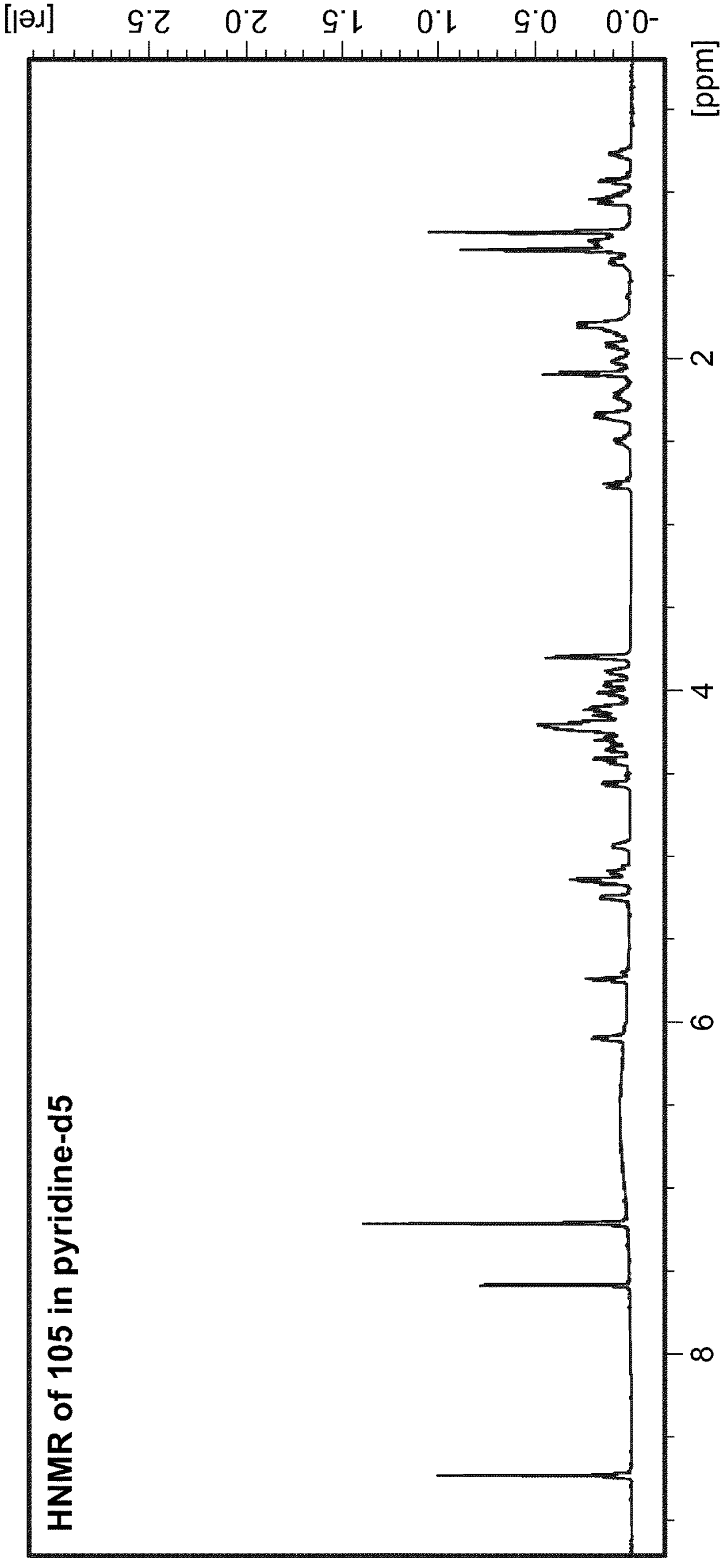
FIG. 14 shows the $^1$H NMR spectrum for Compound 105.
Figure 15:
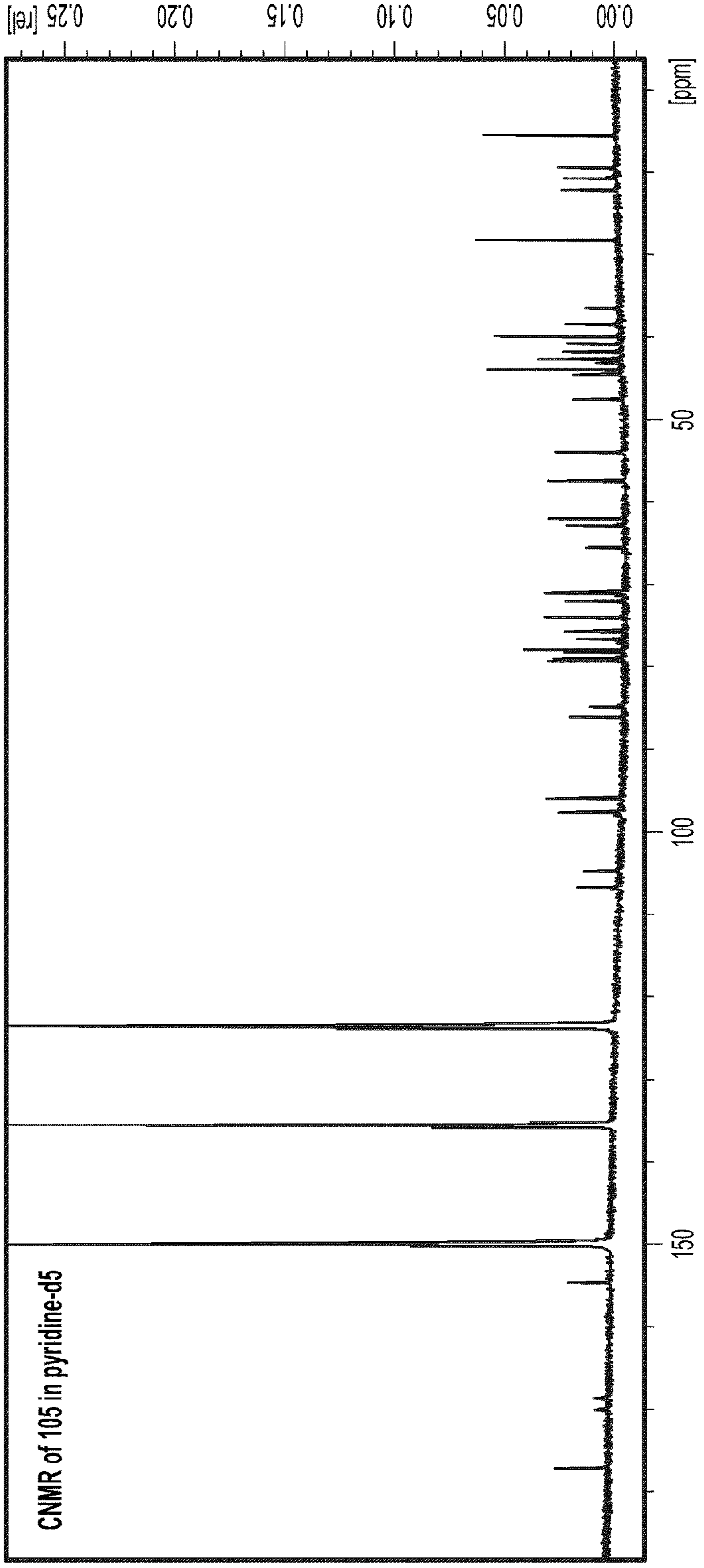
FIG. 15 shows the $^{13}$C NMR spectrum for Compound 105.
Figure 16:
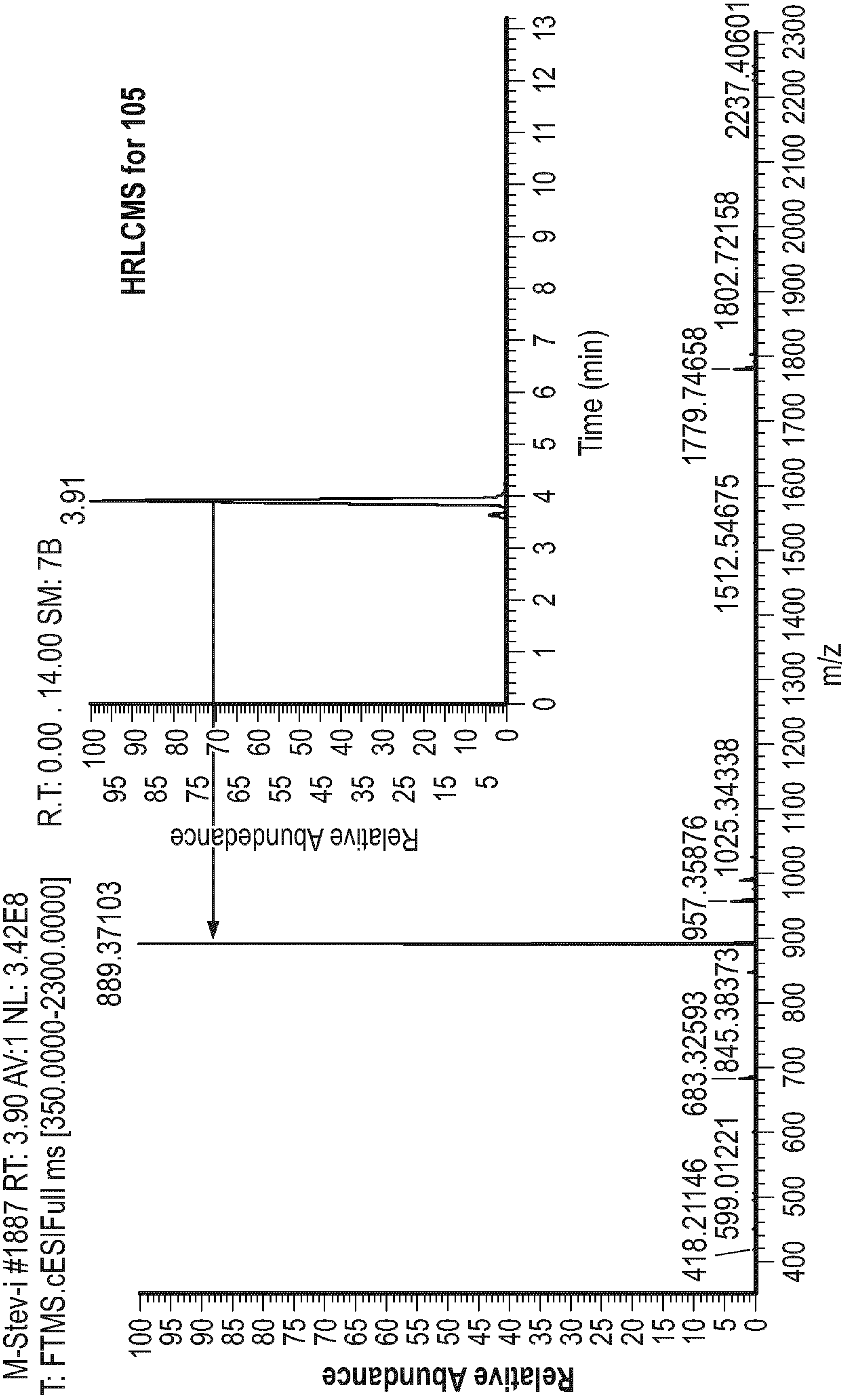
FIG. 16 shows the readout for the high-resolution HPLC for Compound 105.

Stevioside (2.0 g) was added into a 150-mL flask with malonic acid (2.6 g) dried t-butanol (100 mL). The enzyme (Novozyme 435) (2 g) was subsequently added and the reaction was stirred at 55° C. for 2 weeks in oil bath. After the reaction was stopped, the mixture was filtered and washed with water. The filtrate was concentrated and purified via the prep-HPLC system with a gradient B from 30% to 40%, where solvent A is water with 0.1% formic acid and solvent B was acetonitrile with 0.1% formic acid. The collected fraction was evaporated and freeze dried. 65 mg 6'''-O-malonyl stevioside (Compound 105) was obtained. FIG. 14 shows the $^{1}H$ NMR spectrum for Compound 105. FIG. 15 shows the $^{13}C$ NMR spectrum for Compound 105. FIG. 16 shows the readout for the high-resolution HPLC for Compound 105.

Figure 17:
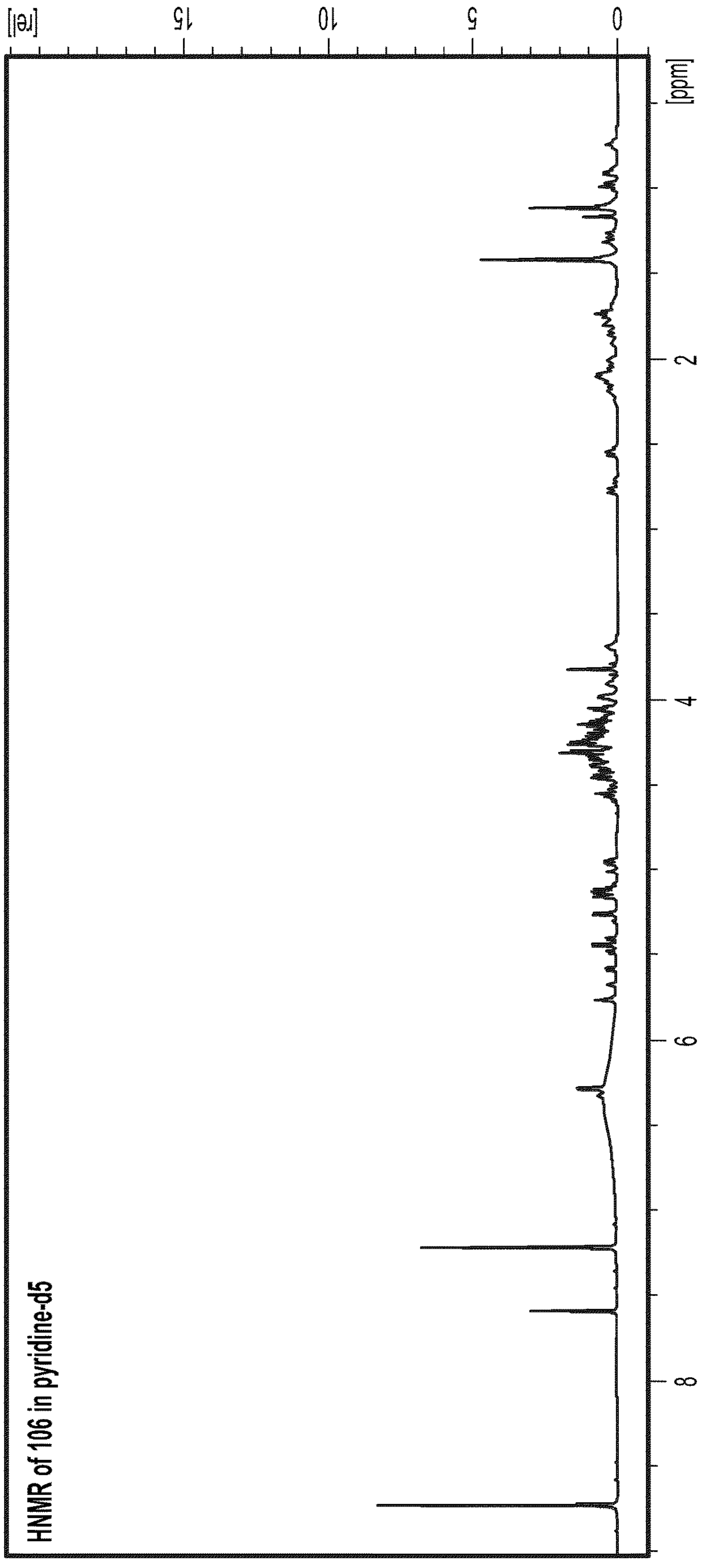
FIG. 17 shows the $^1$H NMR spectrum for Compound 106.
Figure 18:
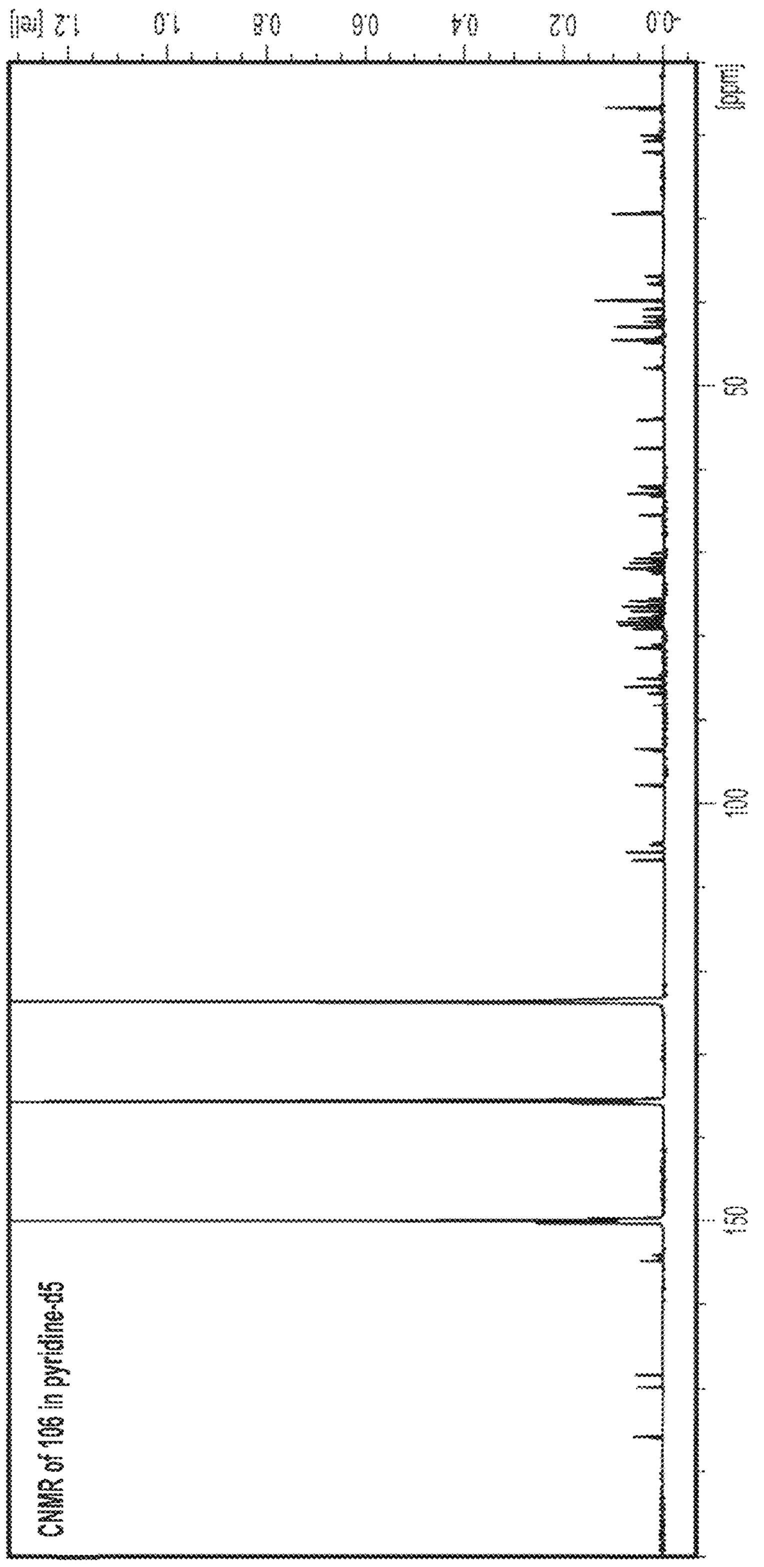
FIG. 18 shows the $^{13}$C NMR spectrum for Compound 106.
Figure 19:
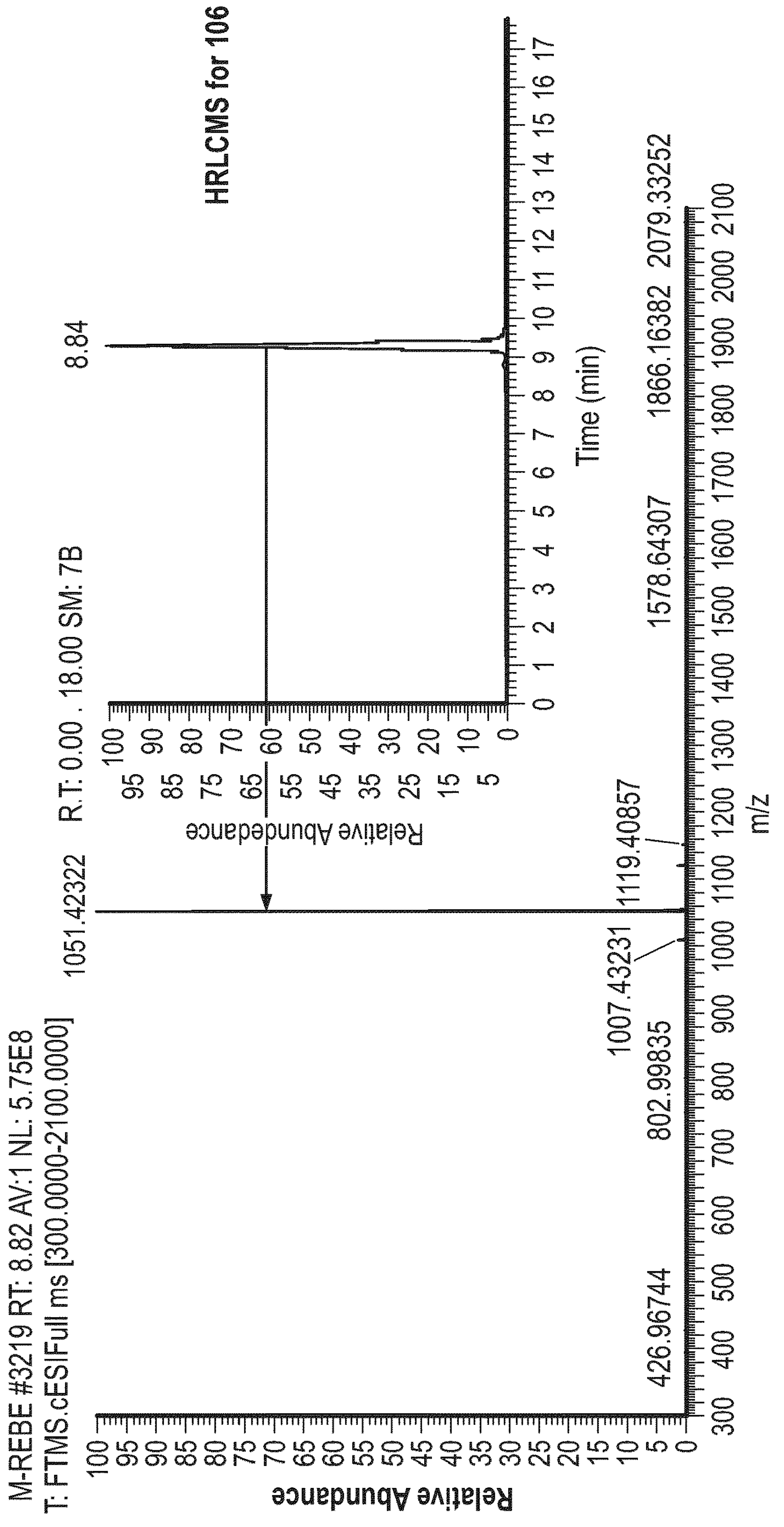
FIG. 19 shows the readout for the high-resolution HPLC for Compound 106.
Figure 20:
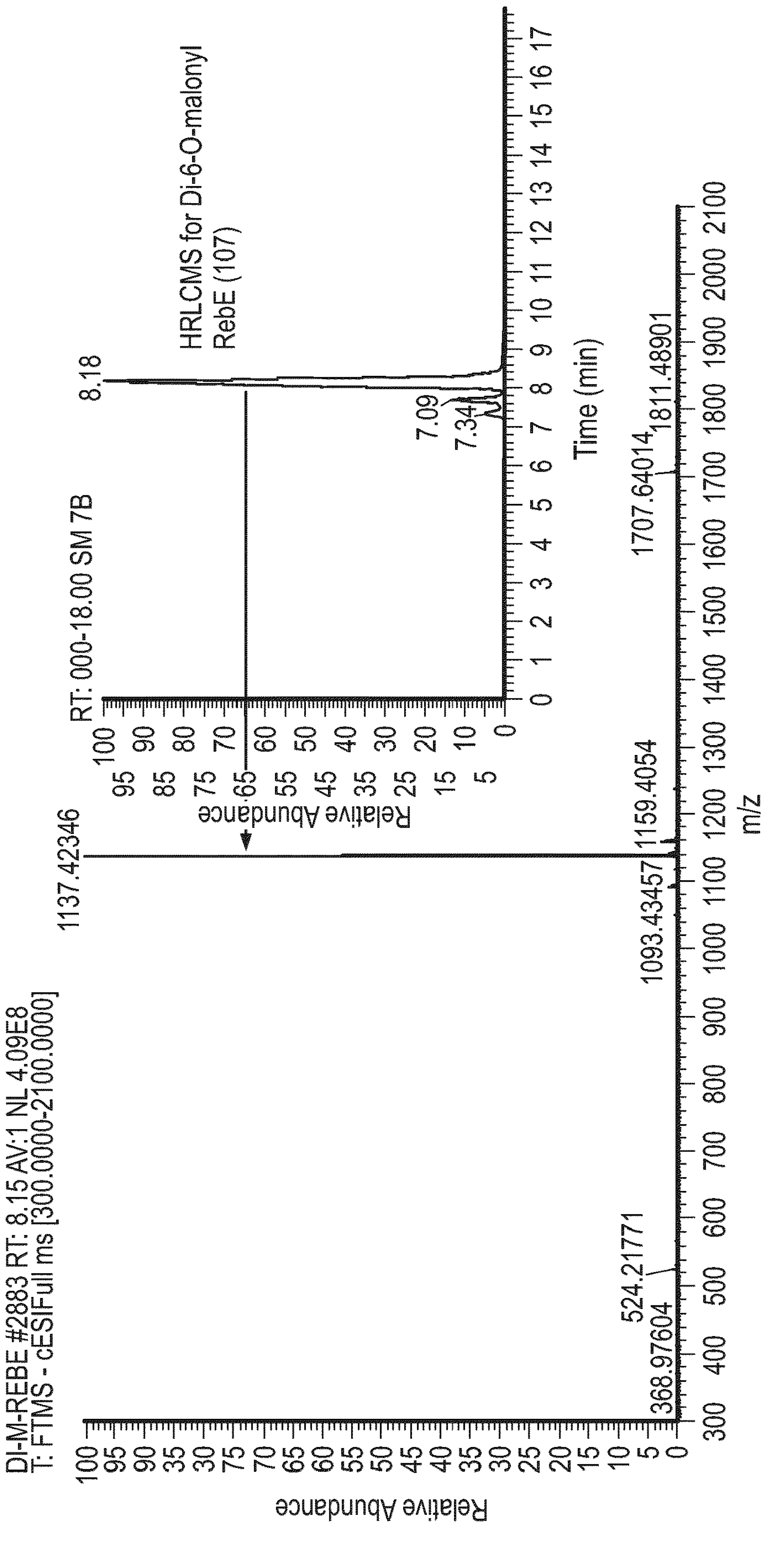
FIG. 20 shows the readout for the high-resolution HPLC for Compound 107.

Rebaudioside E (2.0 g) was added into a 500-mL flask with malonic acid (2.1 g), 4A molecular seives (20 g) and dried t-butanol (200 mL). The enzyme (Novozyme 435) (4.0 g) was subsequently added and the reaction was stirred at 55° C. for one week in oil bath. After the reaction was stopped, the mixture was filtered and washed with water. The filtrate was concentrated and purified via the prep-HPLC system with a gradient B from 29% to 32%, where solvent A is water with 0.10% formic acid and solvent B was acetonitrile with 0.10% formic acid. The collected fraction was evaporated and freeze dried. 240 mg 6''''-O-malonyl rebaudioside E (Compound 106) was obtained as well as 30 mg of Di-6-O-malonyl rebaudioside E (Compound 107) were obtained. FIG. 17 shows the $^{1}H$ NMR spectrum for Compound 106. FIG. 18 shows the $^{13}C$ NMR spectrum for Compound 106. FIG. 19 shows the readout for the high-resolution HPLC for Compound 106. FIG. 20 shows the readout for the high-resolution HPLC for Compound 107.

Example 3—Enzymatic Synthesis of Other Malyonyl Steviol Glycosides

Following procedures analogous to those of Examples 1 and 2, many other malonyl steviol glycosides are prepared. These include 6-O-malonyl Rebaudioside A, 6-O-malonyl Stevioside, 6-O-malonyl Rebaudioside C, 6-O-malonyl Rebaudioside D, 6-O-malonyl Rebaudioside E, 6-O-malonyl Rebaudioside M, 6-O-malonyl Rebaudioside I, 6-O-malonyl Rebaudioside F, 6-O-malonyl Rebaudioside B, 6-O-malonyl Rebaudioside C acid, 6-O-malonyl Rubusoside, 6-O-malonyl steviol monoside, 6-O-malonyl Rebaudioside G, 6-O-malonyl steviol bioside, and 6-O-malonyl dulcoside A. Chemical identity is confirmed by HRESIMS and MS/MS analysis.

Figure 21:
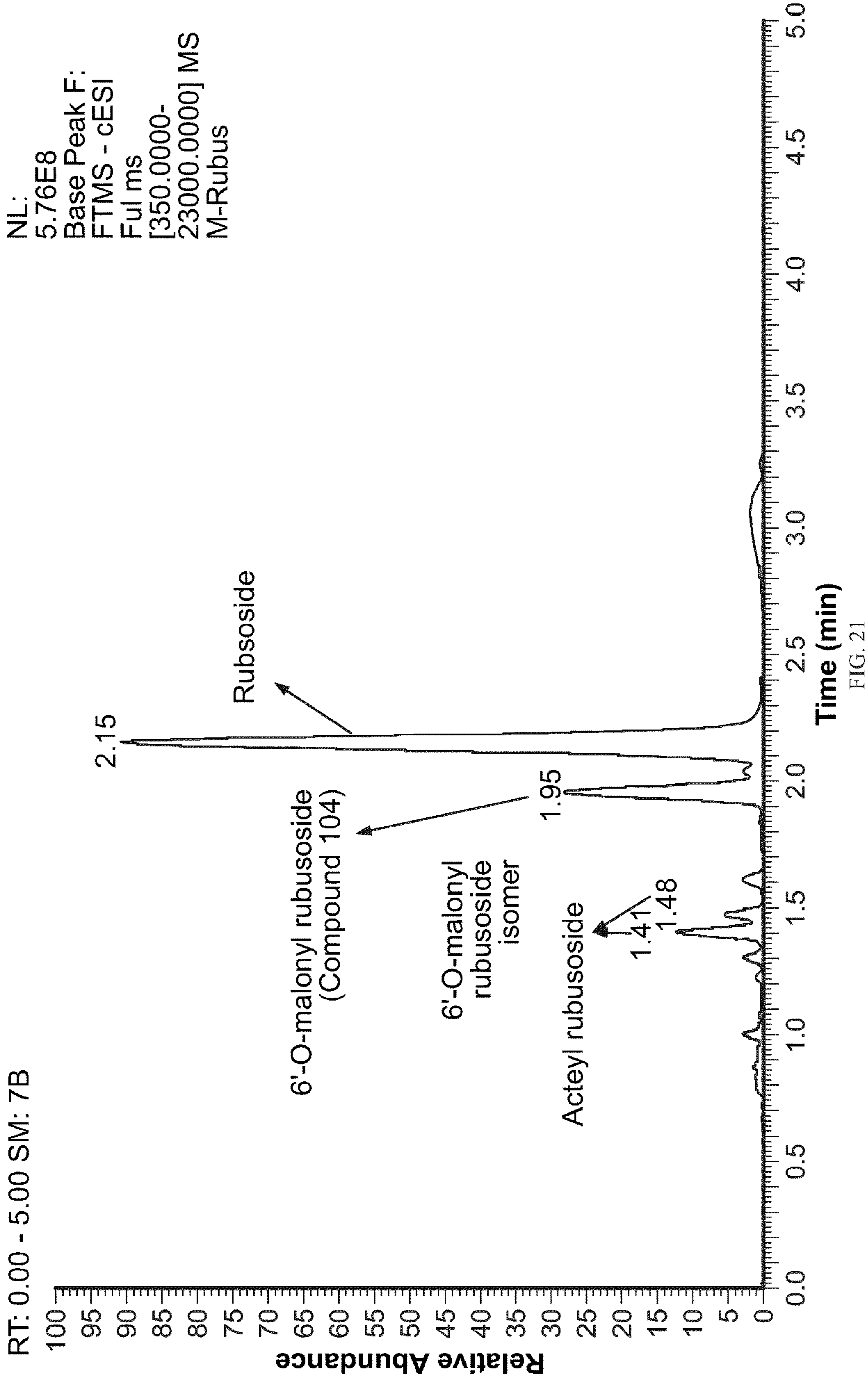
FIG. 21 shows the readout for the high-resolution HPLC for the malonylated rubusoside product.

Example 4—Enzymatic Synthesis of Malonylated Rubusoside Product, Malonylated Rebaudioside E Product, Malonylated Steviol Glycoside Product Rubusoside (2.0 g) was added into a 500-mL flask with malonic acid (3.0 g), 4A molecular seives (20 g) and dried t-butanol (200 mL). The enzyme (Novozyme 435) (4.0 g) was subsequently added and the reaction was stirred at 50° C. for one week in oil bath. After the reaction was stopped, the mixture was filtered and washed with water. The filtrate was concentrated and subjected to an SPE column (Waters HLB column) which was preconditioned. The column was eluted with 0.1% formic acid aqueous solution (F1) and 0.1% formic acid in 70% ethanol aqueous solution (F2). The F2 fractions were concentrated and subjected to an ODS column. The column was eluted with 0.1% formic acid aqueous solution (F2-1) and 0.1% formic acid in 50% ethanol aqueous solution (F2-2). After removing the ethanol, the product aqueous solution was freeze dried to give malonylate rubusoside product which contains around 310% malonyl rubusosides in product (peak area percentage of MS chromatogram). FIG. 21 shows the readout for the high-resolution HPLC for the malonylated rubusoside product.

Figure 22:
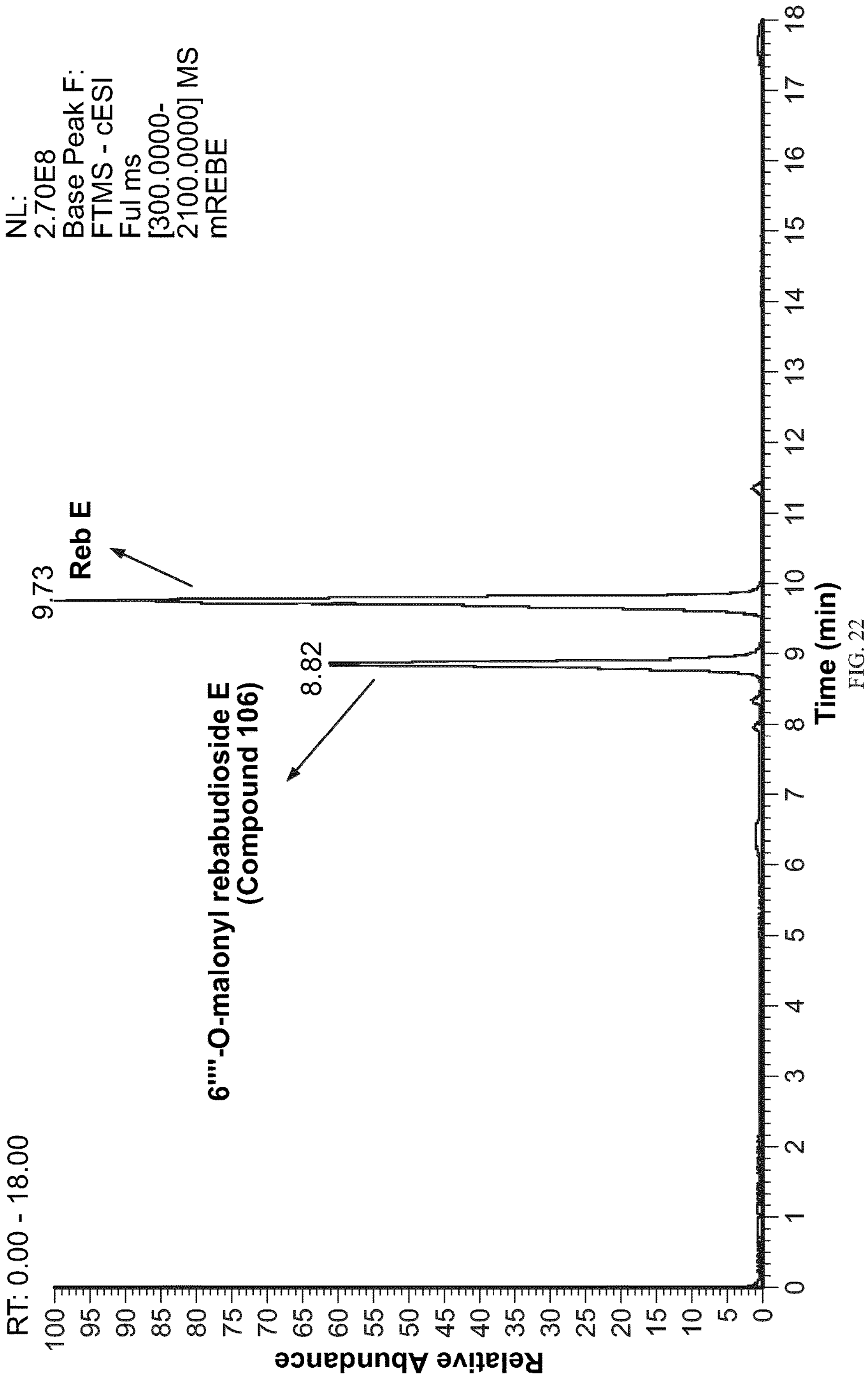
FIG. 22 shows the readout for the high-resolution HPLC for the malonylated rebaudioside E product.

Rebaudioside E (RebE, 2.0 g) was added into a 500-mL flask with malonic acid (2.1 g), 4A molecular seives (20 g) and dried t-butanol (200 mL). The enzyme (Novozyme 435) (4.0 g) was subsequently added and the reaction was stirred at 55° C. for one week in oil bath. After the reaction was stopped, the mixture was filtered and washed with water. The filtrate was concentrated and subjected to an MCI column. The column was initially washed with 0.1% formic acid aqueous solution (F1) and then eluted 0.1% formic acid in 50% ethanol aqueous solution (F2). After removing the ethanol, the product aqueous solution was freeze dried to give malonylated Reb E product which contains 39% malonyl Reb E in product (peak area percentage of MS chromatogram). FIG. 22 shows the readout for the high-resolution HPLC for the malonylated rebaudioside E product.

Figure 23:
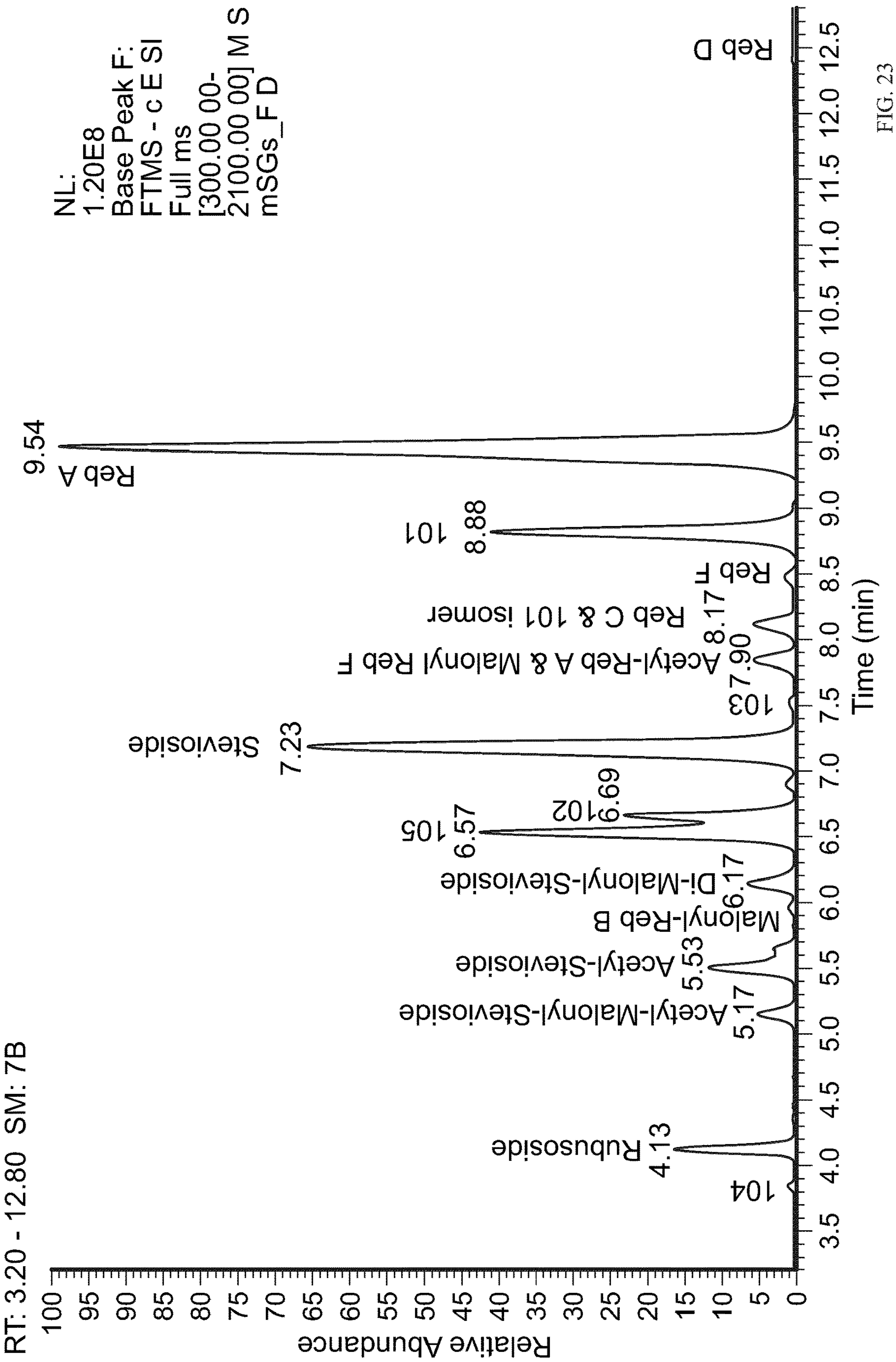
FIG. 23 shows the readout for the high-resolution HPLC for the malonylated steviol glycoside product.

*Stevia* Glycoside Extract SG95-RA60 (2.0 g) was added into a 500-mL flask with malonic acid (2.0 g), 4A molecular seives (10 g) and dried t-butanol (180 mL). The enzyme (Novozyme 435) (4.0 g) was subsequently added and the reaction was stirred at 53° C. for one week in oil bath. After the reaction was stopped, the mixture was filtered and washed with water. The filtrate was concentrated and subjected to an MCI column. The column was initially washed with 0.1% formic acid aqueous solution (F1) and then eluted 0.1% formic acid in 50% ethanol aqueous solution (F2). After removing the ethanol, the product aqueous solution was freeze dried to give malonylated steviol glycosides product which contain 31% total malonyl *Stevia* glycosides in product (peak area percentage of MS chromatogram). FIG. 23 shows the readout for the high-resolution HPLC for the malonylated steviol glycoside product.

Example 5—Sensory Testing

Malonyl glycosides 101, 102, 104 and 105 were evaluated in water solution at two selected dosages (62.5 ppm and 250 ppm) to identify their sweet capacity. Ten experts were asked to evaluate sweet, licorice, and sweet lingering intensities on a linear scale. Then, the dosage for equal sweet intensity from sucrose was identified. Sweet capacity for each compound was calculated based on dosage difference between tested compound and sucrose.

Compound 101 was determined to be about 150 times sweeter than sucrose. Compound 102 was determined to be about 150 times sweeter than sucrose. Compound 104 was determined to be about 120 times sweeter than sucrose. Compound 105 was determined to be about 100 times sweeter than sucrose.

Compound 101 was evaluated as a sweet modifier in SG95 (PureCircle) base at 30 ppm. Seven experts were asked to compare the intensity difference between reference (SG95 base) and Compound 101 was added to the sample. The taste properties (such as sweet, licorice, sweet lingering) were evaluated on a scale of −5 to 5 (−5 denoted strong masking effect and 5 denoted strong enhancing effect, 0 being the intensity of reference). Compound 101 was determined to have a sweet enhancement effect. It has exhibited better performance in licorice and sweet lingering masking than Rebaudioside A.

Compound 105 was evaluated as a sweet modifier in SG95 base at 30 ppm. Seven experts were asked to compare the intensity difference between reference (SG95 base) and Compound 105 was added sample. The taste properties (such as sweet, licorice, sweet lingering) were evaluated on a scale of −5 to 5 (−5 denoted strong masking effect and 5 denoted strong enhancing effect, 0 being the intensity of reference). Compound 105 was determined to have a sweet enhancement effect.

Compound 104 was evaluated as a sweet modifier in SG95 base at 30 ppm. Seven experts were asked to compare the intensity difference between reference (SG95 base) and Compound 104 adding sample. The taste properties (such as sweet, licorice, sweet lingering) were evaluated on a scale of −5 to 5 (−5 denoted strong masking effect and 5 denoted strong enhancing effect, 0 being the intensity of reference). Compound 104 was determined to have a sweet enhancement effect. It also performed well on tests for licorice and lingering masking effect.

Malonylated Rubusoside product obtained from Example 4 was evaluated as a sweet modifier in sucrose base or SG95 base at 30 ppm. Seven experts were asked to compare the intensity difference between reference (sucrose base or SG95 base or sucrose-citric acid base) and malonylated Rubusoside product_adding sample. The taste properties (such as sweet, licorice, sweet lingering and sour) were evaluated on a scale of −5 to 5 (−5 denoted strong masking effect and 5 denoted strong enhancing effect, 0 being the intensity of reference). Malonylated Rubusoside product was determined to have a sweet enhancement effect. It also performed slightly licorice and lingering enhancing effect in test.

Malonylated RebE product obtained from Example 4 was evaluated as a sweet modifier in sucrose base or SG95 base at 30 ppm. Seven experts were asked to compare the intensity difference between reference (sucrose base or SG95 base or sucrose-citric acid base) and Malonylated RebE product adding sample. The taste properties (such as sweet, licorice, sweet lingering and sour) were evaluated on a scale of −5 to 5 (−5 denoted strong masking effect and 5 denoted strong enhancing effect, 0 being the intensity of reference). Malonylated RebE product was determined to have a sweet enhancement effect and sourness masking effect. It also performed slightly licorice enhancing and lingering masking effect in test.

Malonylated steviol glycoside product obtained from Example 4 was evaluated as a sweet modifier in sucrose base or SG95 base at 30 ppm. Seven experts were asked to compare the intensity difference between reference (sucrose base or SG95 base or sucrose-citric acid base) and malonylated steviol glycoside product adding sample. The taste properties (such as sweet, licorice, sweet lingering and sour) were evaluated on a scale of −5 to 5 (−5 denoted strong masking effect and 5 denoted strong enhancing effect, 0 being the intensity of reference). Malonylated steviol glycoside product was determined to have a sweet enhancement effect. It also performed slightly licorice, sweet lingering and sourness enhancing effect in test.

The invention claimed is:

1. A compound of the following structure:

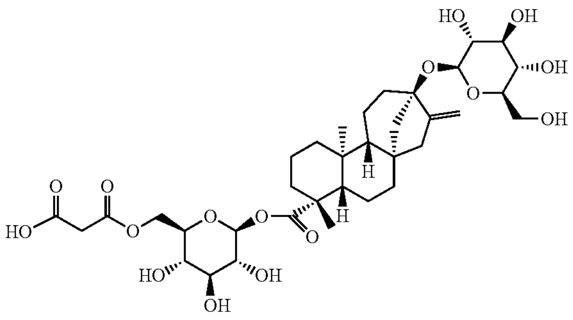

or a salt thereof.

2. A method of sweetening a comestible composition, the method comprising introducing the compound of claim 1 to the comestible composition.

3. A method of enhancing a sweet taste of a comestible composition, the method comprising introducing the compound of claim 1 to the comestible composition.

4. The method of claim 2, wherein the comestible composition comprises a sweetener.

5. The method of claim 3, wherein the comestible composition comprises a sweetener.

* * * * *